(12) United States Patent
Chen

(10) Patent No.: US 11,079,354 B2
(45) Date of Patent: Aug. 3, 2021

(54) JOSEPHSON TOROIDAL VORTEX QUANTUM SUPERCONDUCTIVE/MEMCAPACITIVE AND SUPERCONDUCTIVE/MEMRISTIVE DEVICES OF MAKING AND THEIR APPLICATIONS AT ROOM TEMPERATURE THERETO

(71) Applicant: Ellen Tuanying Chen, Rockville, MD (US)

(72) Inventor: Ellen Tuanying Chen, Rockville, MD (US)

( * ) Notice: Subject to any disclaimer, the term of this patent is extended or adjusted under 35 U.S.C. 154(b) by 0 days.

(21) Appl. No.: 16/865,340

(22) Filed: May 2, 2020

(65) Prior Publication Data

US 2020/0264130 A1    Aug. 20, 2020

Related U.S. Application Data

(63) Continuation-in-part of application No. 16/393,346, filed on Apr. 24, 2019, now abandoned, and a continuation-in-part of application No. 15/693,435, filed on Aug. 31, 2017, now Pat. No. 10,684,244.

(51) Int. Cl.
| | |
|---|---|
| *G01N 27/416* | (2006.01) |
| *G01N 27/27* | (2006.01) |
| *G01N 33/487* | (2006.01) |
| *H01L 51/00* | (2006.01) |
| *C12Q 1/00* | (2006.01) |
| *H01L 27/28* | (2006.01) |

(52) U.S. Cl.
CPC ......... *G01N 27/4161* (2013.01); *C12Q 1/006* (2013.01); *G01N 27/27* (2013.01); *G01N 33/48721* (2013.01); *H01L 27/285* (2013.01); *H01L 51/0093* (2013.01); *G01N 2800/2821* (2013.01)

(58) Field of Classification Search
CPC .. H01L 39/223–226; G01N 2800/2821; G01N 27/04–041; G01N 27/4161; G01N 27/045; G01N 27/22; G01N 27/227–228; G01N 27/27; G01N 27/327; G01N 27/3276; G01N 33/48707; G01N 33/48721; G01N 33/48735; G01N 2800/28–2828; A61B 5/40–5094; A61B 5/1468
See application file for complete search history.

*Primary Examiner* — Amar Movva

(57) ABSTRACT

Multiple Josephson toroidal vertex quantum superconductive/memristive and superconductive/memcapacitive devices were invented with various superlattice structures, which work at room temperature without an applied external magnetic flux. The first type of the superlattices of the devices comprises of multiple-layers of organometallic polymers on gold chips by self-assembling that mimics the function of Matrix Metalloproteinase-2 (MMP-2). Another type of quantum superconductor/memristor comprises of multiple-organic polymers cross-linked with MMP-2 protein forming Josephson toroidal vertex on the gold surface. Models of the quantum superconductive/memristive and superconductive/memcapacitive devices were fabricated in nano superlattice structures and the devices module configurations were described. Three different methods were used to evaluate the devices' applications in sub fg/mL collagen-1 sensing, energy storage, and the super-position characteristics as a potential quantum bit device. The superconductivity, memristive, and memcapacitive functions were also evaluated in multiple methods, respectively.

21 Claims, 55 Drawing Sheets

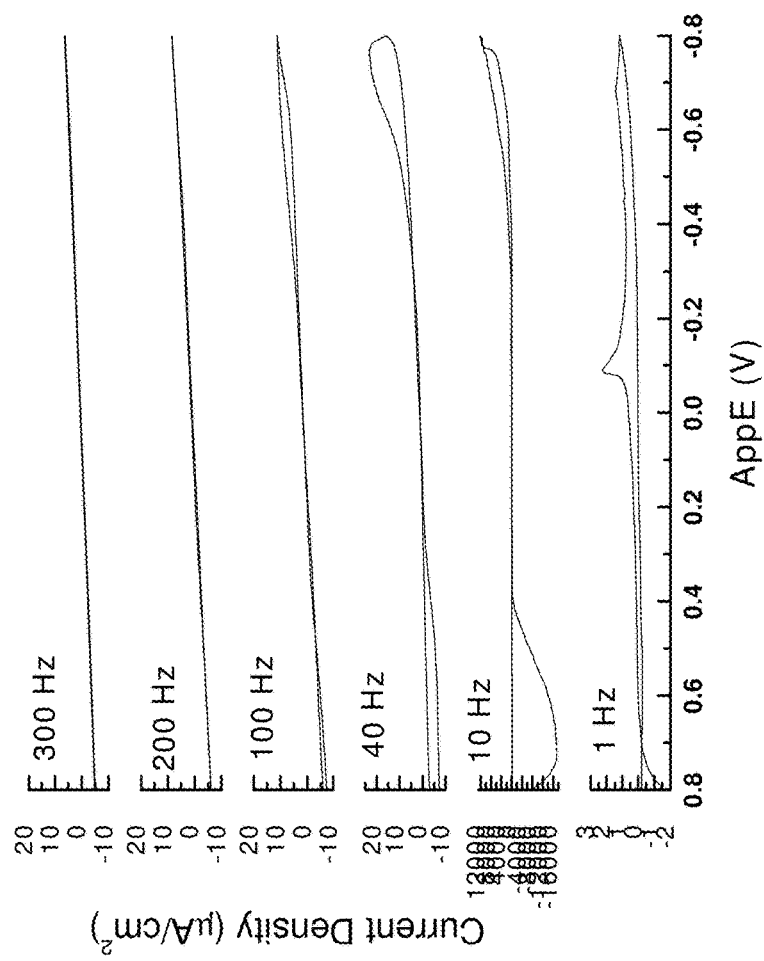

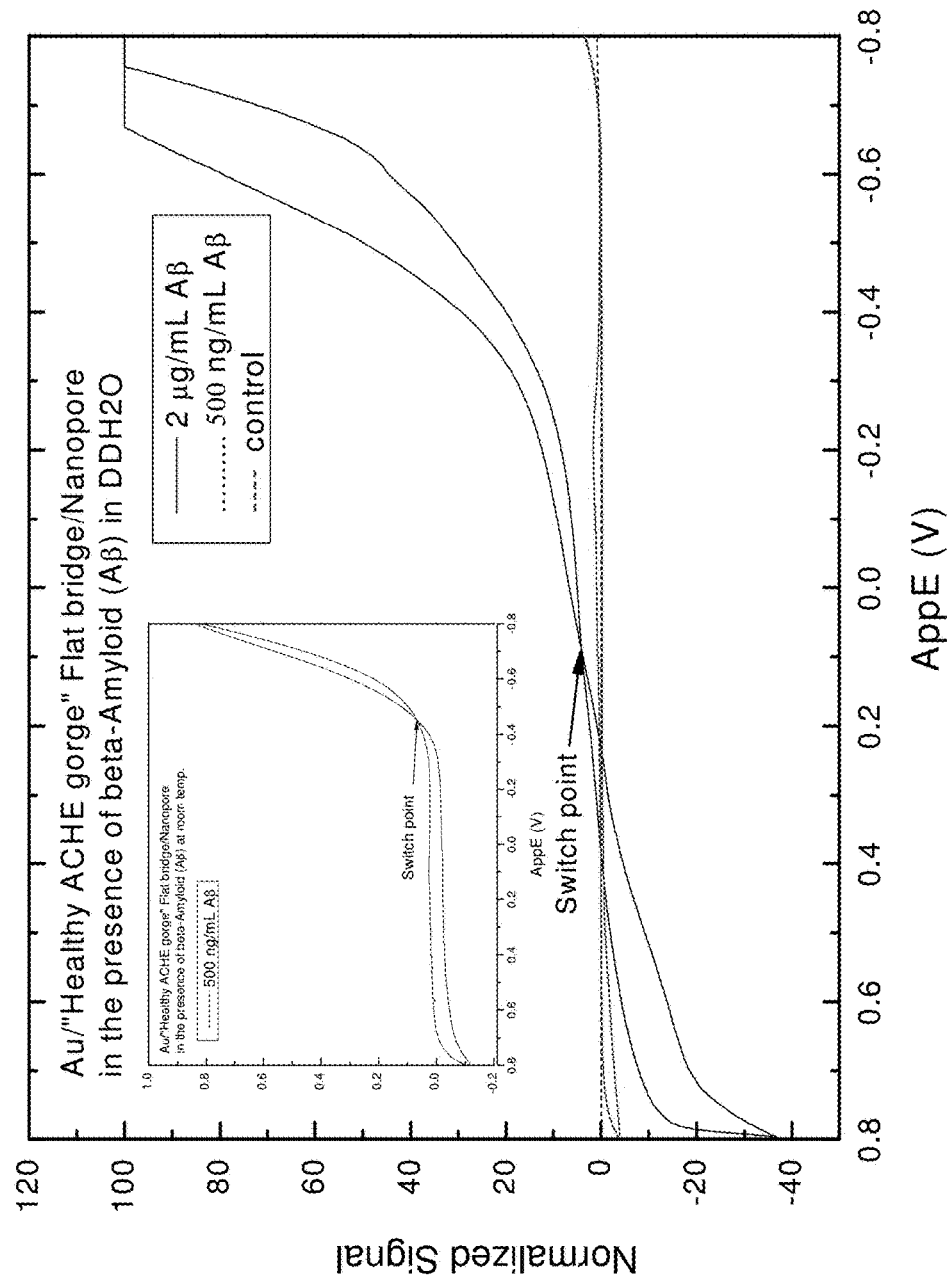

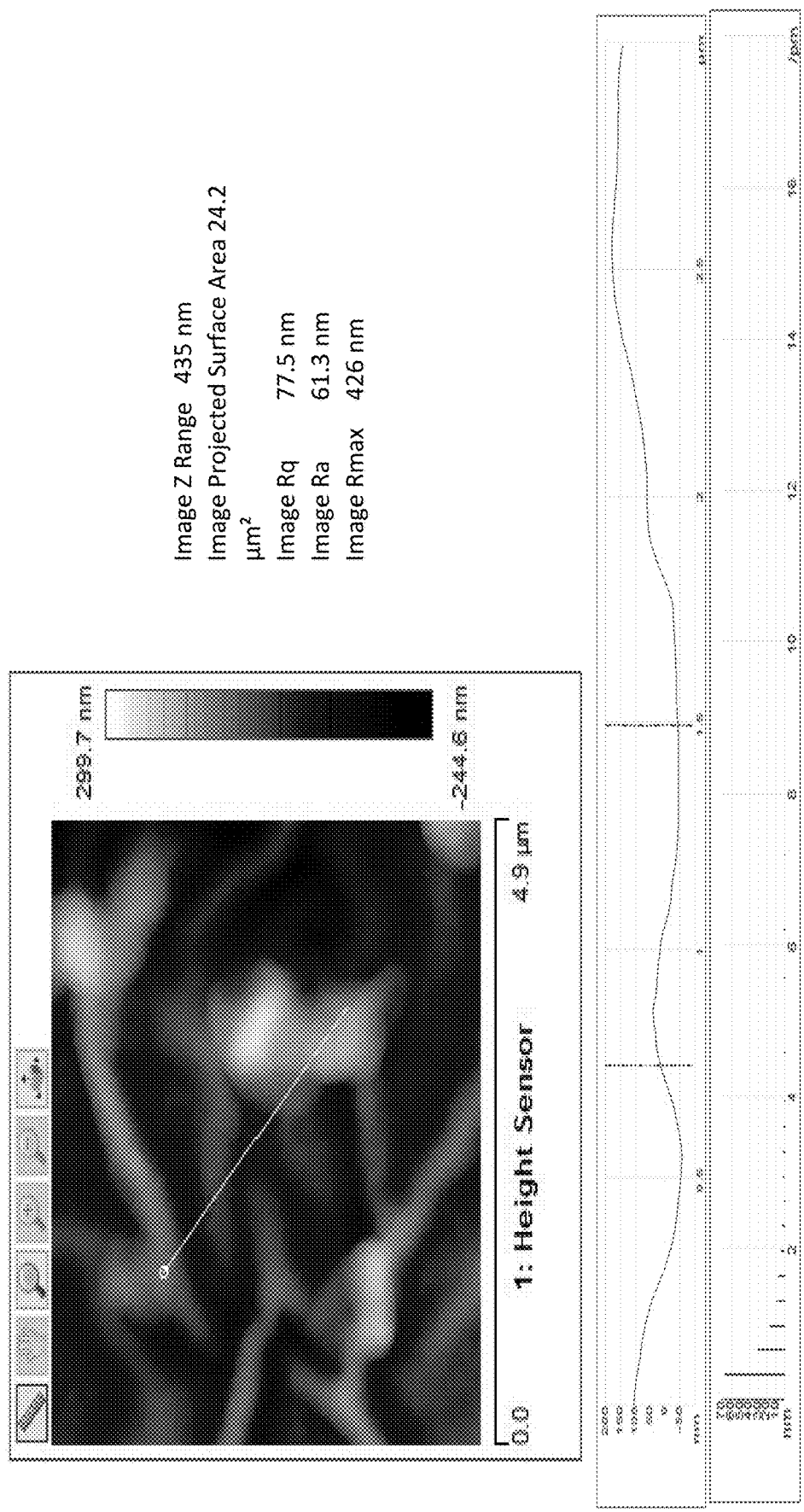

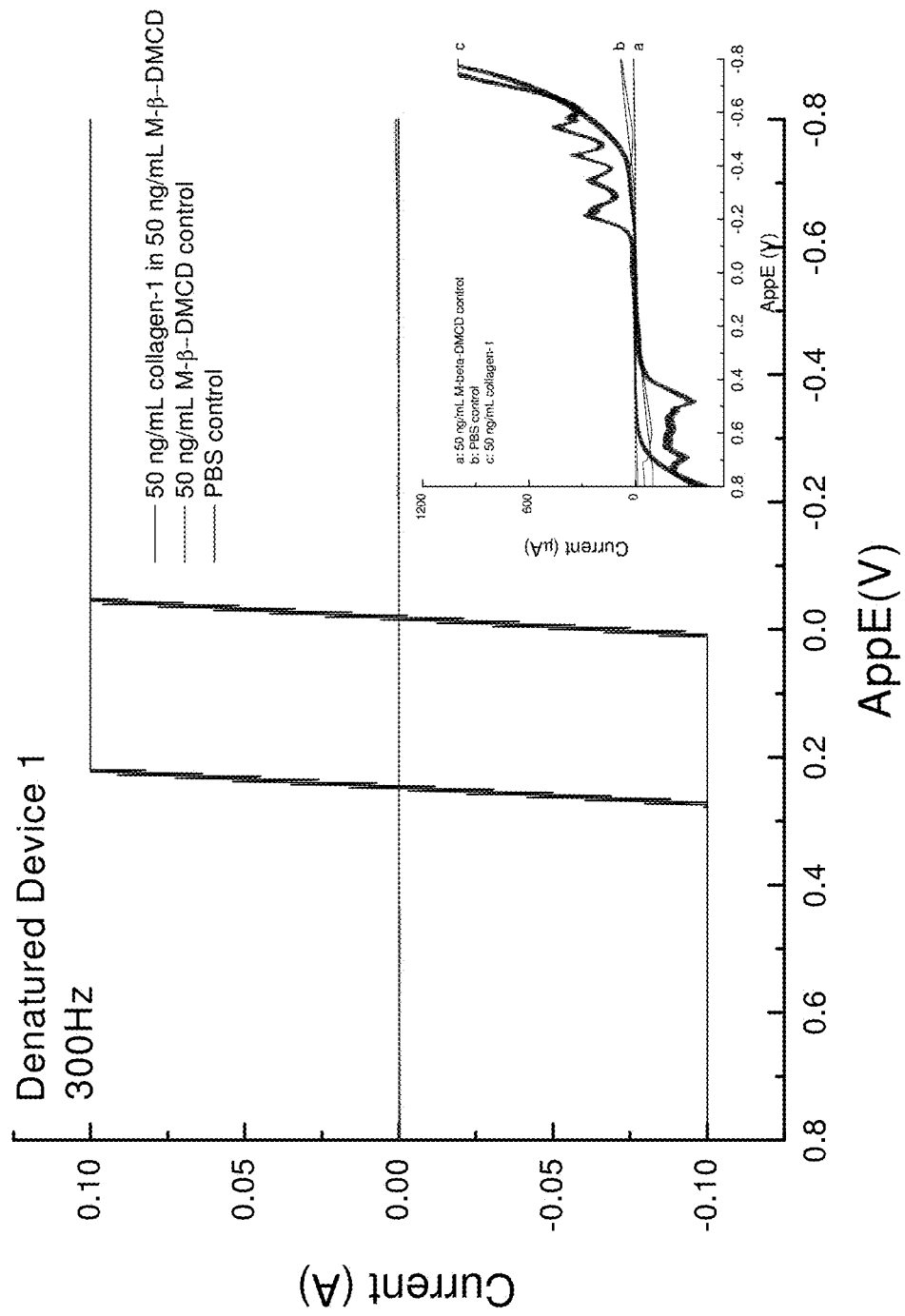

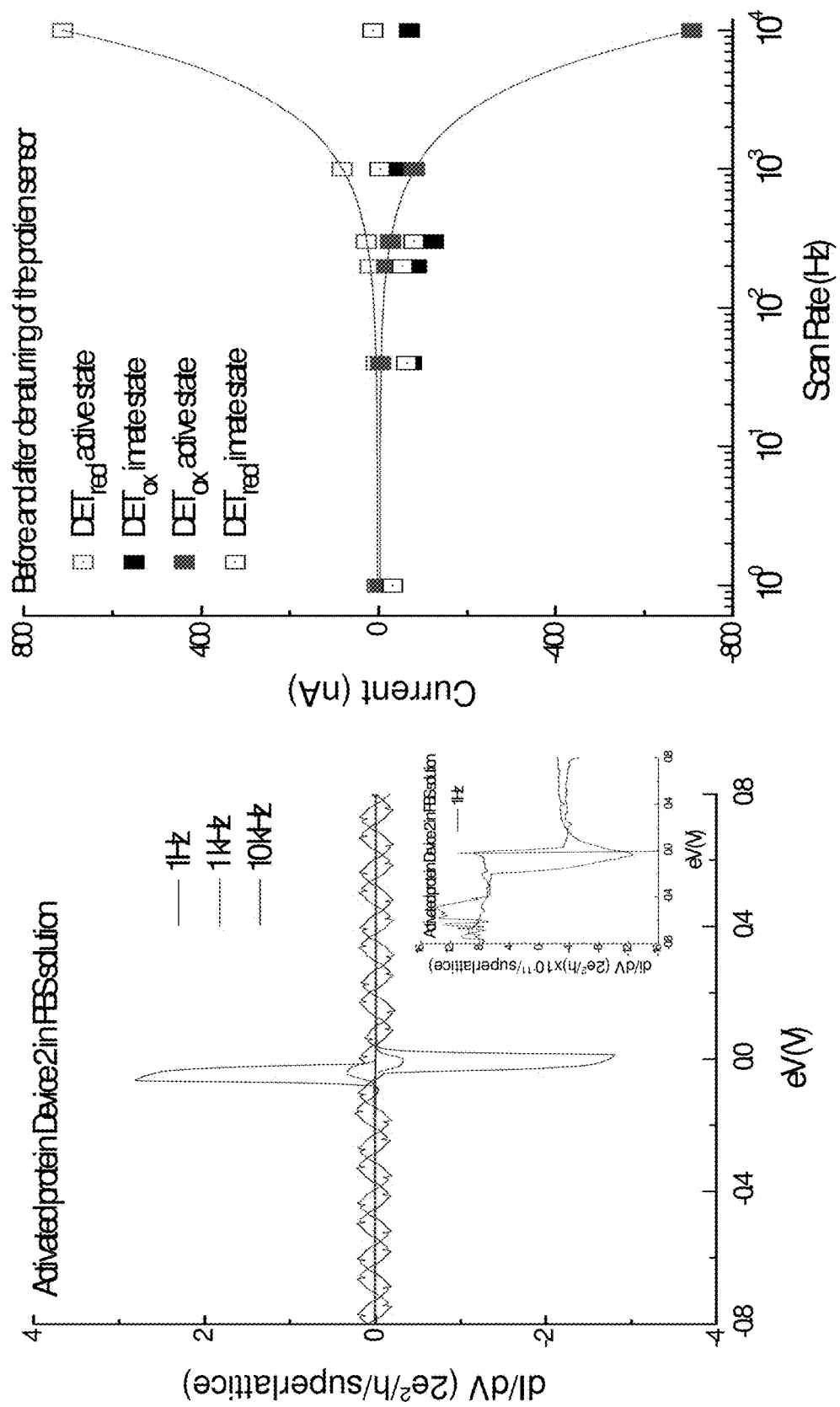

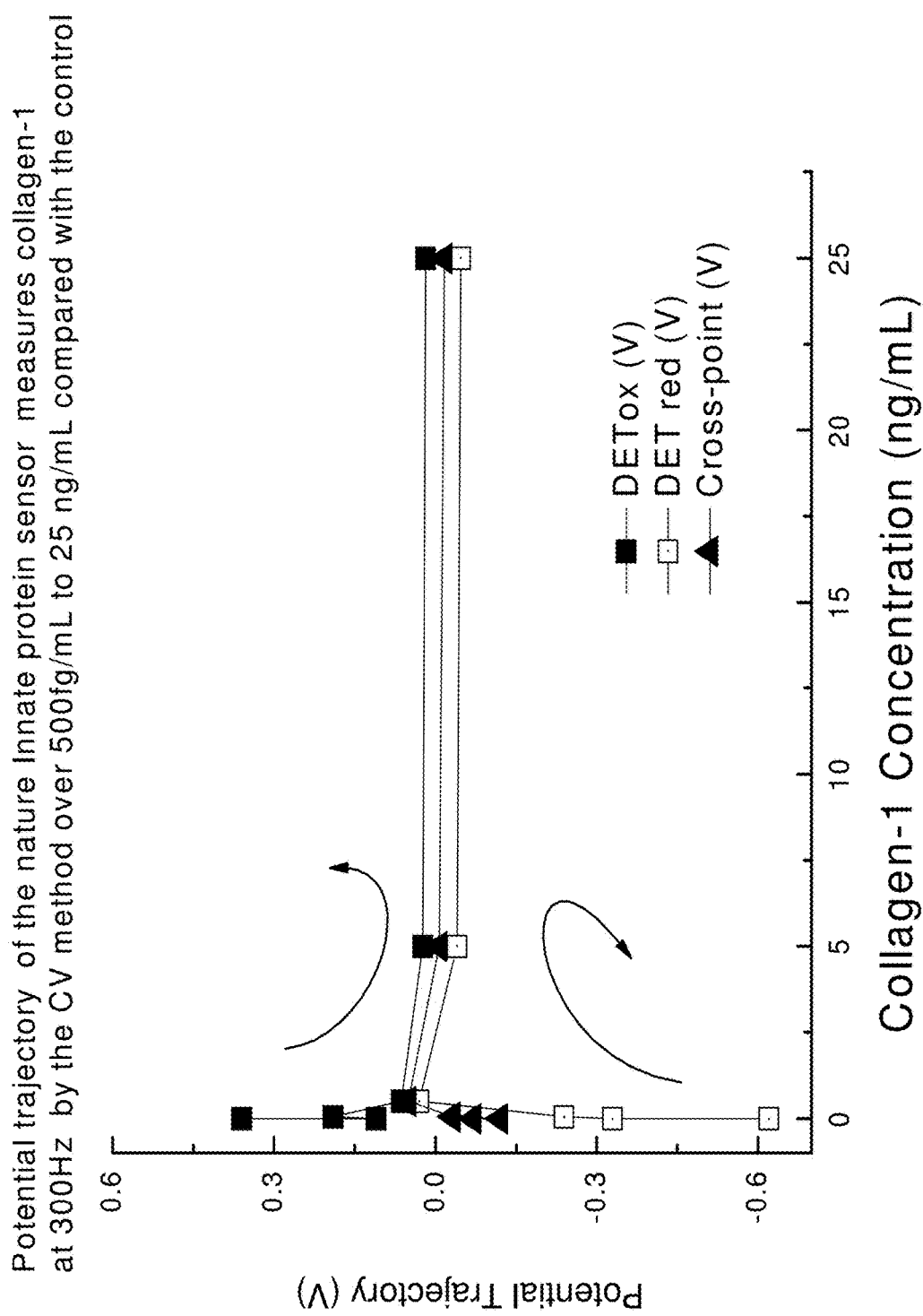

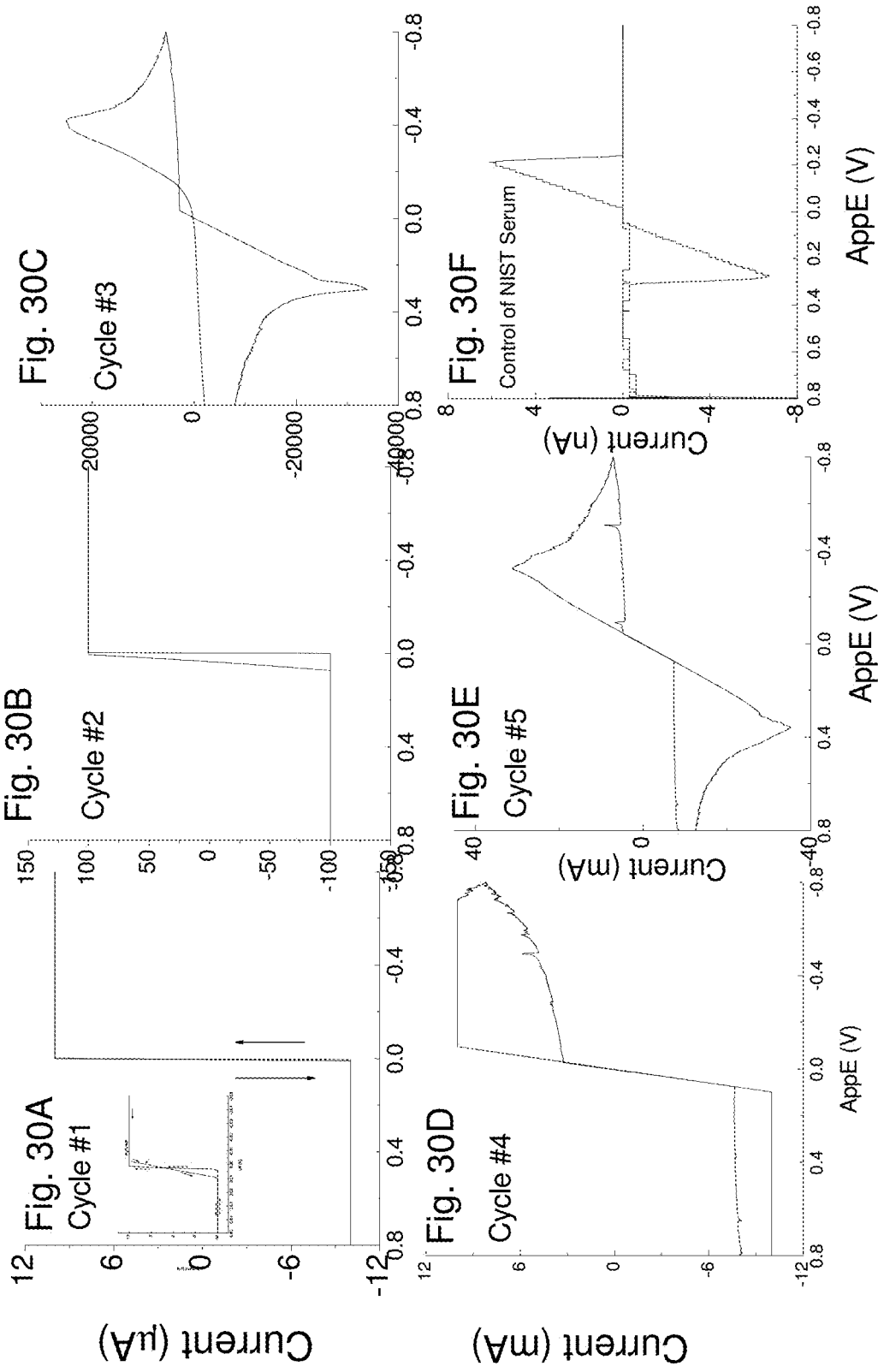

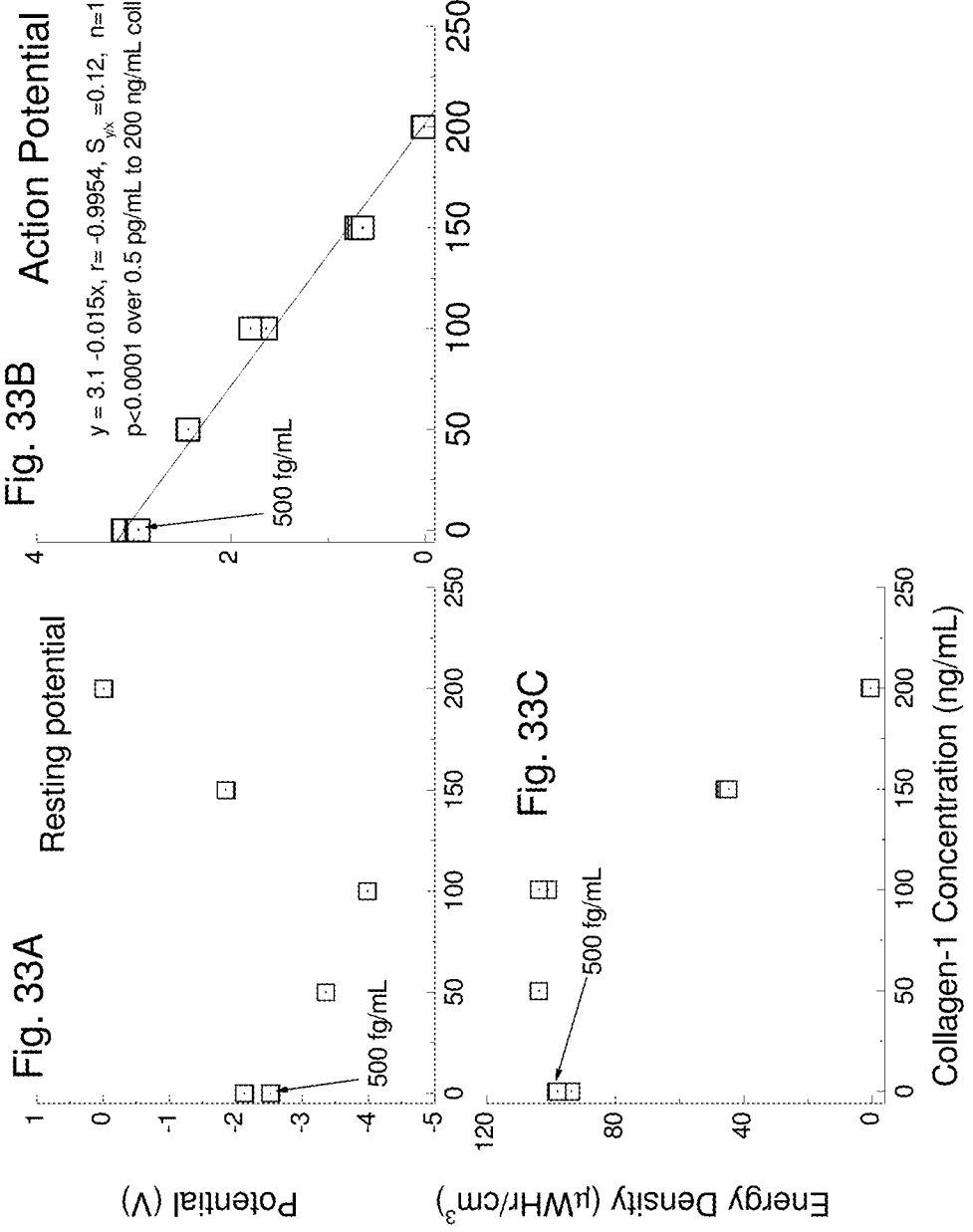

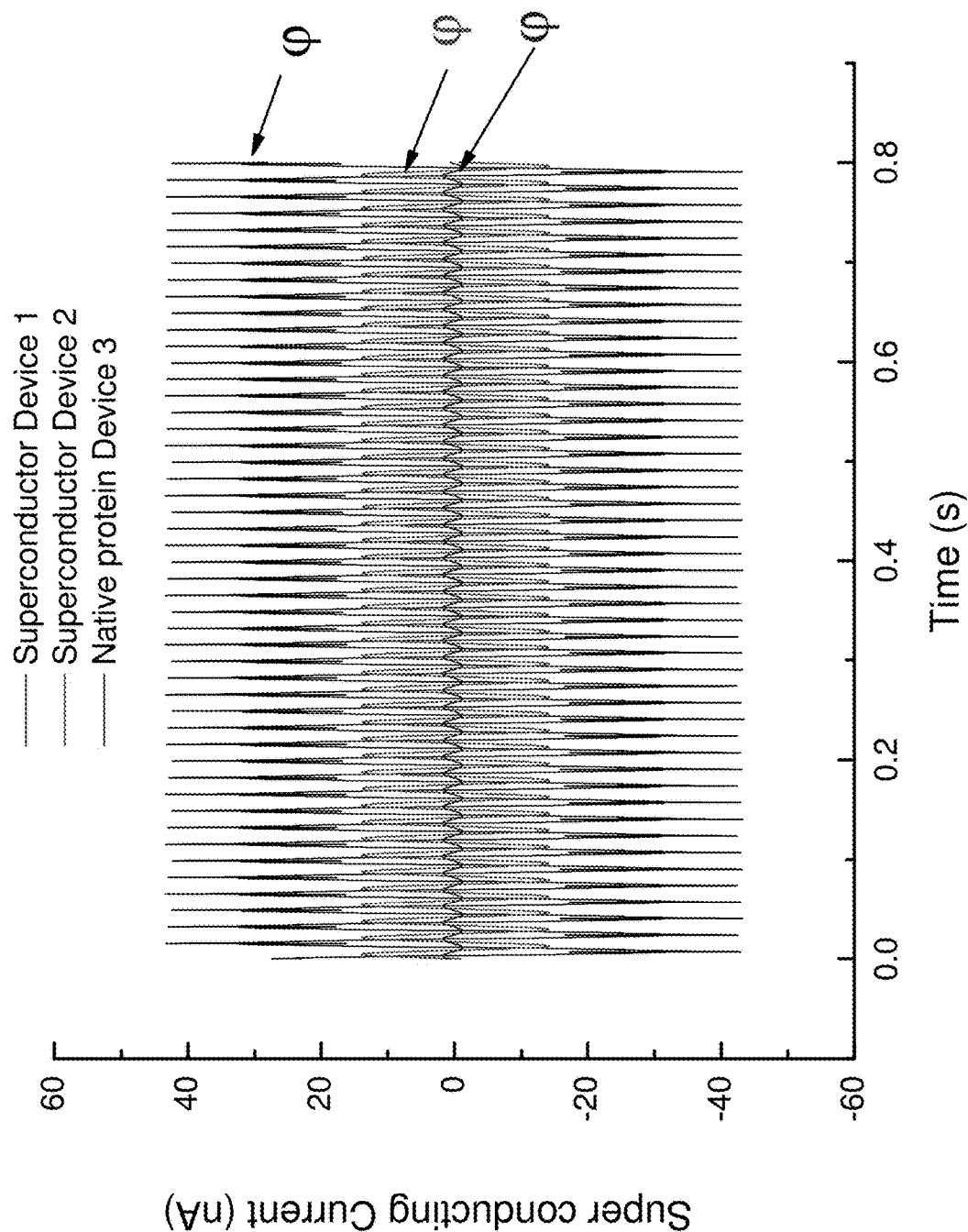

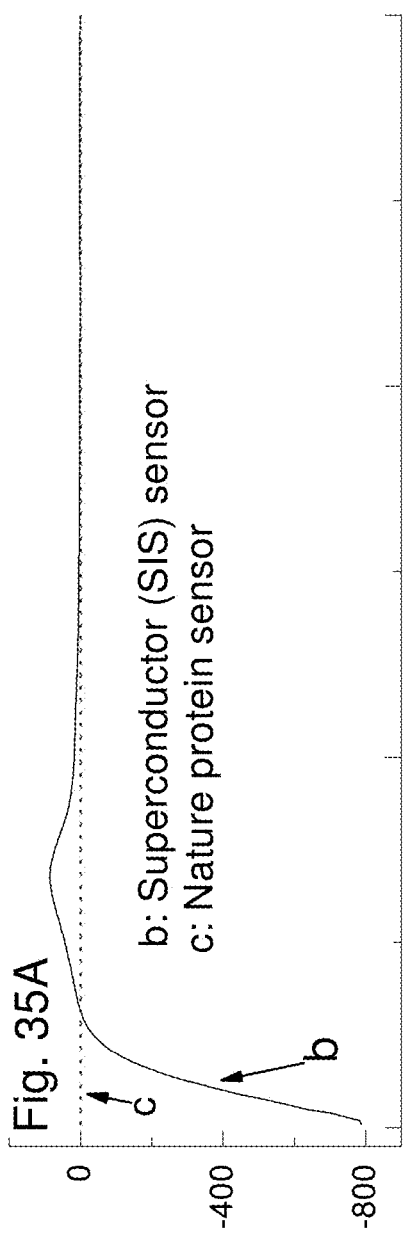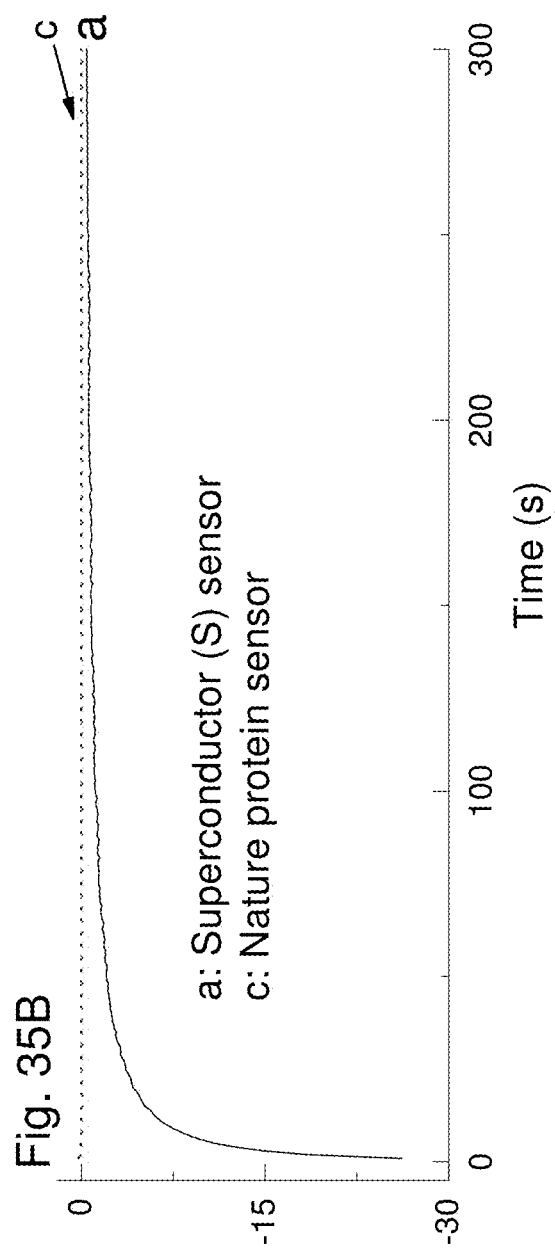

Comparing signal intensity before and after denaturing of the protein Device 3

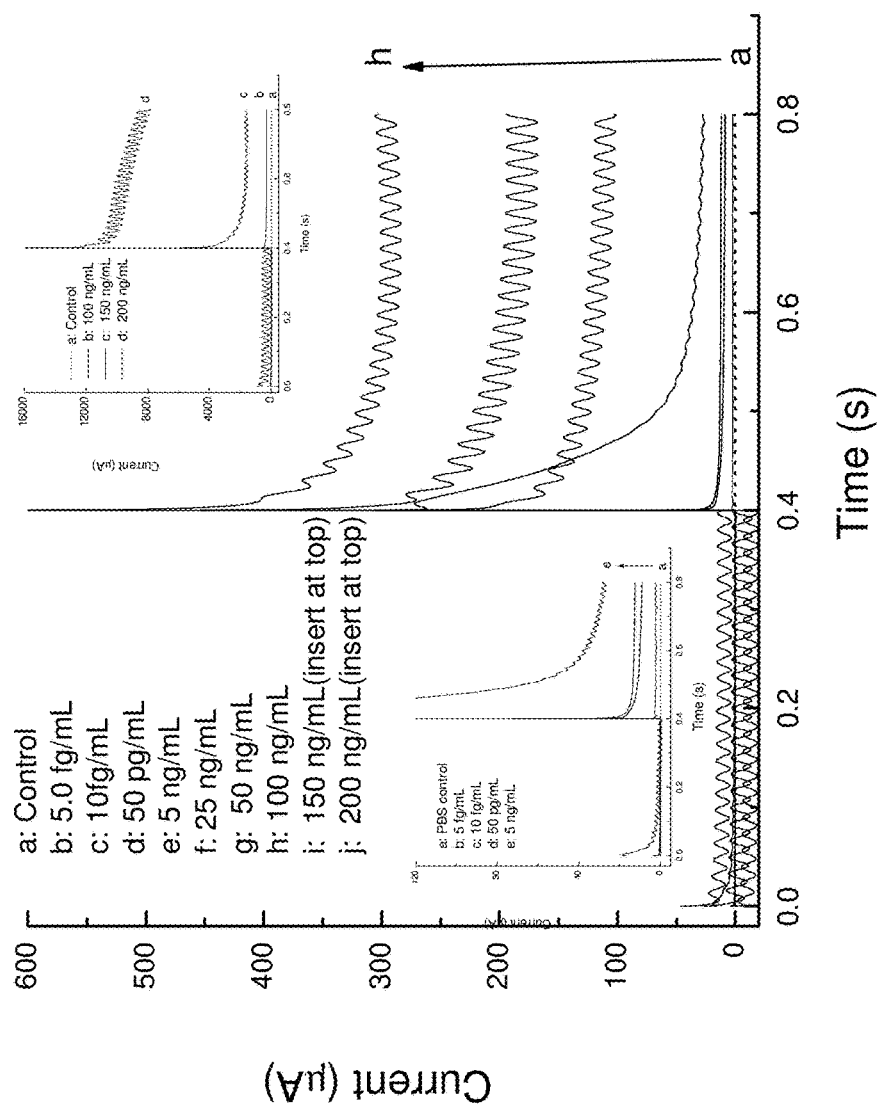

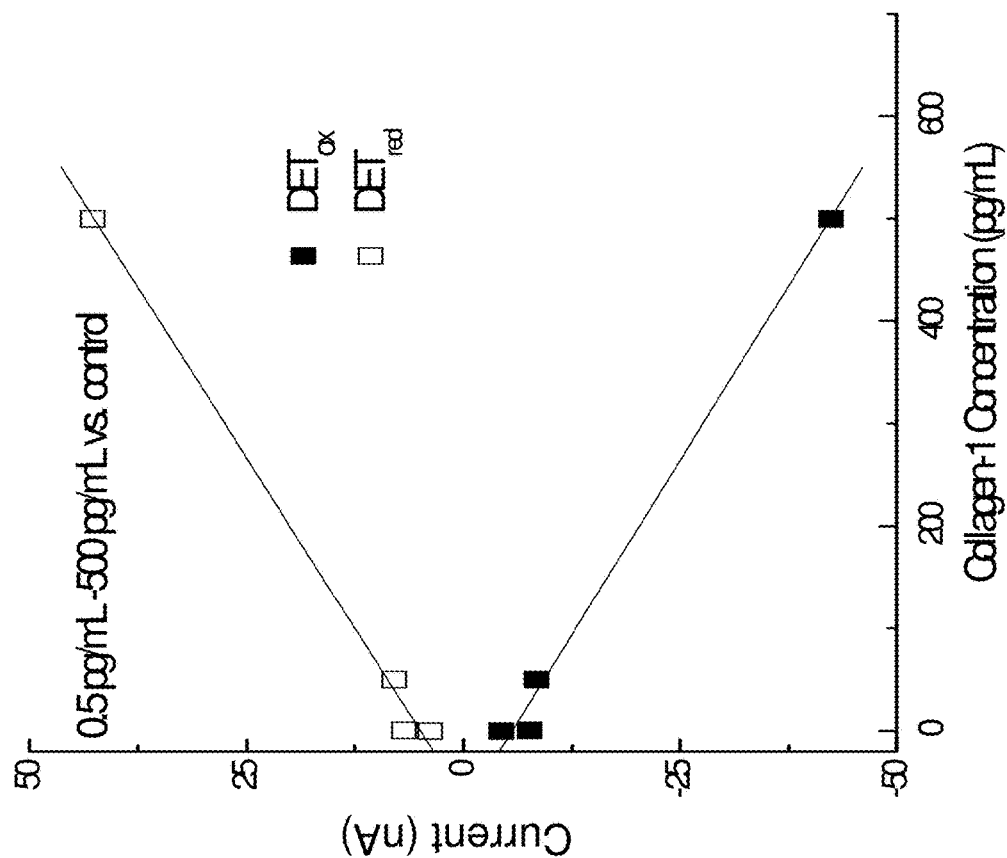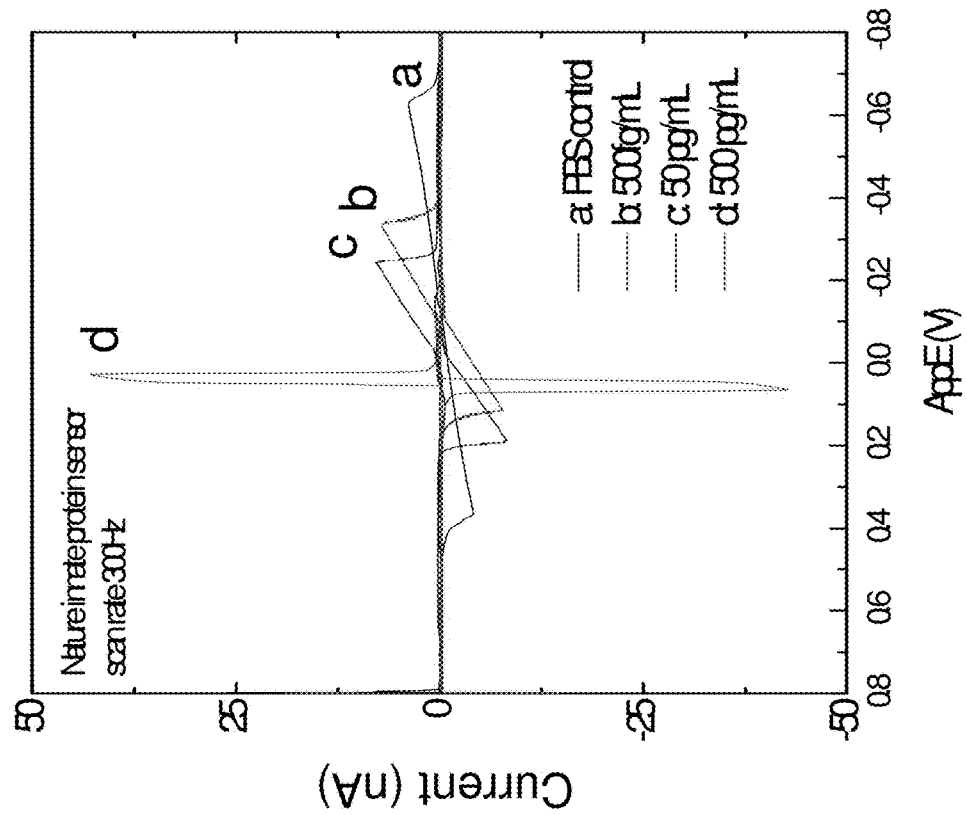
Fig. 40A
Fig. 40B

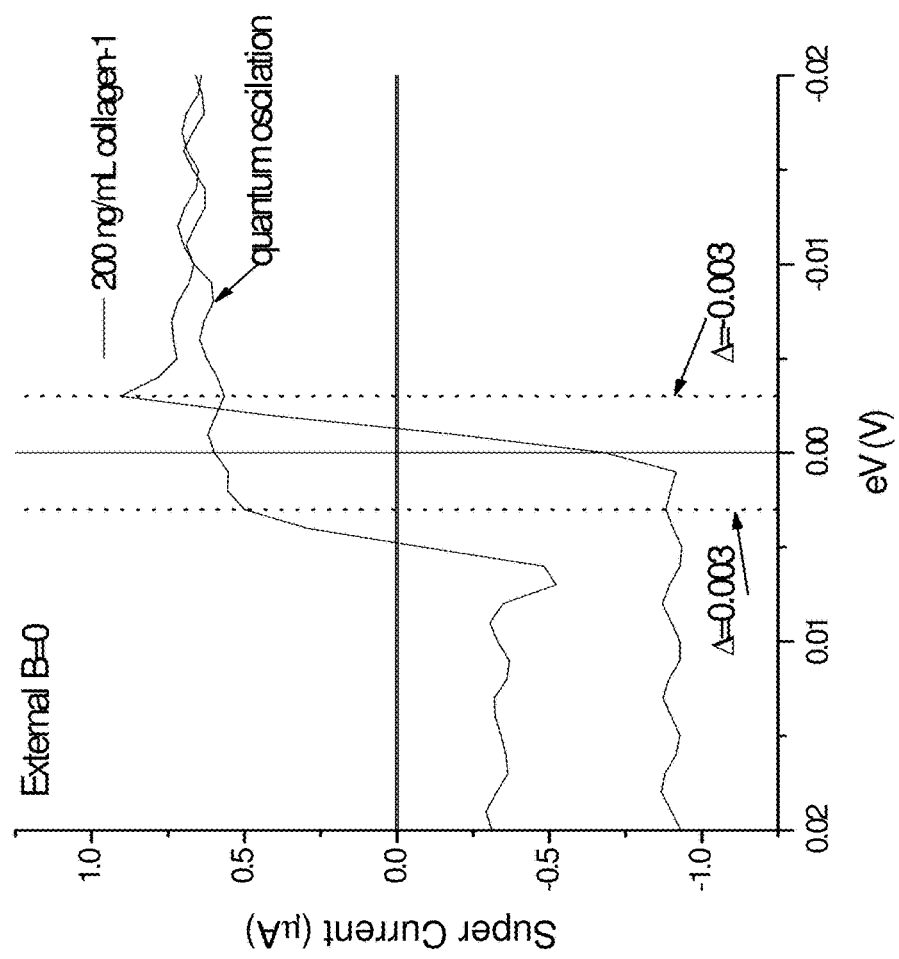
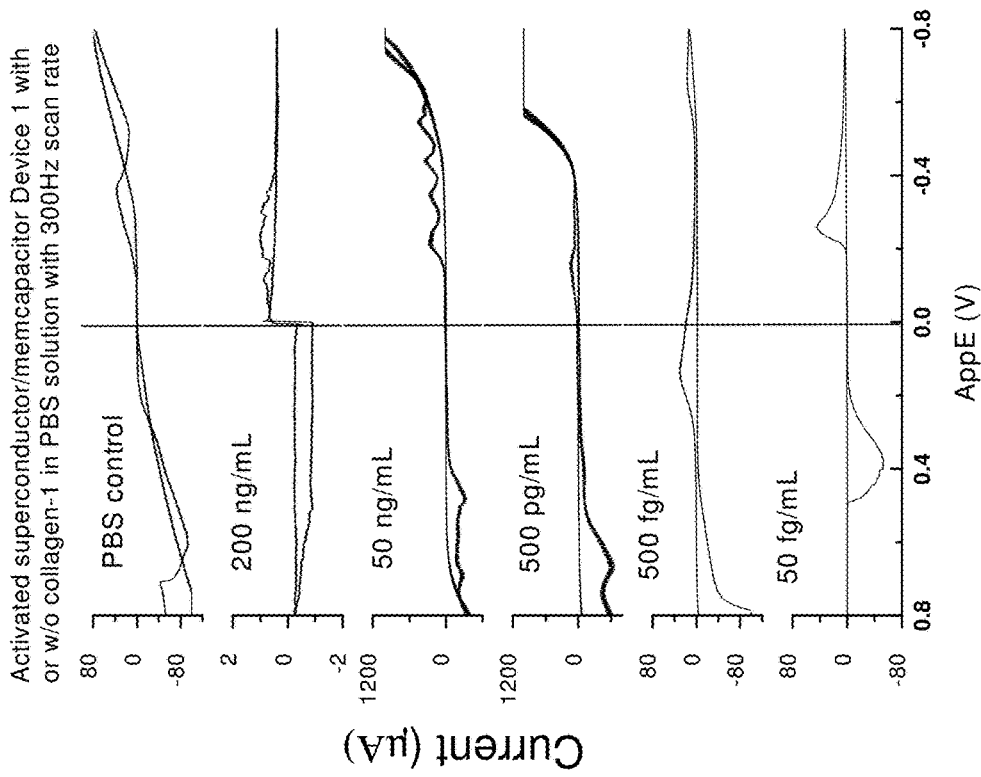
Fig. 41A
Fig. 41B

JOSEPHSON TOROIDAL VORTEX QUANTUM SUPERCONDUCTIVE/MEMCAPACITIVE AND SUPERCONDUCTIVE/MEMRISTIVE DEVICES OF MAKING AND THEIR APPLICATIONS AT ROOM TEMPERATURE THERETO

CROSS-REFERENCE TO RELATED APPLICATIONS

This patent application entitled "Josephson Toroidal Vortex Quantum Superconductive/Memcapacitive and Superconductive/Memristive Devices of Making and Their Applications at Room Temperature Thereto" is a Continuation in Part of U.S. non-provisional patent application Ser. No. 15/693,435 in title of Making Of Organic Nanobiomimetic Memristors and Memcapacitors And Its Applications In Dual Sensing Of A Biomarker In Neurodegenerative Diseases Thereto" that claims the benefit of U.S. Non Provisional patent application Ser. No. 15/693,435 filed on Aug. 31, 2017 and also claim the benefit of the U.S. Non Provisional patent application Ser. No. 16/393,346 filed on Apr. 24, 2019. The entire disclosure of the prior patent application Ser. No. 15/693,435 and 16/393,346 is hereby incorporated by reference, as is set forth herein in its entirety.

FIELD OF THE INVENTION

The invention in the title of Making Of Organic Nanobiomimetic Memristors and Memcapacitors And Its Applications In Dual Sensing Of A Biomarker In Neurodegenerative Diseases Thereto relates to the field of electrochemical sensors, in particular, to a device having both characteristics in memristor/memcapacitor acting as a dual function biosensor for detecting a biomarker that direct linked to Alzheimer's disease and other neurodegenerative diseases.

The present invention entitled of Josephson Toroidal Vortex Quantum Superconductive/Memcapacitive and Superconductive/Memristive Devices of Making and Their Applications at Room Temperature Thereto relates to the field of superconductor, in particular, to a device having both characteristics in superconductivity and memristive/memcapacitive/meminductive embedded with non-ferromagnetic switches functioning at room-temperature and its applications in sensing and energy storage.

BACKGROUND OF THE INVENTION OF SER. NO. 15/693,435

Amyloid-beta (Aβ) peptide accumulation and neurofibrillary tangle identified as major pathological biomarkers linked to Alzheimer's disease (AD) has been studied over decades. Besides significant progresses have been made, but lack of effective treatments and preventions addressed an urgent need for early diagnose and detection of Alzheimer's disease. It is estimated the global prevalence of dementia is about 24 million, and will double to 2040, leading to a costly burden disease to the society [1-3].

It would be more attractive to have a less invasive method to use than the CSF fluid method and to have an inexpensive method to use compared to a costly positron emission tomography with radiotracers. Therefore, plasma or human serum would be more desirable as specimens. Several road blocks have been hampered to reach the goals: the instability of Aβ in biological fluid [4-6], protein non-specific bounding caused high imprecision [4, 7] and the time consuming procedures of the assay. The human biomarkers for Alzheimer's research are predominantly quantified using enzyme-linked immunosorbent assays (ELISAs) that are associated imprecision of CV % values reported in literature about 20-30% [4, 7]. Calls for development of innovative tools and therapeutic approaches for better measuring preclinical and clinical biomarkers and treatment for AD is needed urgently [8-10]. Based on our experiences in development of nanostructured biomimetic sensors used for detection of toxins, blood glucose, cancers and neurotransmitters, such as acetylcholine (ACH) in biological fluid with selectivity, sensitivity and accuracy under the conditions of tracers-free, antibody-free and reagent-less [11-16], overcoming the challenges to developing nanostructured dual devices for precisely measuring preclinical Aβ in clinical useful range is encouraging to us. Providing even more useful information to clinicians and to patients is always beneficial.

Our biomimetic acetylcholinesterase (ACHE) membrane with an ACHE active site gorge deposited on a gold chip could be a best candidate to sense the presence of excess monomer Aβ, because ACHE dysregulation is well known to link to cancer, AD and other diseases [17-18]. However, direct measure Aβ, not ACH, in blood is a challenge, even though we used this "normal ACHE gorge" sensor to quantitatively detect ACHE in fM in amperometric mode [15] against a "mutated ACHE gorge" sensor, which was unable to sense ACH. Furthermore, we found the normal ACHE gorge sensor is able to serve as a memcapacitor type of memory device that clearly distinguishes conformational and neuronal circuitry change due to brain cancer cells' "bio-communicating" to the sensor [16]. Therefore, we hope the dual sensor would be able to sense the presence of Aβ in pM in order to lay a foundation for further study of the role of Aβ.

FOLLOWING IS THE BACKGROUND OF THE CIP INVENTION

Collagen is the most abundant protein in the human body. It is the primary structural component of the extracellular matrix (ECM) that is responsible for the physical maintenance of all cells [1]. The triple-helical structure of collagen assembles into insoluble collagen fibrils to strengthen the structural integrity of bones and tissues, therefore, preventing normal proteinase from engaging [1-2]. Collagen is a double-edged sword, not only actively paving the road for physiological normal cell and pathological abnormal cell adhesion, migration and intracellular communication, but also activating some receptors for either over-production or failure of matrix degradation caused by either bacterial collagenase or abnormal fibrosis from fibroblast cell, endothelial cell or epithelial cells; hence many diseases are associated with the malfunction of collagen [1-5]. A long history of traditional approach has been used for denaturing collagen as a substrate, to probe collagen degradation or to study matrix metalloproteinase (MMP) activity [6-7]. However, a clinically useful detection range at the low end for collagen-1 is difficult to accomplish due to the denaturing processing. A recent report revealed interstitial collagenase can cleave native collagen type 1 and 3, not the denatured protein, which is the major component of the fibrous plaque cap [8]. Hence, overcoming the traditional denaturing protein approach to an innovative approach is necessary. Based upon our prior experience using the biomimetic polarizable microtubule memristive/memcapacitive device to enable direct detection of MMP-2 with ag/mL level sensitivity under antibody-free, tracer-free, and reagent-free conditions [9-10], herein we propose to develop superconductive quantum devices with superlattice structure, through forming toroidal Josephson Junction (JJ) [11-12] that may be enabled directly detection of collagen-1 in the presence of a biomimetic MMP-2, compared with that of a control device with a native MMP-2.

The Josephson Junction (JJ) is a key element in the broader area of superconductivity devices [11]. At near zero Kelvin temperature, some materials become such perfect conductors that a zero-voltage superconducting current exists without energy dissipation when an external magnetic field was applied. The Josephson coupled-superconductor effect is inherent in any S-I-S tunnel junction if the two sides of barriers are sufficiently thin to allow the coupling energy from the cooper pair tunneling at the coherent wave state between the two superconductors to exceed thermal fluctuations [11-13]. Inspired by several reports and predictions [14-16], we thought the unique coherent wave state produced in the S-I-S module at a long circular JJ may be a key feature to help to accomplish the goal of this project, where we attempt to utilize a circular JJ to solve our biosensing problem. Inspired by another theoretical prediction of a π-phase difference on a topological-superconductor, (TSC)/normal metal (NM) can arise induced by Majorana spin-triplet paring, which exhibits a Josephson phase of 0 and π-junction in its ground state without any applied magnetic flux [15]. A Josephson vortex is a quantum vortex of supercurrents in a long circular junction, and the supercurrent loops create a magnetic flux which suppresses the Josephson supercurrent of the junction, making the junction a capacitor with energy periodic in 2e [13, 16].

Recent theoretical predictions of Josephson-based meminductive, memristive quantum superconducting devices have drawn attention [17-19] that the Josephson supercurrent behaves hysteretically, herein we hypothesized to develop a TSC/quantum memristor (QMR) or a TSC/quantum memcapacitor (QMC) device that is able to measure collagen in a biological fluid sample without denaturing the protein may be accomplishable. It is well known that superlattice membranes have been used as candidates for applications in superconductivity [20]. Our group intentionally fabricated the TSC/QMC (as Device 1) and the TSC/QMR devices (as Device 2) without embedding collagen, so we can see the superlattice structures, and evaluate the function of collagen when we applied it on the membranes; and when compared to a native MMP-2 protein device (Device 3), that may help our understanding of the role of collagen interaction with biomimetic MMP-2 and native MMP-2 at the toroidal Josephson junction vortex.

SUMMARY OF INVENTION

It is an object of the present invention to provide a new generation of organic memristor/memcapacitor compromising the active sites of a biomimetic ACHE gorge in the membrane of the device.

It is an object of the present invention to provide a new generation of organic memristor/memcapacitor with a "biomimetic linen" attached inside of the biomimetic ACHE gorge thereto.

It is an object of the present invention to provide a new generation of organic memristor/memcapacitor with multiple-layers and cross-bars forming a biomimetic neuronal network matrix.

It is an object of the present invention to provide a new generation of organic memristor/memcapacitor that is capable for dual sensing functioning of a biomarker Aβ in Alzhermer's patients in current and voltage change without using antibody, mediator, labels and tracers.

It is a further object of the present invention to provide a new generation organic memristor/memcapacitor to be able to sense sub pM Aβ in biological fluid without instability and the improved sensitivity and accuracy is set forth over a wide useful clinical range.

SUMMARY OF THE CURRENT CIP INVENTION

It is an object of the present invention to provide a new generation of Josephson toroidal vortex quantum superconductive/memristive device comprising multiple-layer superlattices made by self-assembling cross-linked organometallic polymers that facility cooper pair electrons hopping through the superlattices between the long Josephson toroidal vortex junction causing the Friedel-oscillation that paves a road for room temperature quantum superconducting with a memristive memory behaving.

It is an object of the present invention to provide a new generation of Josephson toroidal vortex quantum superconductive/memristive device having arrays of curvature single-wall organic nanotube coordinating with transition metal in $d_\pi$ chelating.

It is an object of the present invention to provide a new generation of Josephson toroidal vortex (JTV) quantum superconductive/memristive device facilitating long-range direct electron-relay between biomimetic CHAT . . . biomimetic MMP-2 . . . collagen-1 within the boundary of the JTV superlattice that the changing phases of the cooper pair waves may promote and store eternal magnetic flux energy as a function of collagen-1 concentration without applying an external magnetic field.

It is an object of the present invention to provide a new generation of Josephson toroidal vortex (JTV) quantum superconductive/memristive device that possesses extremely high quantum conductance density per superlattice at zero-bias that produces super current leading to be exponentially proportional to collagen-1 concentrations.

It is an object of the present invention to provide a new generation of Josephson toroidal vortex (JTV) quantum superconductive/memristive device having dual functioning as a sensing device and of an energy harvesting device.

It is an object of the present invention to provide a new generation of Josephson toroidal vortex (JTV) quantum superconductive/memcapacitive device based solely on the driving force of fractional Josephson vertices that depend on the supercurrent loops created a magnetic flux in which the superconducting phase discontinuities, herein it does not need an external applied magnetic field to be functional.

It is an object of the present invention to provide a new generation of Josephson toroidal vortex (JTV) quantum superconductive/memristive device comprising of innate protein cross-linked with organic conducting polymers that process superconductive/memristive zero-bias peaks in the presence of collagen-1 and the supper current intensity is inversely proportional to the collagen-1 concentration.

It is an object of the present invention to provide a new generation of Josephson toroidal vortex (JTV) quantum superconductive/memristive device comprising of innate protein cross-linked with organic conducting polymers that can quantitatively detect collagen-1 without a denaturing protein process.

It is an object of the present invention to provide a method effectively control the intensity of the Friedel-oscillation in the superlattice at the JTV boundaries in order to find its application in sub fg/mL protein sensing using a CA method.

It is an object of the present invention to make the biomimetic MMP-2 quantum superconductor/memristor device having orders of magnitude higher super conductance and signal intensity than that of the protein MMP-2 superconductor/memristor device in both innate and activated state, respectively.

BRIEF DESCRIPTION OF THE DRAWINGS

FIG. 5C depicts frequency affects on CV curves from 1 to 300 Hz in NIST SRM965A human serum with certified blood glucose in level 2 (70 mg/dL) with 76 nM Aβ.

FIG. 6 illustrates the CV profiles without TCD. The control is in red; the insert is 380 nM Aβ; the solid black curve is with 1.52 μM Aβ.

FOLLOWINGS ARE THE BRIEF DESCRIPTIONS OF THE DRAWINGS FOR CIP APPLICATION

Figure 15:
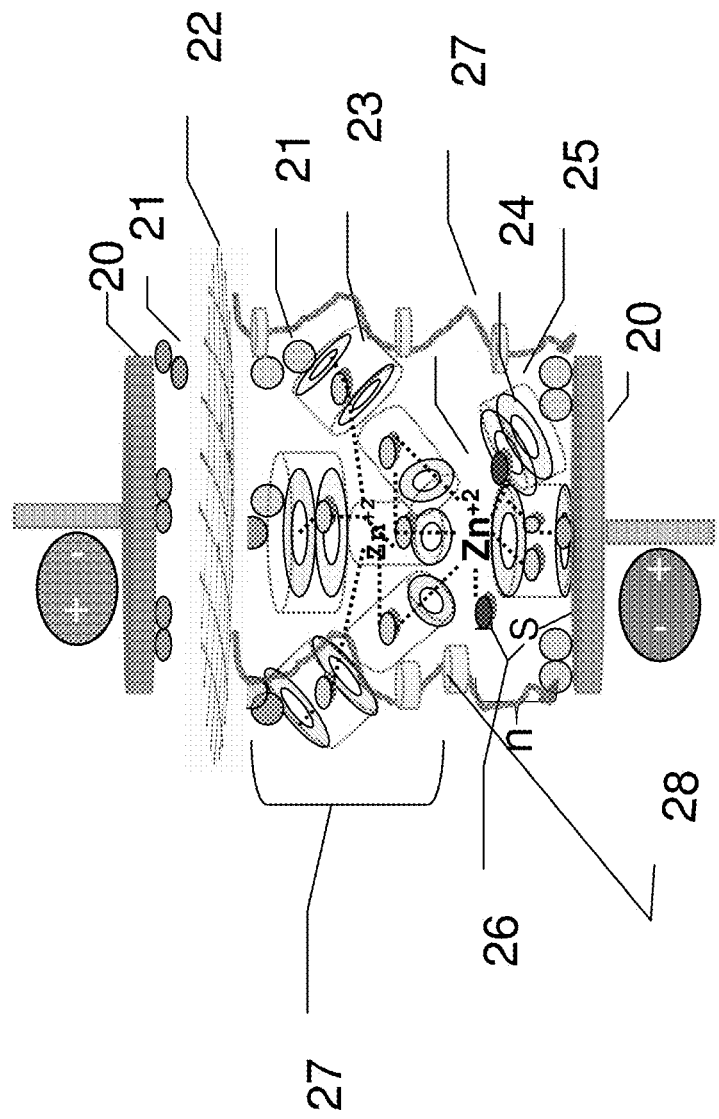

FIG. 15 depicts the schematic components in the engineering design of the superconductive/memcapacitive/memristive device 1 in a front-face view. "20" is the gold electrode with 50 nm thickness adherences on a flexible plastic plate substrate with a switchable connection; "21" is the Cooper pair electrons, "22" is the collagen-1 matrix, "23" refers to the zinc ions formed coordination complex with ligands of mono-imidazole modified-β-dimethylcyclo-dextrin (mM-β-DMCD), in short as MCD, that are in two schemes: (1) the zinc ion chelated with four imidazole groups in cavities of four MCDs and also with one COO group of TCD; another scheme is the zinc ions chelate with three imidazole groups in three MCDs and the fourth ligand is with either the $COO^-$ group from the TCD as "24" or with the $COO^-$ group from N-acetyl-L-cysteine referred to as "25", and the fifth ligand is with the imidazole group in bM-β-DMCD; "26" refers to the repeating processing of n units; "27" refers to the PEG . . . PVP forming biomimetic proteins' N-terminal vertical architecture of the toroidal memristive structure; "28" refers to the PEG . . . TCD chain forming biomimetic proteins' C-terminal vertical architecture of the toroidal; "29" refers to the repeated units. Notice there is an air gap space around zinc ions.

Figure 16:
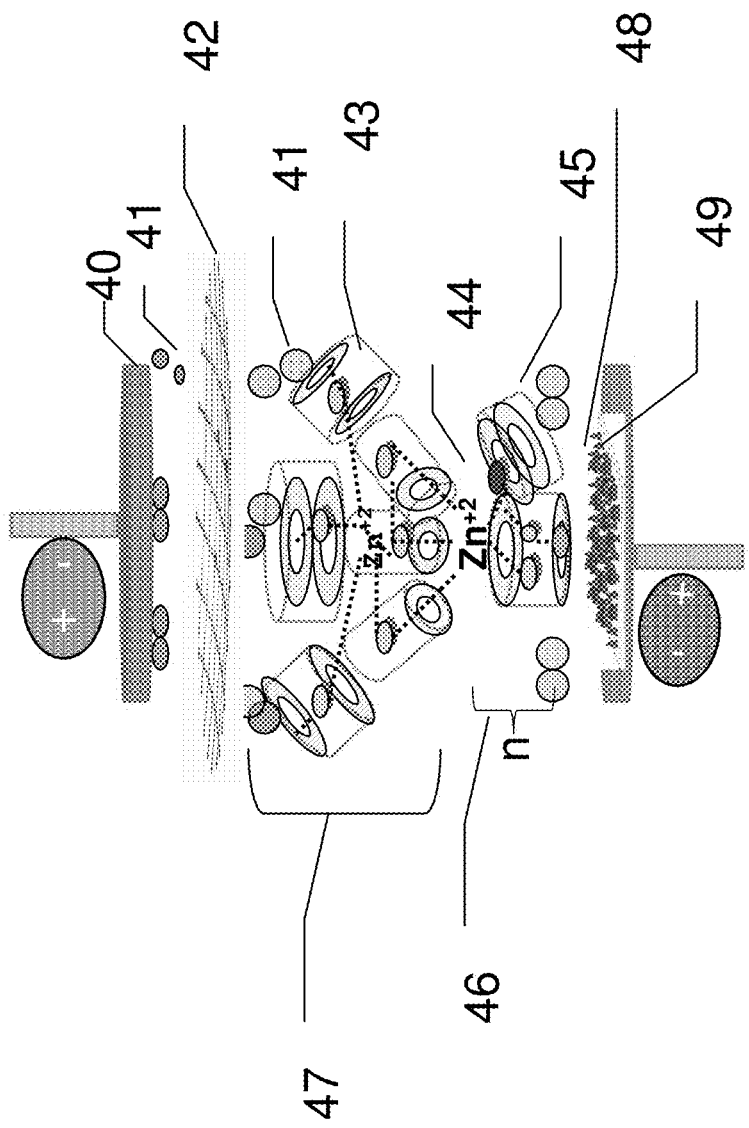

FIG. 16 depicts the schematic components in the engineering design of the superconductive/memristive/meminductive (SMRMI) device 2 in a side view. "40" is the gold electrode with 50 nm thickness adherences on a flexible plastic plate substrate with a switchable connection; "41" is the Cooper pair electrons, "42" is the collagen-1 matrix as an insulator, "43" refers to the zinc-imidazole of the MCD coordination complex: zinc ion chelated with four imidazole groups in cavities of four MCDs, and also chelates with the $COO^-$ group of TCD; another zinc ion chelates with three imidazole groups in three MCDs, and with one $COO^-$ group of TCD as "44", and one ligand with imidazole group in bM-β-DMCD as "48"; "45" refers to the repeating processing of "n" units; "46" refers to the PEG . . . PVP forming biomimetic proteins' N-terminal vertical architecture of the toroidal memristive structure; "47" refers to the PEG . . . TCD chain forming biomimetic proteins' C-terminal vertical architecture of the toroidal; "48" refers to the repeated units. Notice there is an air gap around zinc ions. "49" refers to the repeated units. "50" refers to the nanoislands structure membrane on 50 nm thickness gold electrode on a plastic substrate with a switchable gold electronic connect lead; the nano-island membrane comprises of TCD . . . PEG . . . PVP . . . β-CD copolymer, that mimics choline acetyltransferase (CHAT).

Figure 17:
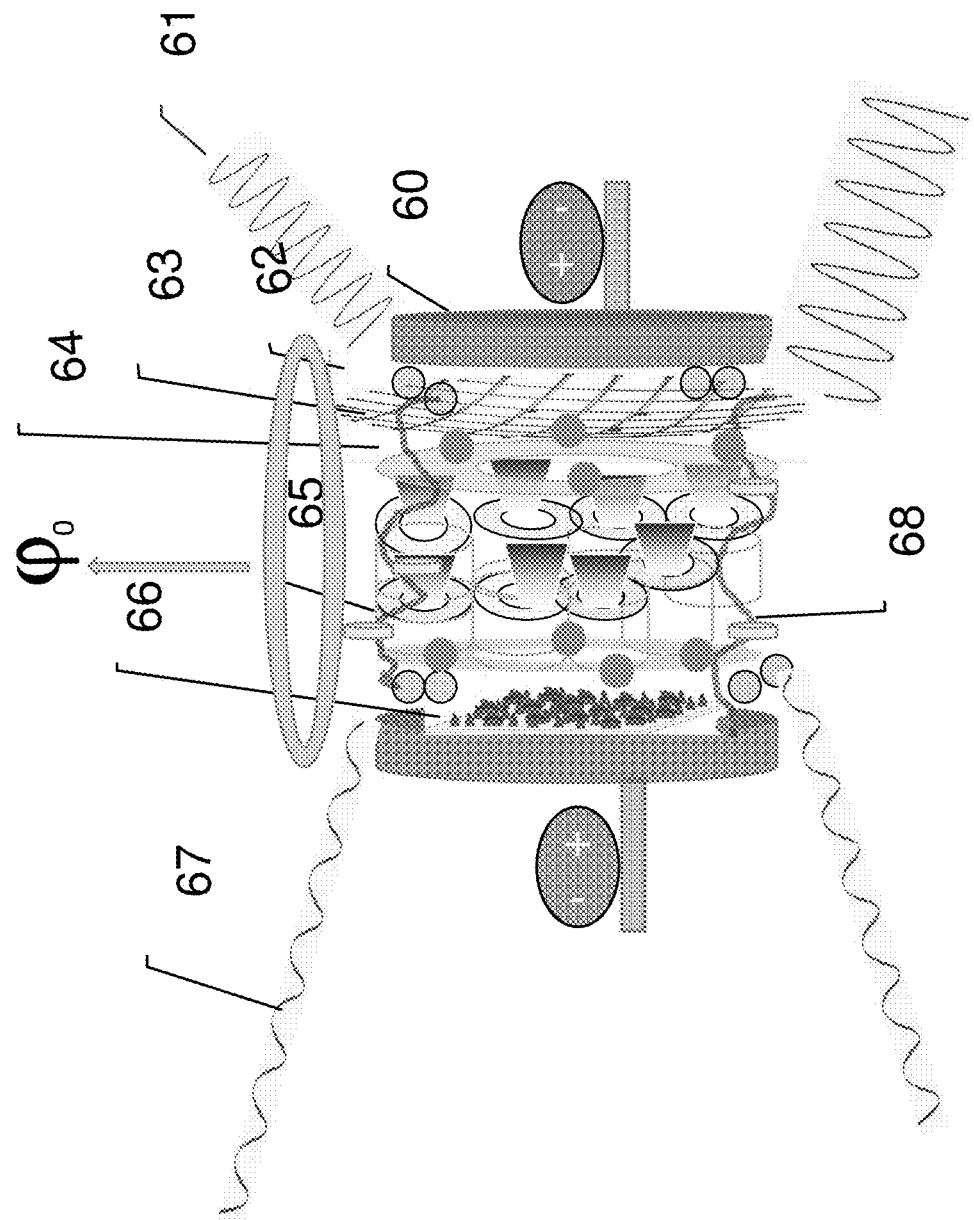

FIG. 17 depicts the art model for Device 2 in a side view of the Josephson Junction. "60" is the electrode; "61" is the amplified wave after the Cooper pair went through the multiple superconductor-Insulator-superconductor (SIS) layers at a higher frequency. "62" refers to the Cooper pair; "63" refers to the collagen-1 matrix; "64" refers to the circular current flow in a positive direction with the zinc atoms as the brown balls; "65" refers to the cyclodextrin array matrix alignment with each other produced the eternal superconducting current in the blue circle having induced a $\varphi_0$, single flux quantum, that a non-ferromagnetic field is produced; "66" is the nanoisland membrane on the gold electrode; "67" is the wave of cooper pair electrons after passing through the nanoisland membrane; Notice there is an air barrier between the membrane and the array of cyclodextrin matrix. "68" refers to the PEG . . . PVP's N-terminal chain.

Figure 18:
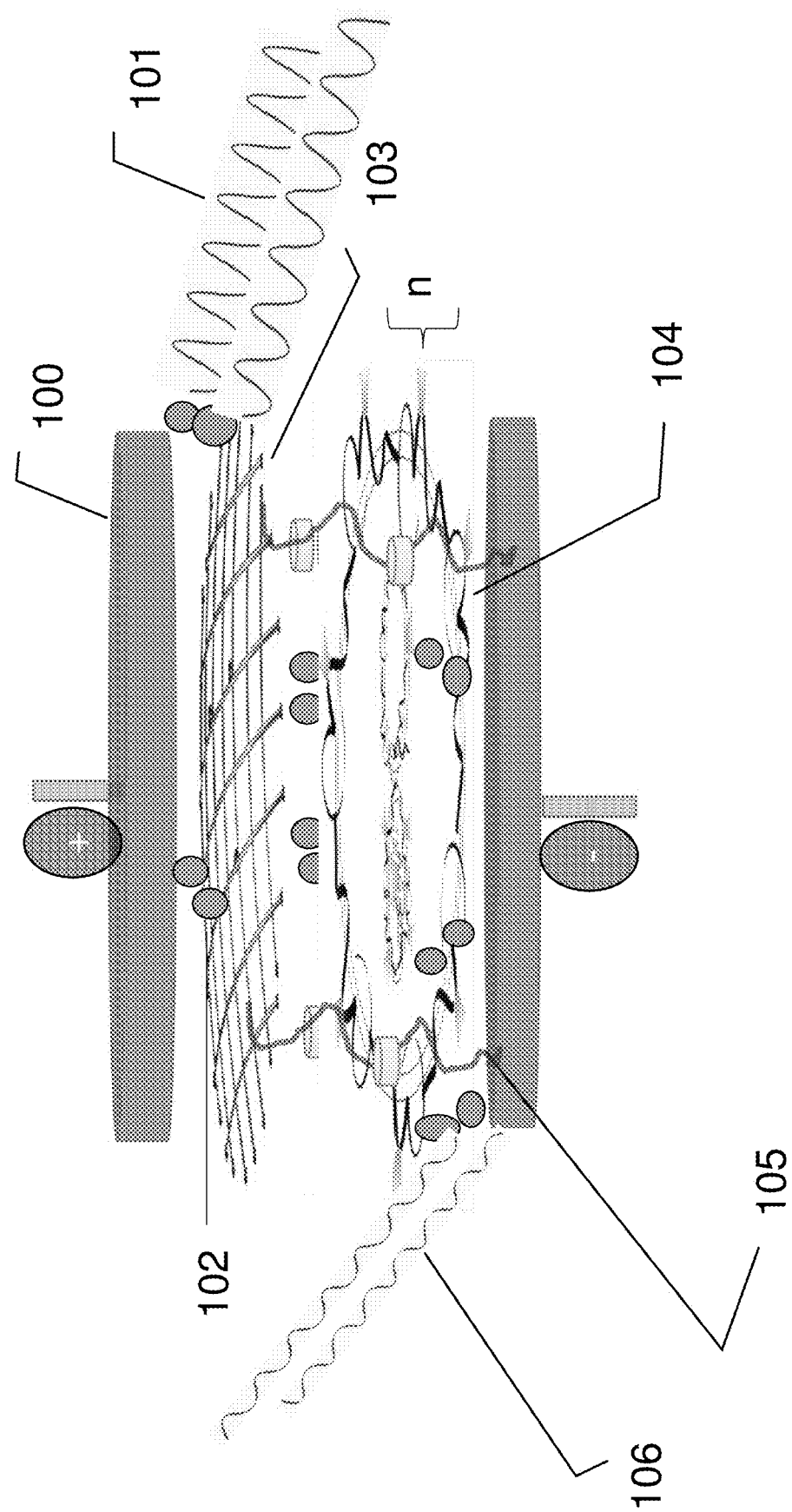

FIG. 18 depicts schematic components of the superconductive/memristive (SMR) activated MMP-2 protein device 3 in a side-view. "100" refers to the electrode; "101" refers to the amplified wave after the cooper pairs passed through the layers of superconductive-insulator-superconductive membranes; "102" is the cooper pair; "103" refers to the collagen-1 matrix; "104" refers to the superconducting membrane in horizontal orientation that comprised of the native MMP-2, TCD, PEG, and PVP. The blue diamonds on the rings refer to the migrated zinc atoms from the MMP-2. Inside have two small rings referring to multiple toroidal matrix arrays and it repeated for multiple times. Notice there is an air gap between the toroidal rings. Hence it comprised an SIS-SIS-SIN chain for amplification. "105" refers to the PEG . . . TCD vertical chain mimicking of C-terminal of a protein, and the right-hand side of the similar chain referrers to the PEG . . . PVP chain of mimicking N-terminal chain. "106" refers to the supercurrent wave from the Cooper pair after they passed through the superconducting layer. The two blue circles refer to the circler superconducting current that produced single flux quantum with the blue arrow is the induced electromagnetic field.

Figure 19:
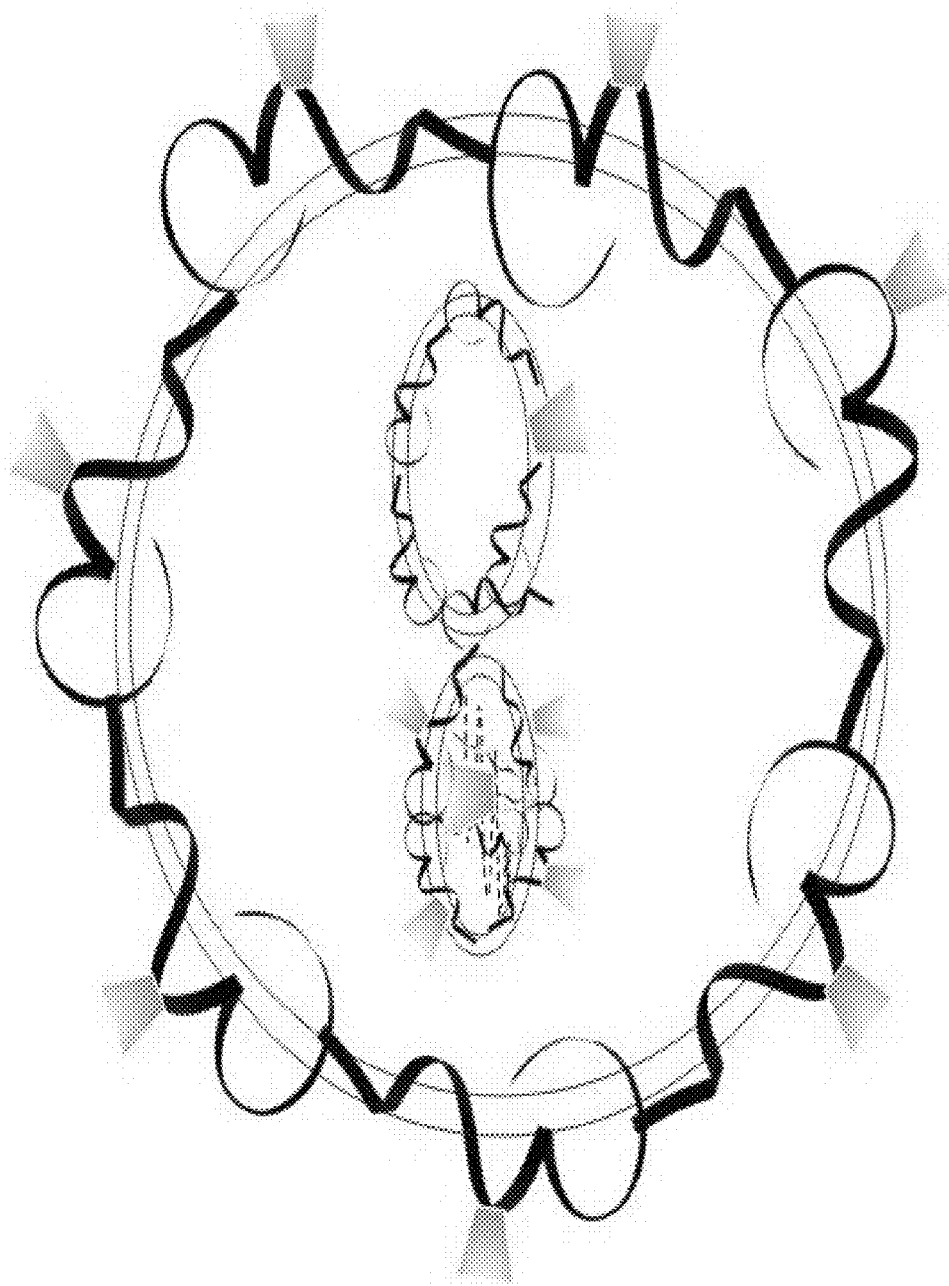

FIG. 19 refers to an enlarged top view of the superconducting membrane of activated protein MMP-2 Device 3.

Figure 20:
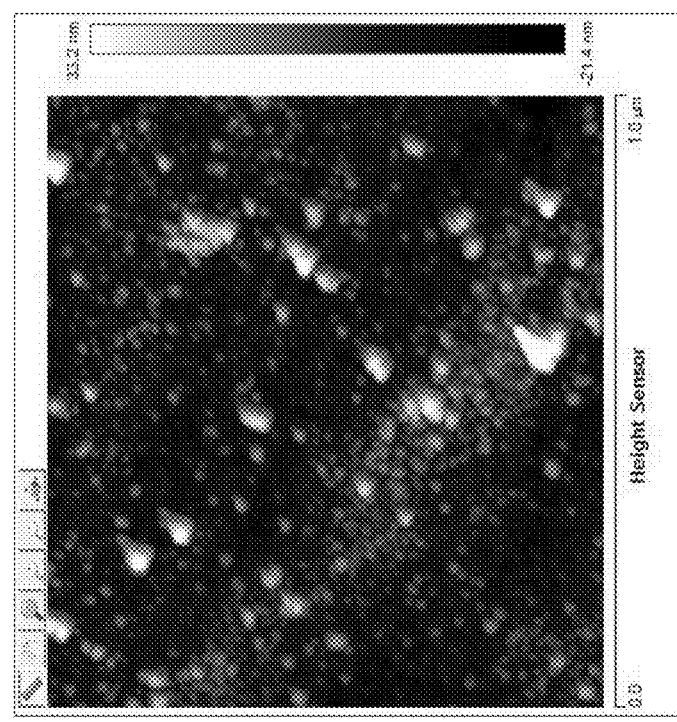

FIG. 20 refers to the 2D AFM image of the Device 1's superconducting membrane with the zinc atoms in white color; the Cooper pair electron cloud moves toward the same direction.

Figure 21:
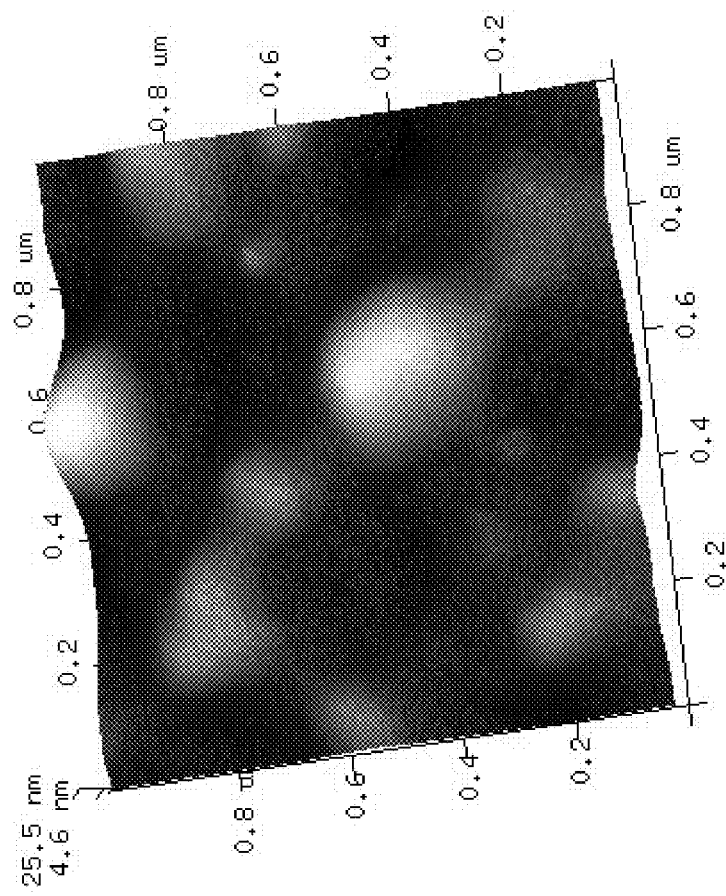

FIG. 21 depicts the 3D AFM image of the protein MMP-2 membrane with superlattice matrix of the Device 3. Zinc atoms are either along with the toroidal rings or on the top of the ring.

Figure 22C:
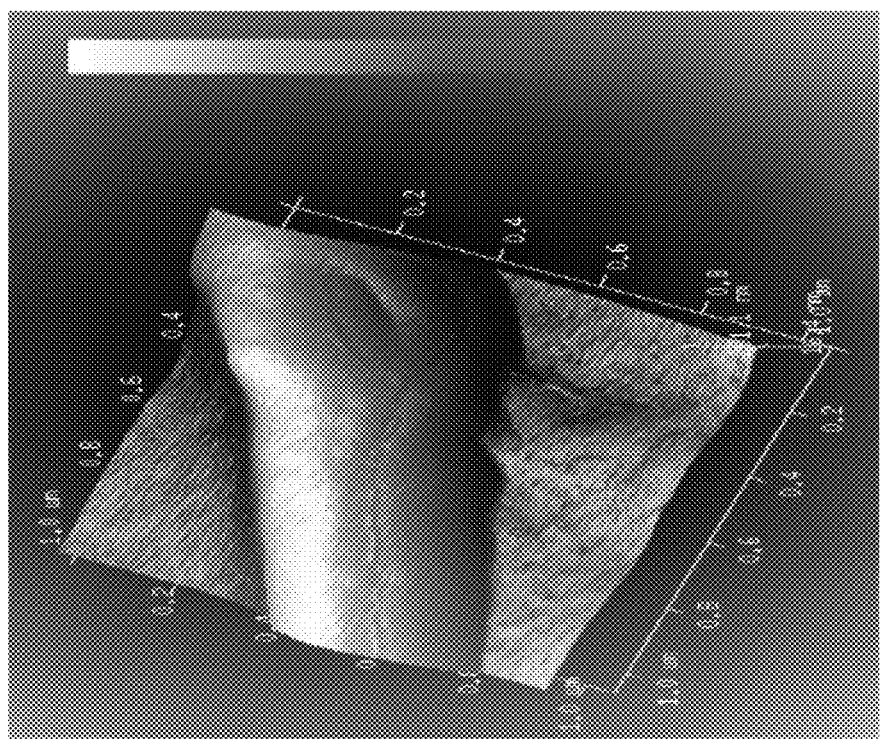
Figure 22B:
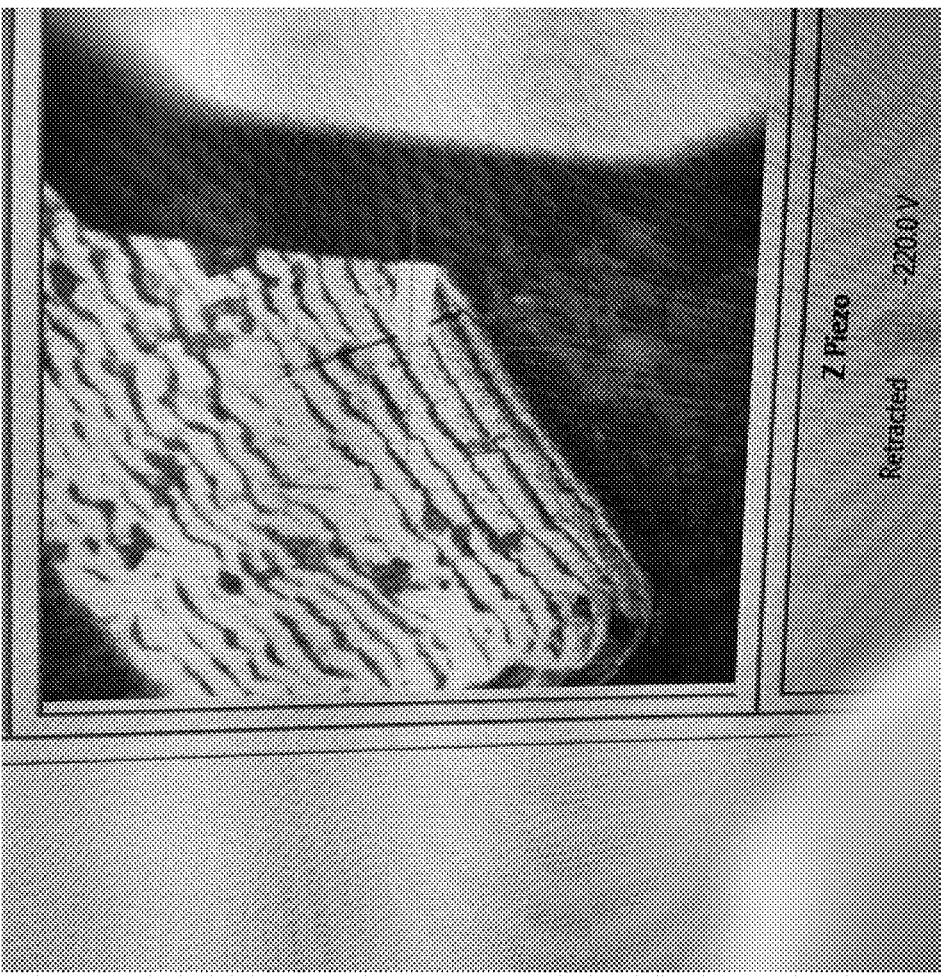
Figure 22E:
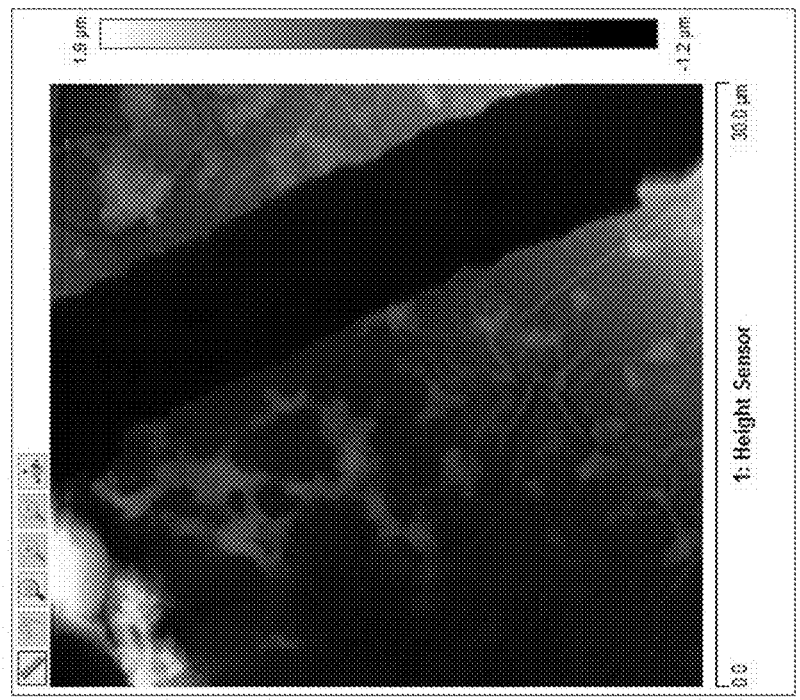
Figure 22D:
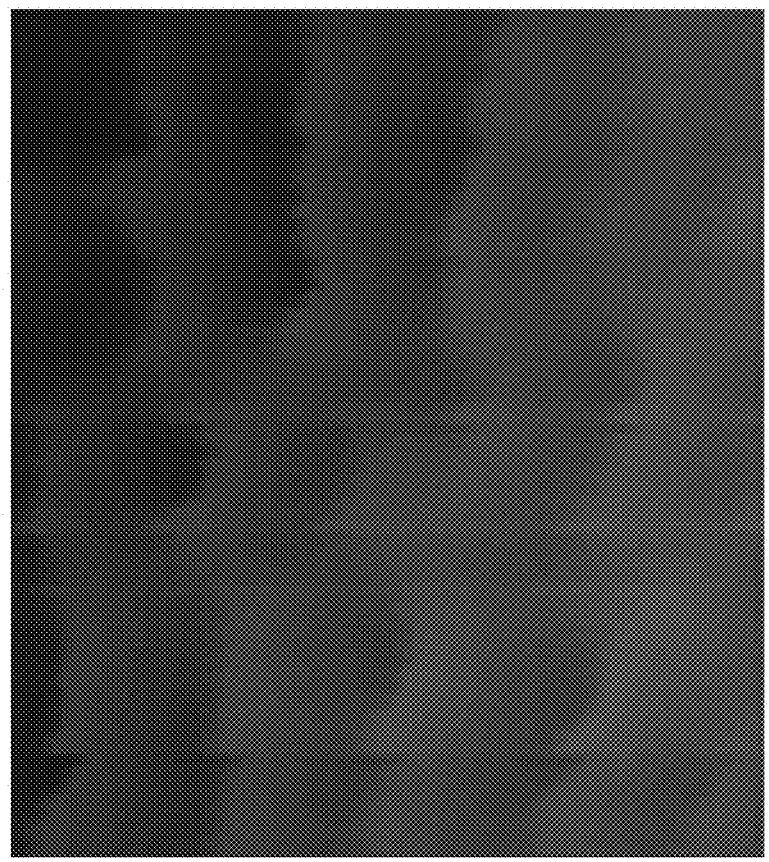
Figure 22G:
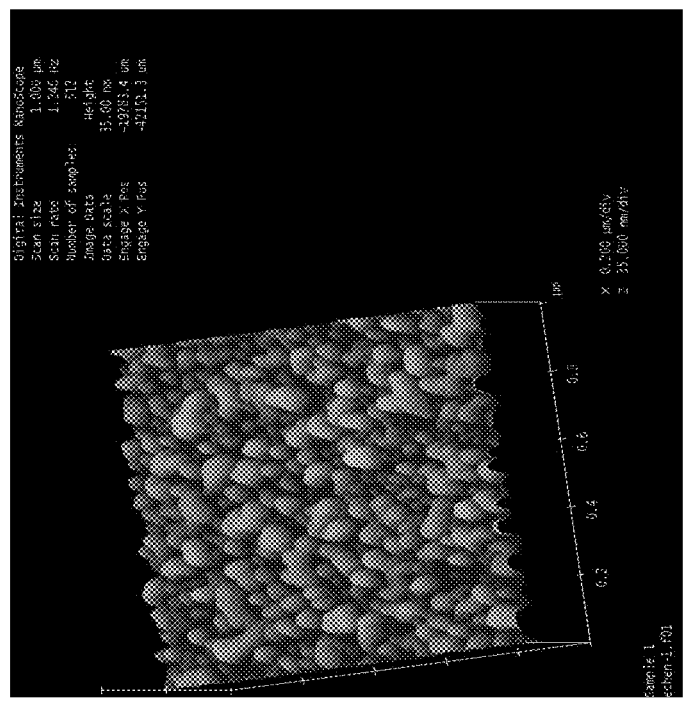
Figure 22F:
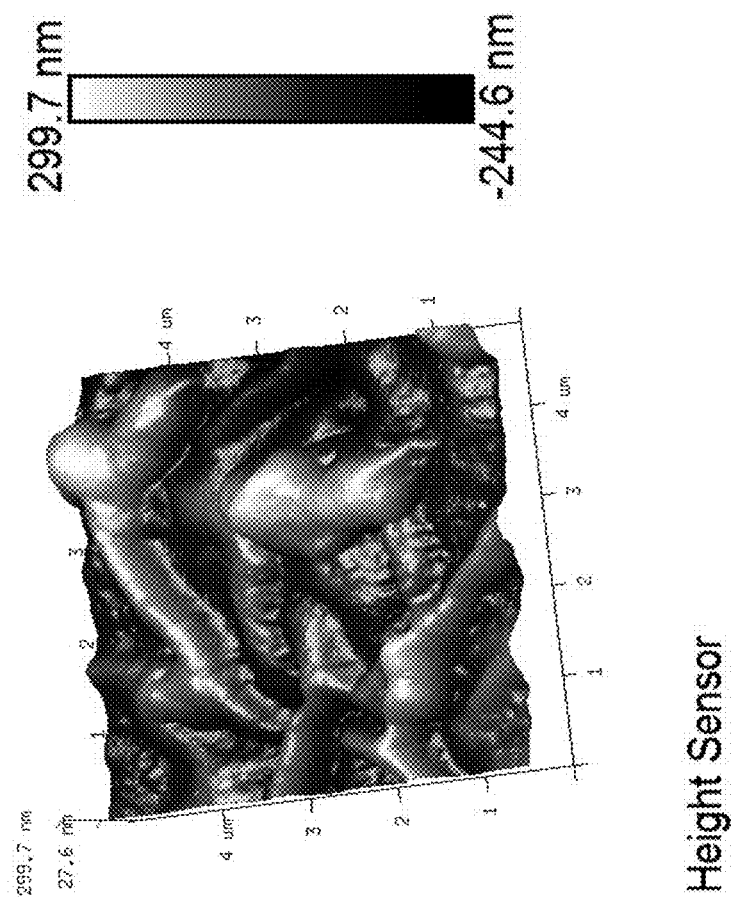

FIG. 22A depicts the 2D image in a bird-eye-view of the superlattice superconducting membrane with curvature nanotubes and the zinc atoms are served as the junction of Device 2 in a sensor mode with cross-section analysis in 5 μm×5 μm; FIG. 22B is the photo image structure of the whole SAM superconductive multiple layers membrane on the screen during setting the probe before taken an AFM image. FIG. 22C is a 3D image of the curvature single-wall nanotube with zinc atom on top; FIG. 22D depicts the 2D image of the multiple waves formed in the carnal in the membrane of Device 2 with the carnal location near the cross in FIG. 22B. FIG. 22E depicts the deep carnal with superlattice on the top surface. FIG. 22F depicts the 3D bird-view of the superlattice of Device 2. FIG. 22G depicts the first layer nanoisland membrane on the gold chip, before the depositing other mixture solution.

Figure 23B:
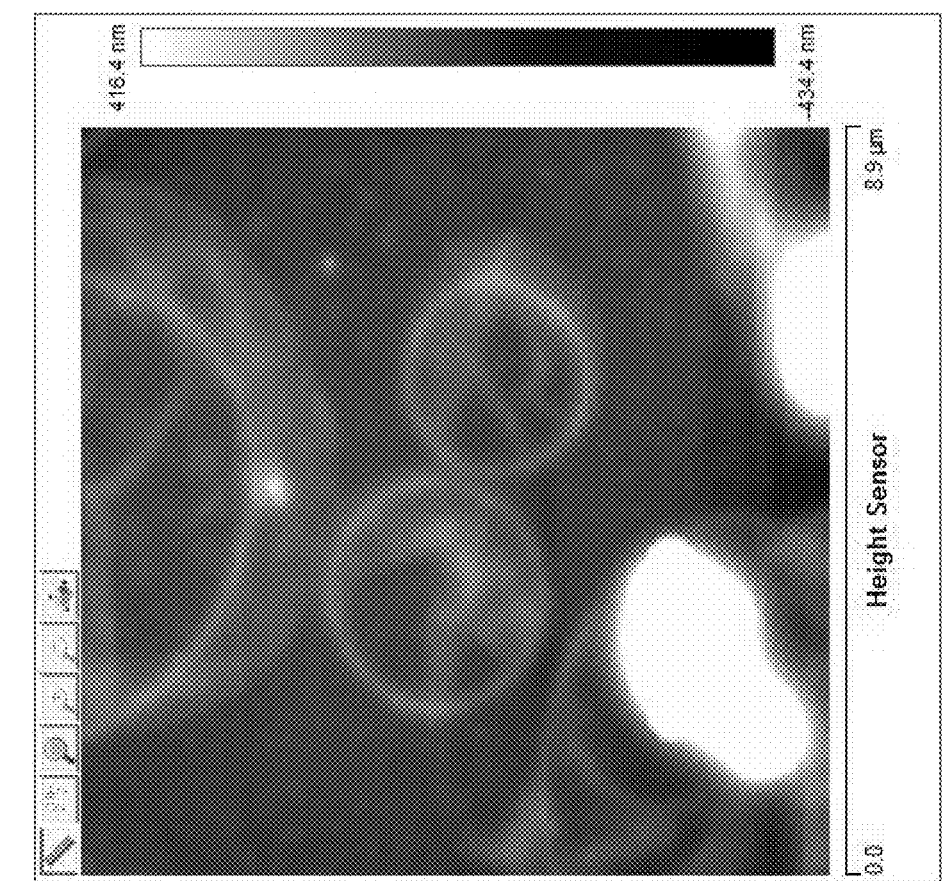
Figure 23A:
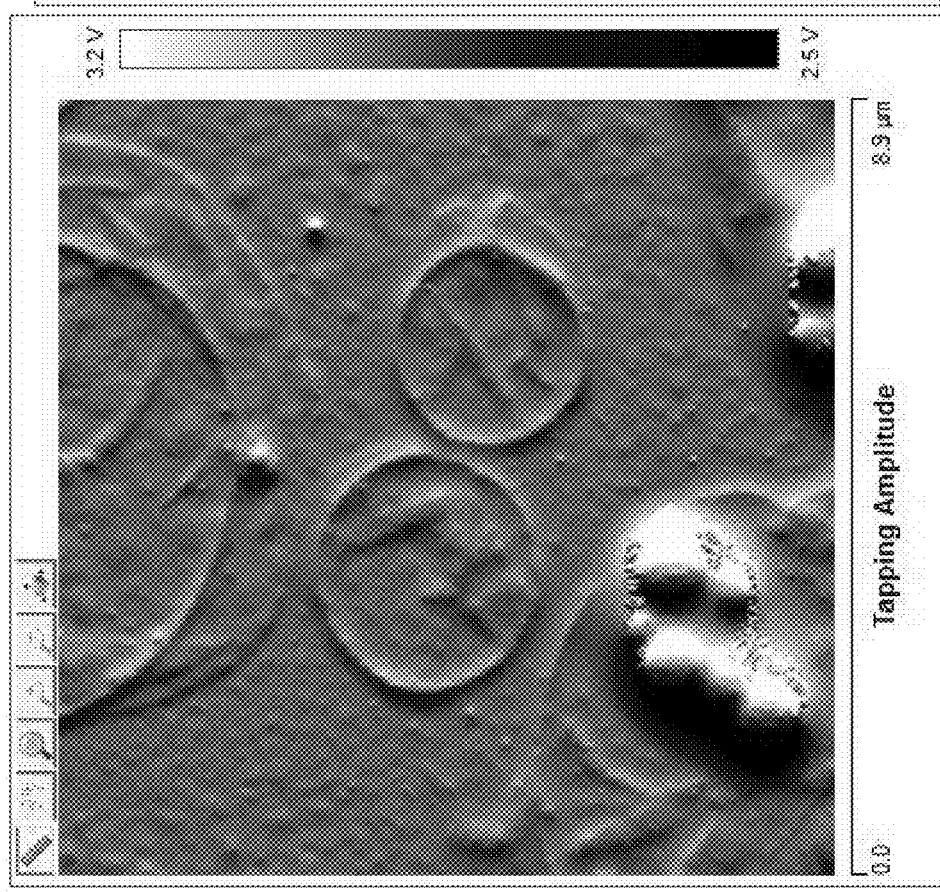

FIG. 23A and FIG. 23B depict the native MMP-2 Device 3's circular structures with zinc atoms with the tapping mode for detail shown the zinc atoms in the native MMP-2 protein membrane and in sensor mode, respectively in 10 μm×10 μm.

Figure 24A:
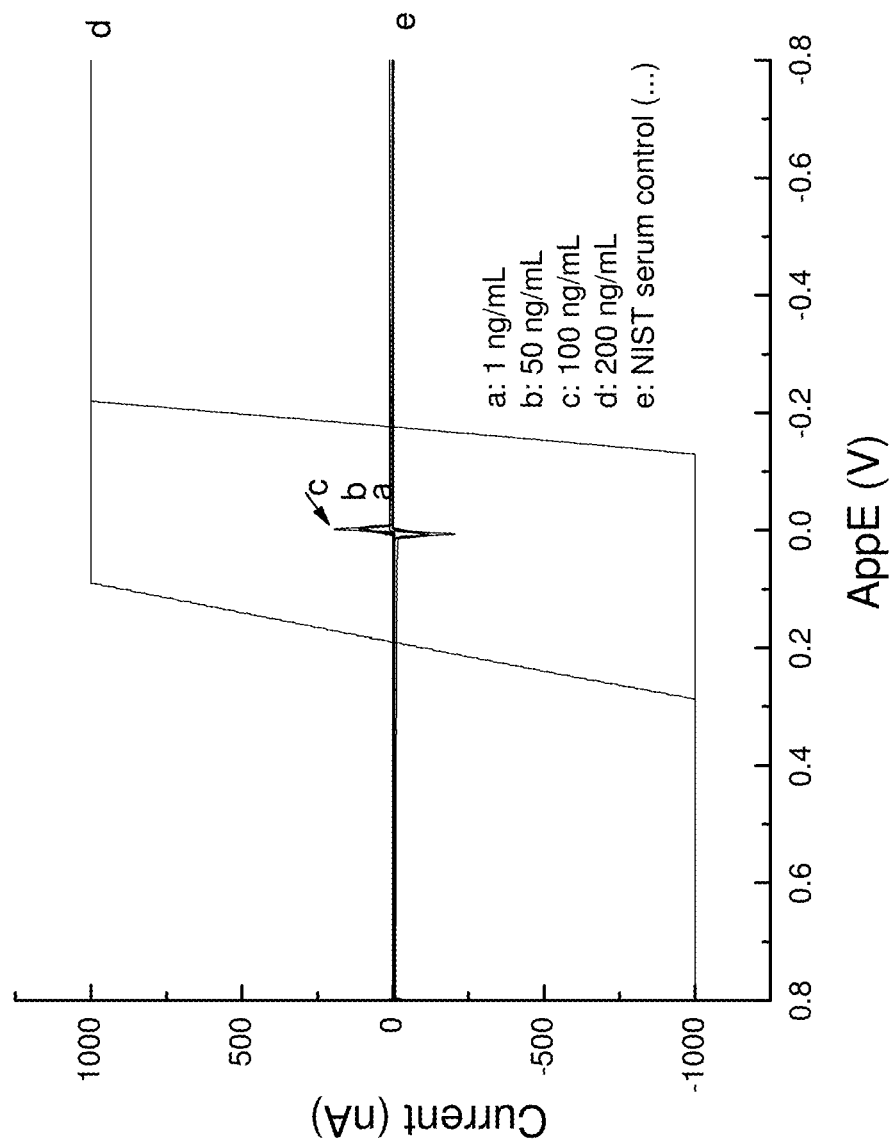
Figure 24C:
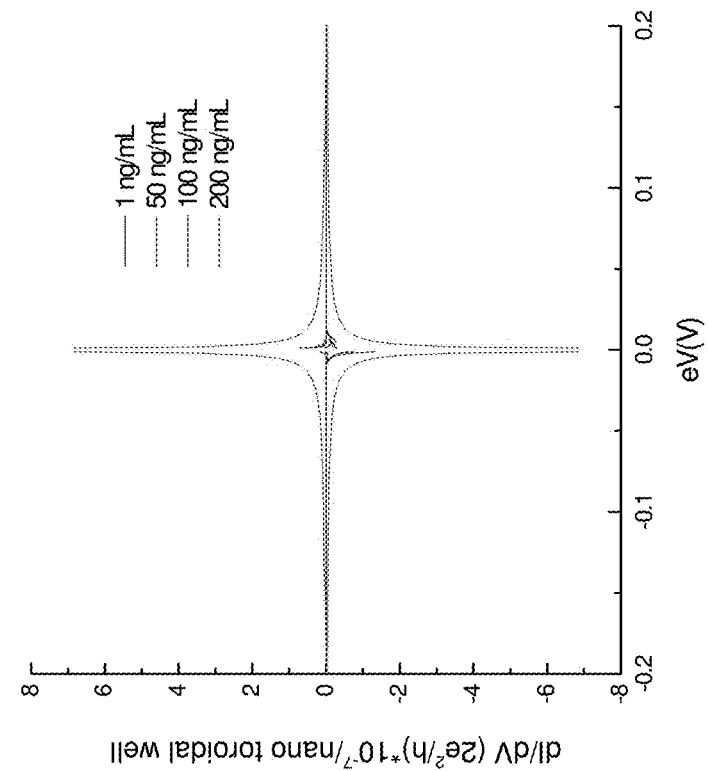
Figure 24B:
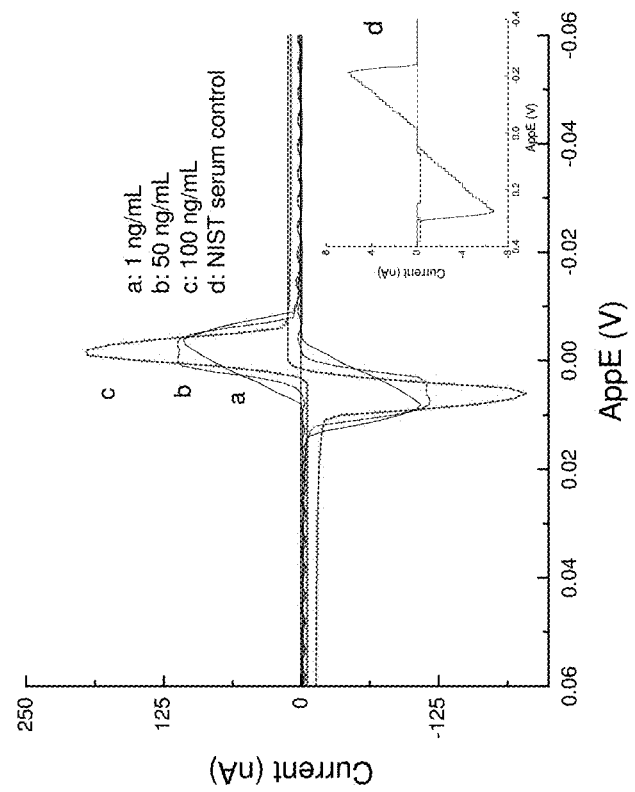

FIG. 24A depicts the i-V curves of super JJ current intensity in various collagen concentration at 300 Hz scan rate in NIST human serum with B=0. FIG. 24B depicts an enlarged view of the plots and the insert is the control of human serum. FIG. 24C depicts the curves in superconductive density of dI/dV ($2e^2/h$) per nano toroidal well vs. applied potential at zero-bias for Device 1.

Figure 25B:
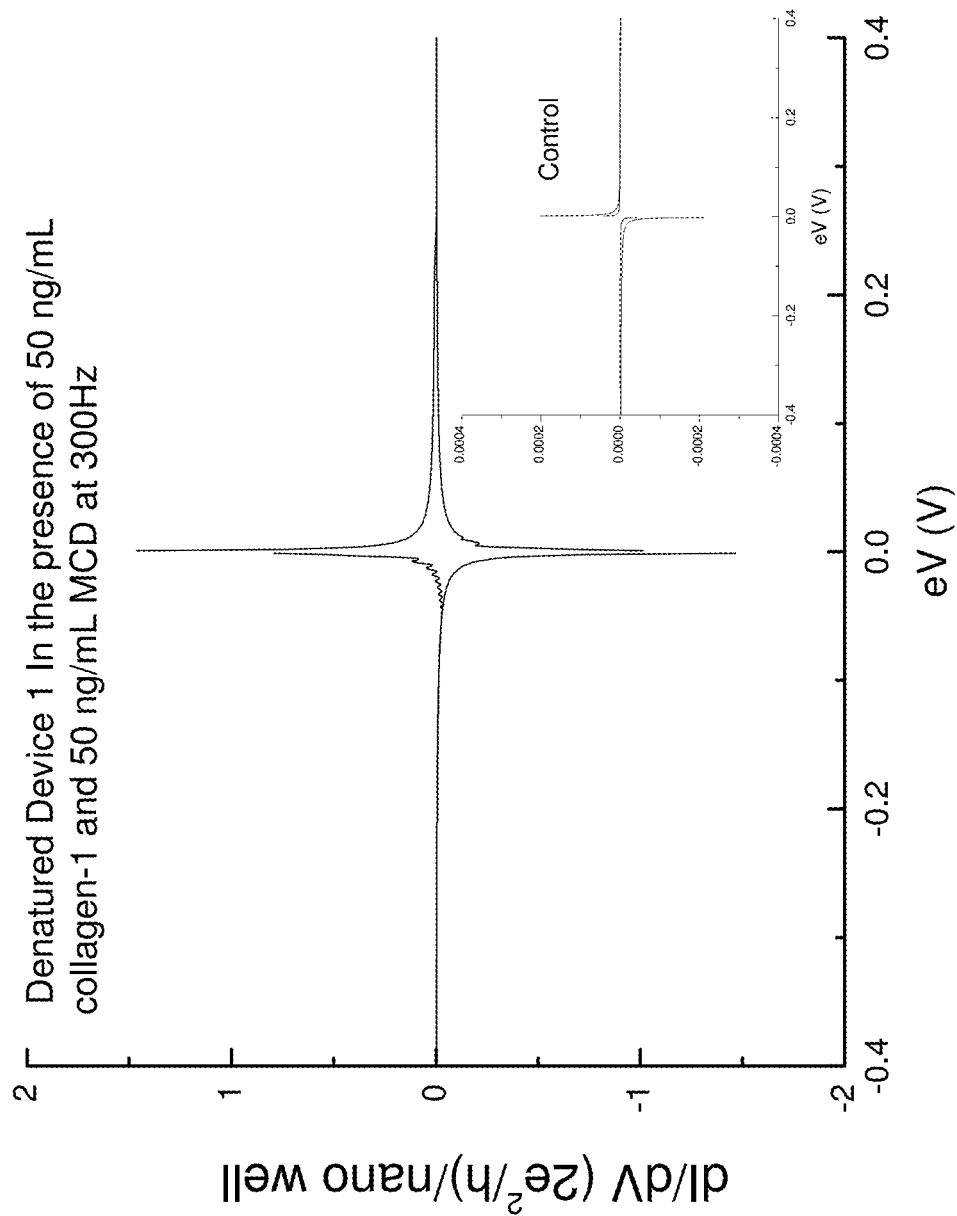

FIG. 25A depicts the denatured Device 1's i-V curve at spiked 50 ng/mL collagen-1 and 50 ng/mL MCD in the PBS solution. Insert is the controls. FIG. 25B depicts the superconductive density curve of dI/dV ($2e^2/h$) per nano toroidal well at zero-bias against the control shown in the insert in the PBS solution.

Figure 26A:
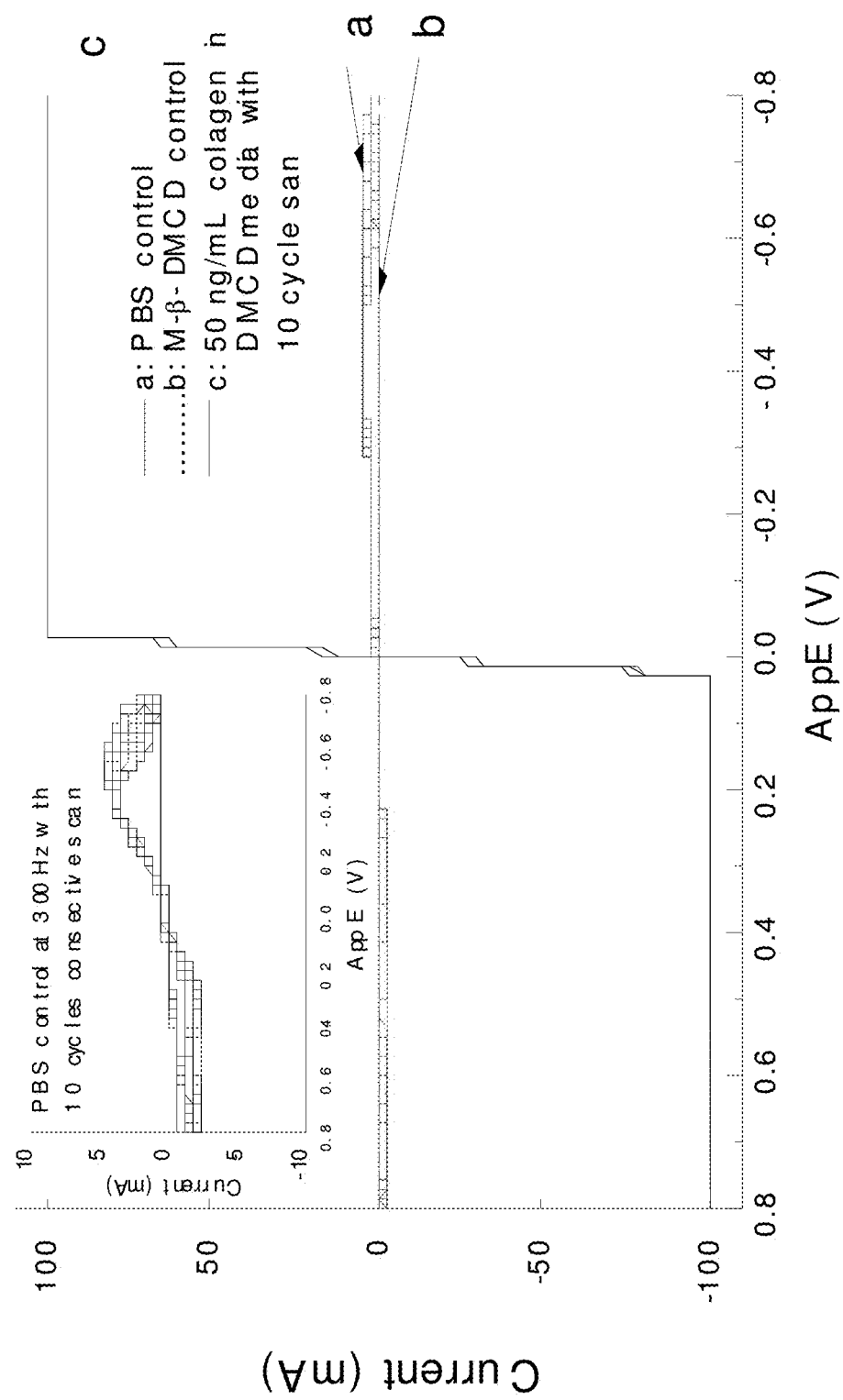
Figure 26B:
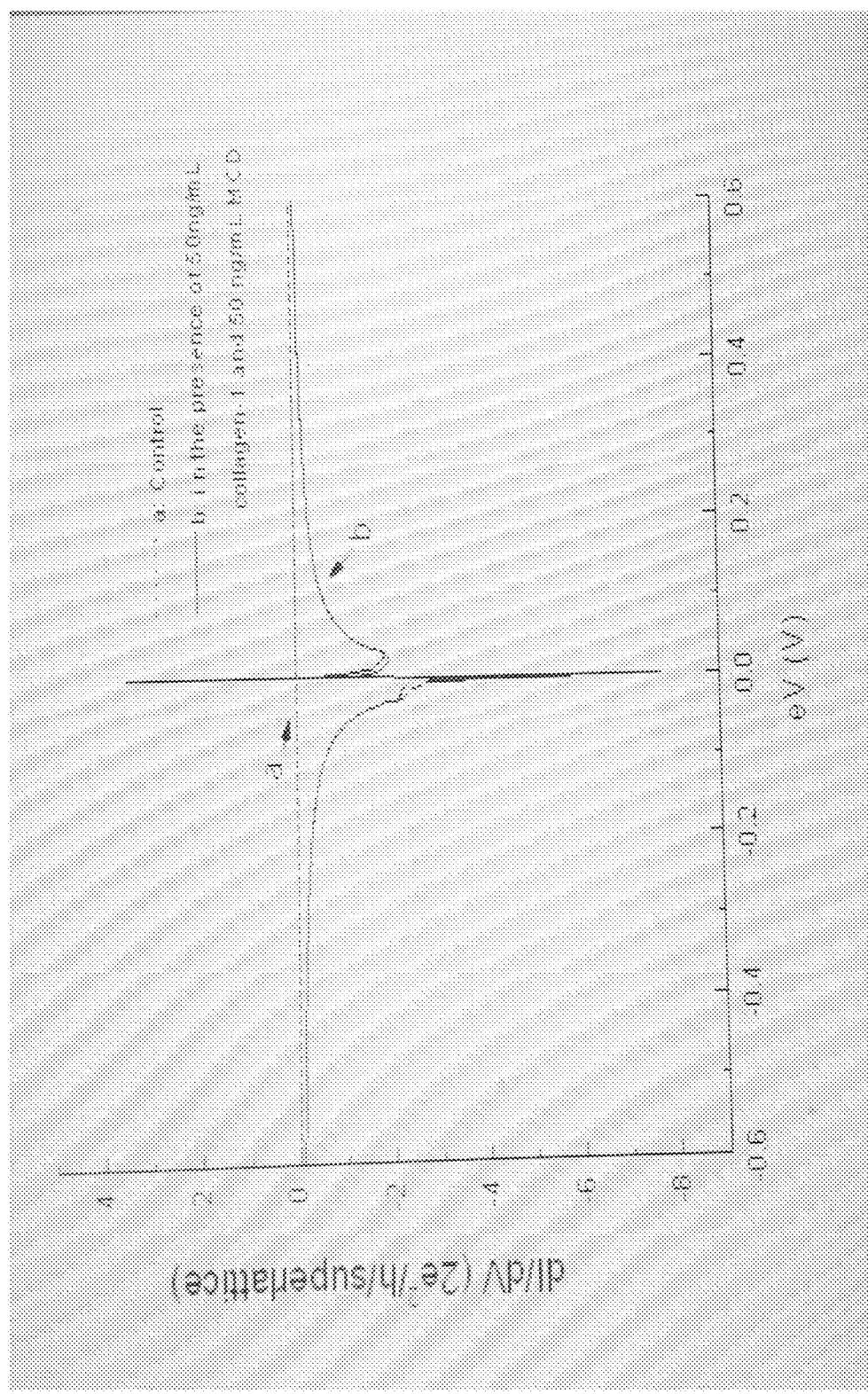

FIG. 26A depicts Device 2's superconductivity in PBS in the presence of 50 ng/mL collagen-1 and 50 ng/mL MCD compared with the controls with 300 Hz scan rate. The insert depicts the 10 cycle consecutive scans of the Device 2 in PBS solution. FIG. 26B depicts the superconductive density curves of dI/dV (2e/h) vs. per superlattice compared with that of in the control.

Figure 27B:
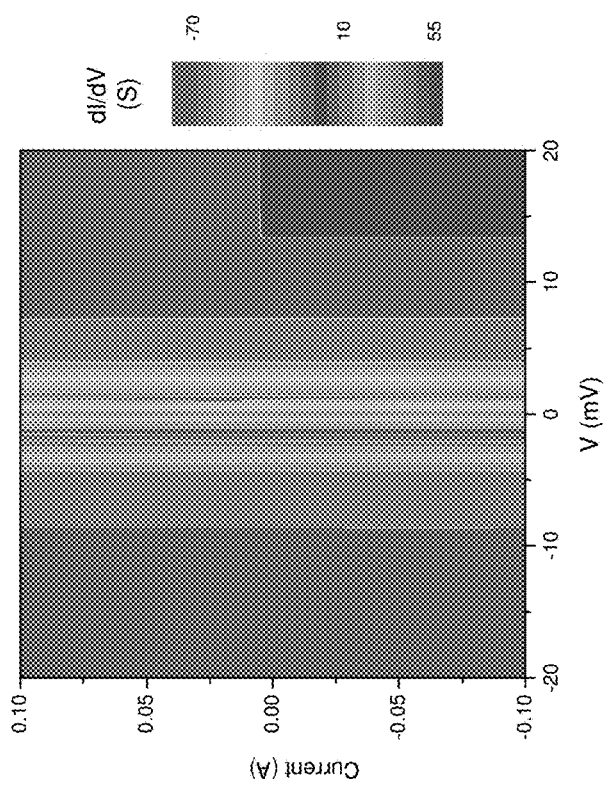
Figure 27A:
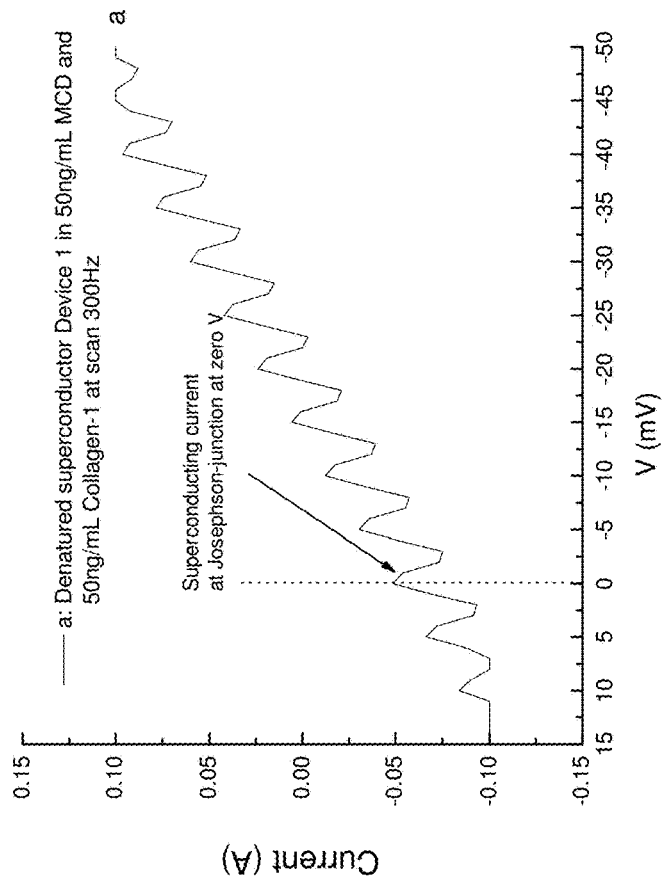
Figure 27D:
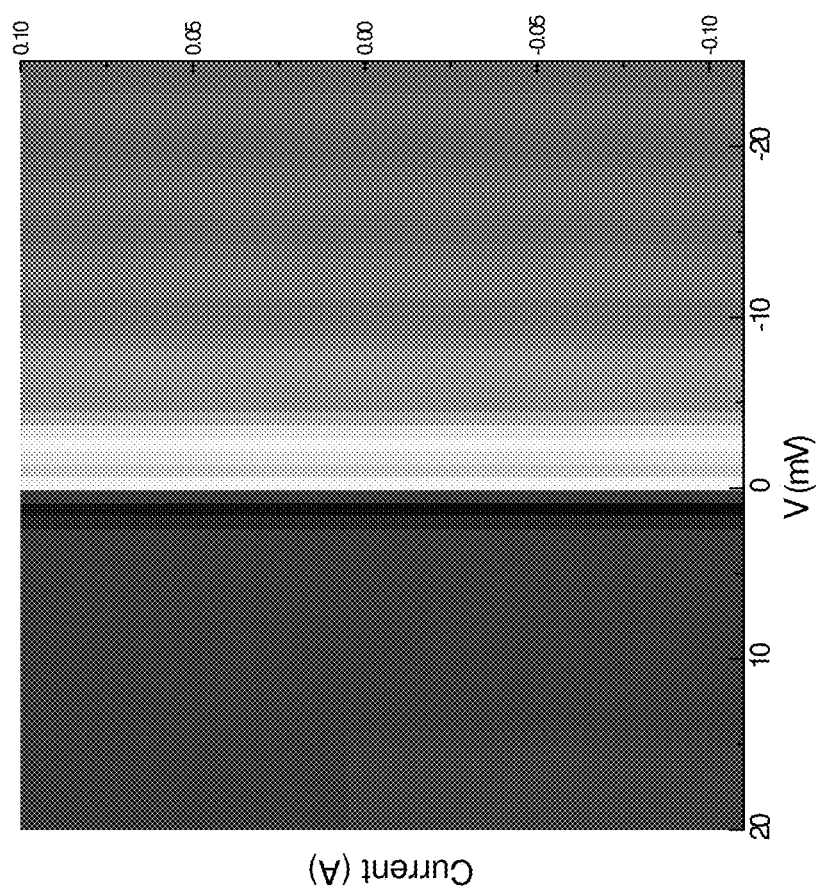
Figure 27C:
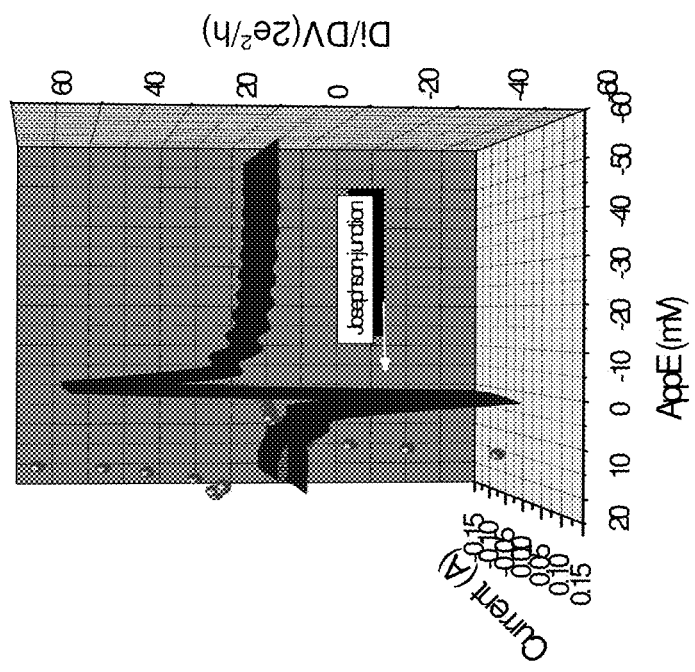

FIG. 27A depicts the zero-voltage peak of the denatured, i.e., activated Device 1 from the i-V curve in the presence of 50 ng/mL collagen-1 and 50 ng/mL MCD in PBS 7.4 solution at scan rate 300 Hz over 15 mV to −50 mV. The i-V curve came from FIG. 25A. FIG. 27B depicts the contour map of the special trajectory of the superconductive band of ±70 Siemens (S) vs. supercurrent in the range of ±100 mA and in the potential range over 20 mV to −25 mV. FIG. 27C depicts the 3D special location of the zero-voltage peak vs. supercurrent and vs. potential between 20 mV and −60 mV. FIG. 27D depicts the image of the brightest wide superconducting energy bands at the zero-bias of the activated Device 1 for the coherent Cooper-pair and also shows the single-electron tunneling bands in deemed light under an external magnetic field=0 condition.

Figure 28A:
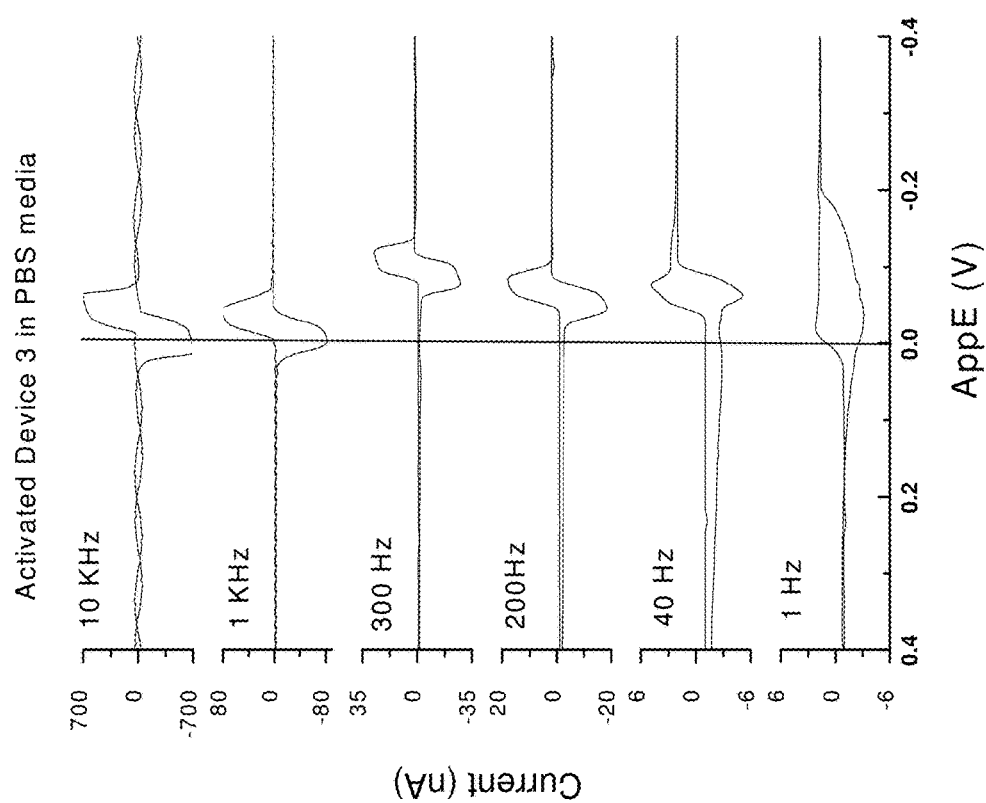
Figure 28B:
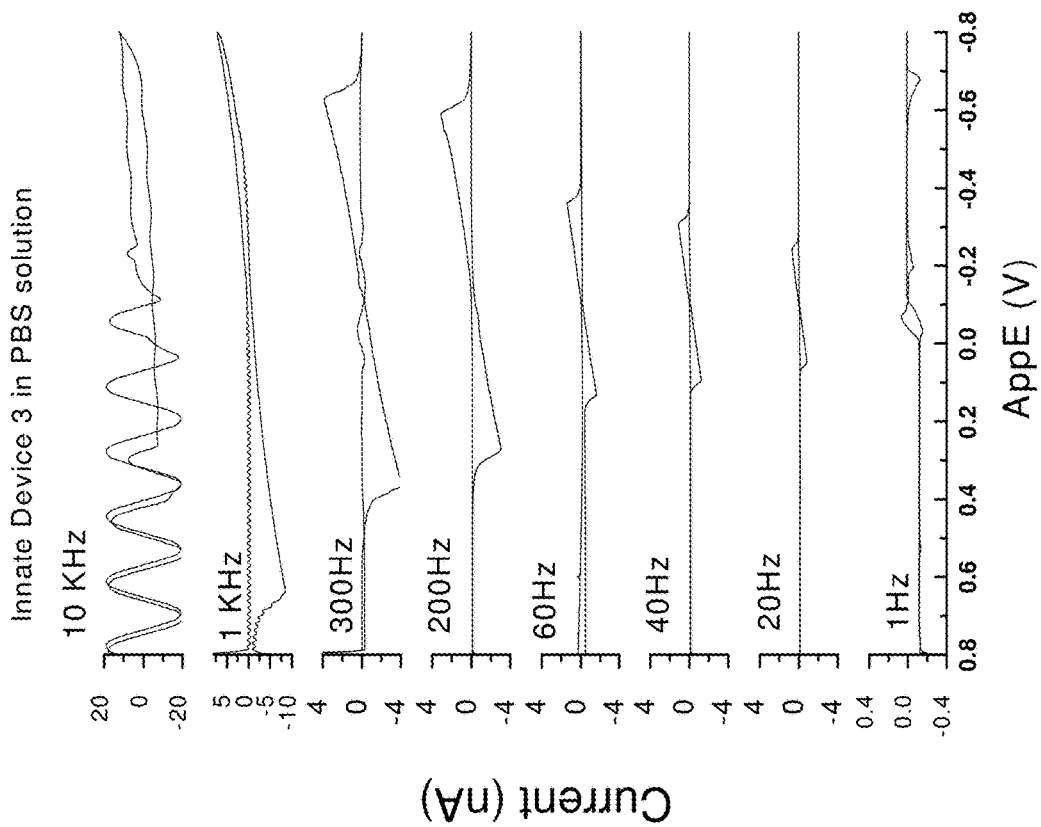
Figure 28D:
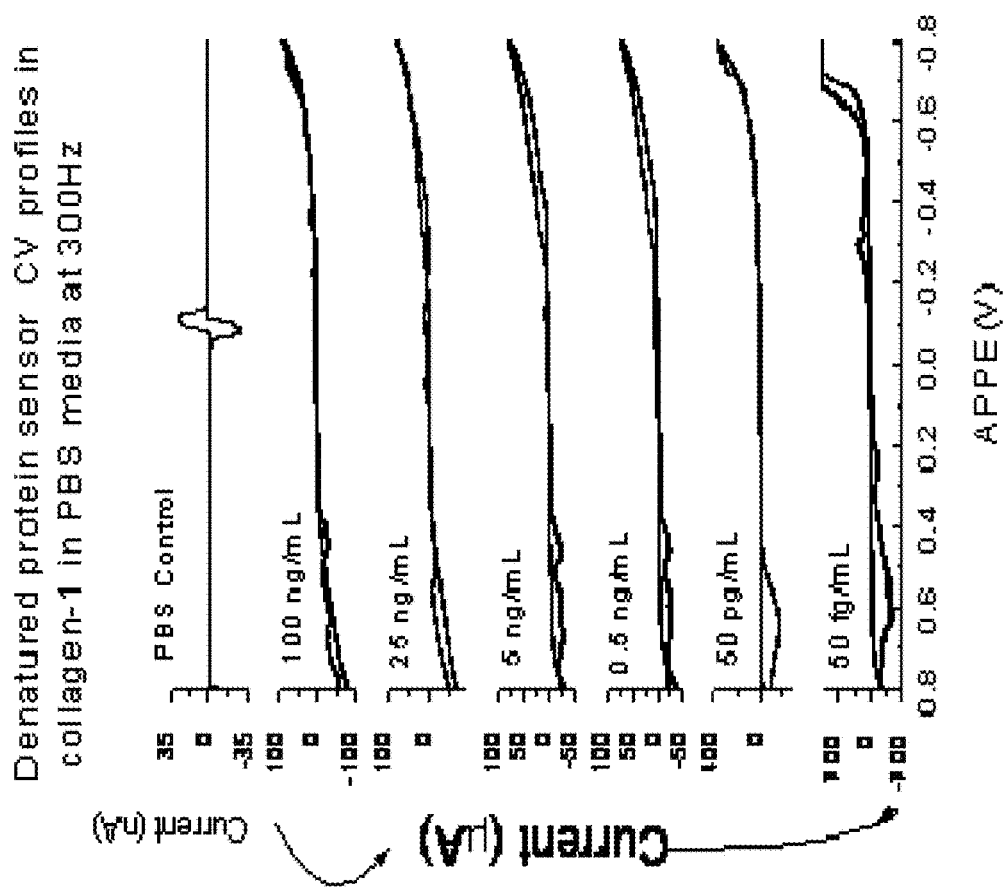
Figure 28C:
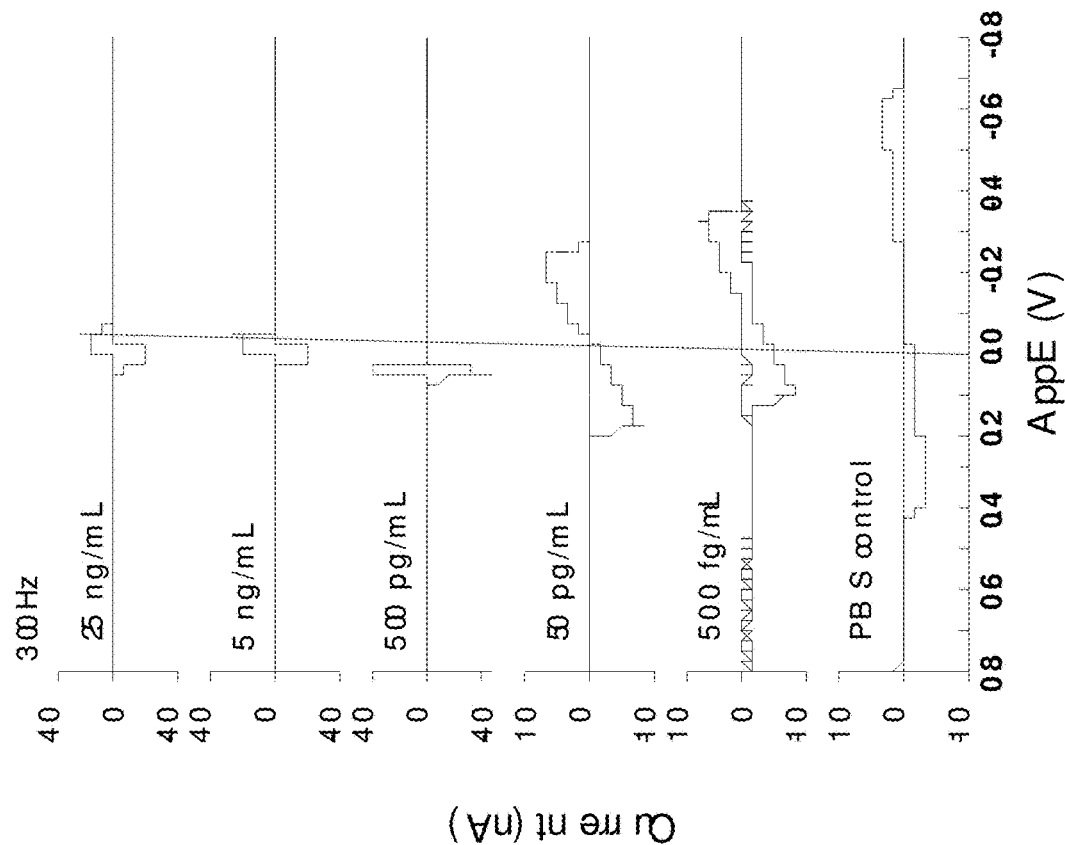
Figure 28E:
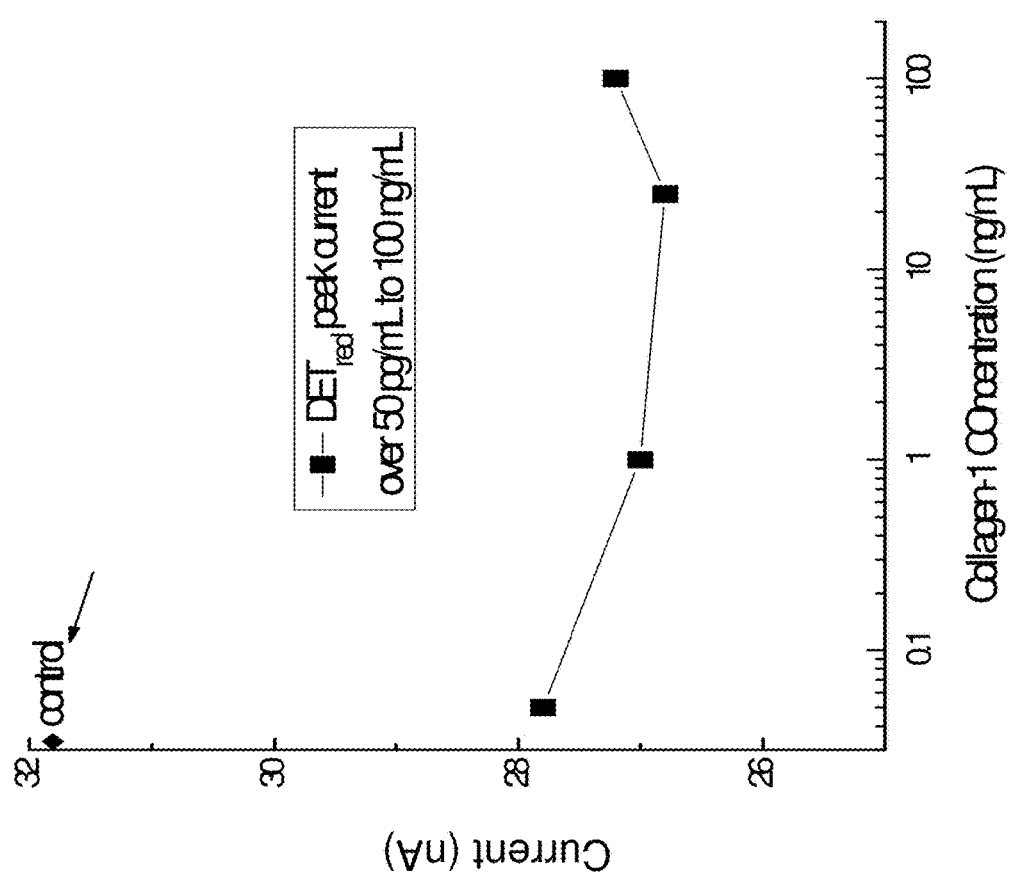
Figure 28F:
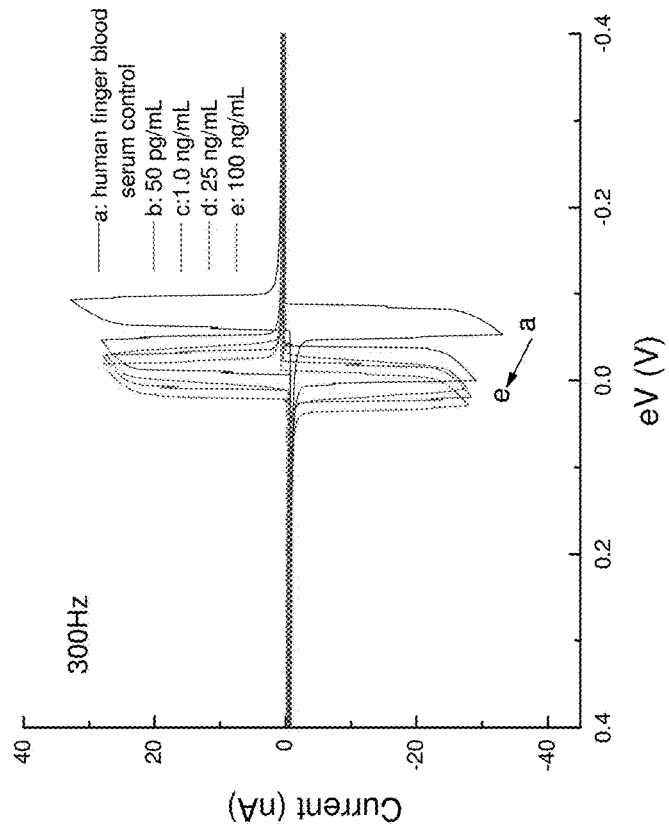
Figure 28G:
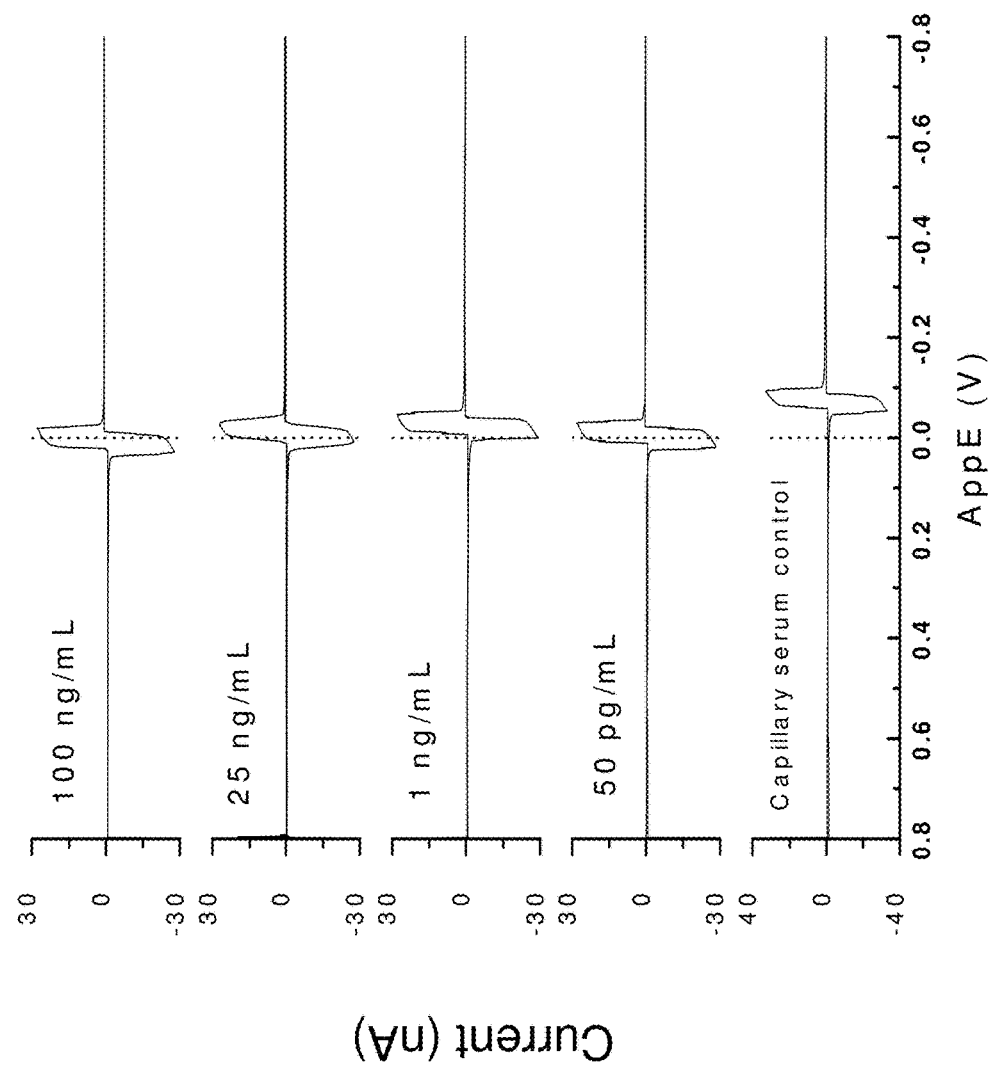

FIG. 28A depicts i-V profiles of the innate Device 3 in PBS solution with scan rate from 1 Hz to 10 kHz. FIG. 28B depicts i-V profiles of the activated protein Device 3 in PBS solution over 1 Hz to 10 kHz. FIG. 28C depicts the i-V profiles of the innate Device 3 in the presence of various collagen-1 concentrations from 500 fg/mL to 25 ng/mL compared with the PBS control solution at 300 Hz scan rate. FIG. 28D depicts the i-V profiles of the activated Device 3 in the presence of various collagen-1 concentrations from 500 fg/mL to 25 ng/mL compared with the PBS control solution at 300 Hz. FIG. 28E depicts the i-V profiles of the activated Device 3 with or w/o spiking collagen-1 in human capillary blood serum at scan rate 300 Hz. FIG. 28F depicts the current decay curve vs. collagen-1 concentration from 50 pg/mL to 100 ng/mL compared to control of the human capillary blood serum sample. FIG. 28G depicts the detail view of the i-V curve profiles of the zero-bias peak with the vertical dotted line having the collagen-1 concentration effects on current for the activated Device 3 in human capillary blood samples based on FIG. 28E. FIG. 28H depicts the oscillation zero-voltage peaks of the activated Device 3 in PBS control solution at 1 Hz, 1 kHz, 10 kHz, respectively. FIG. 28I depicts the trends of the supercurrent of $DET_{red}$, $DET_{ox}$ vs. scan frequencies between activated Device 3 in PBS solution compared with the innate state over scan rate 1 Hz to 10 kHz.

Figure 29A:
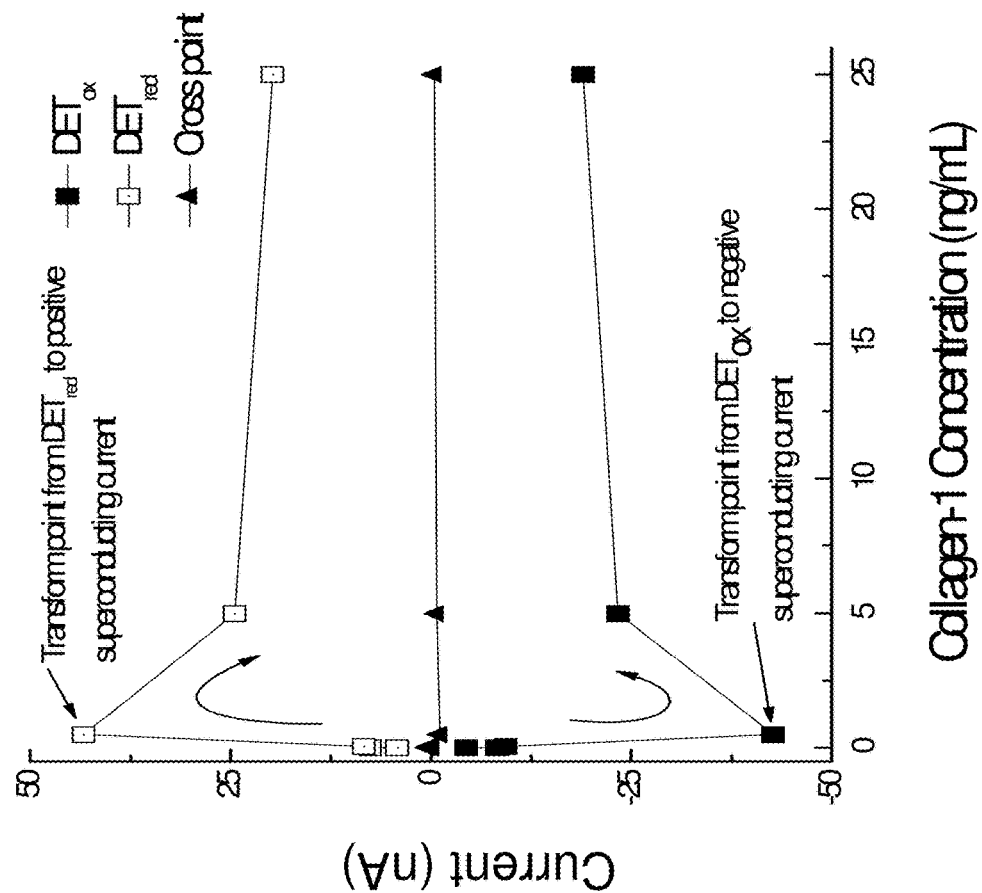
Figure 29B:
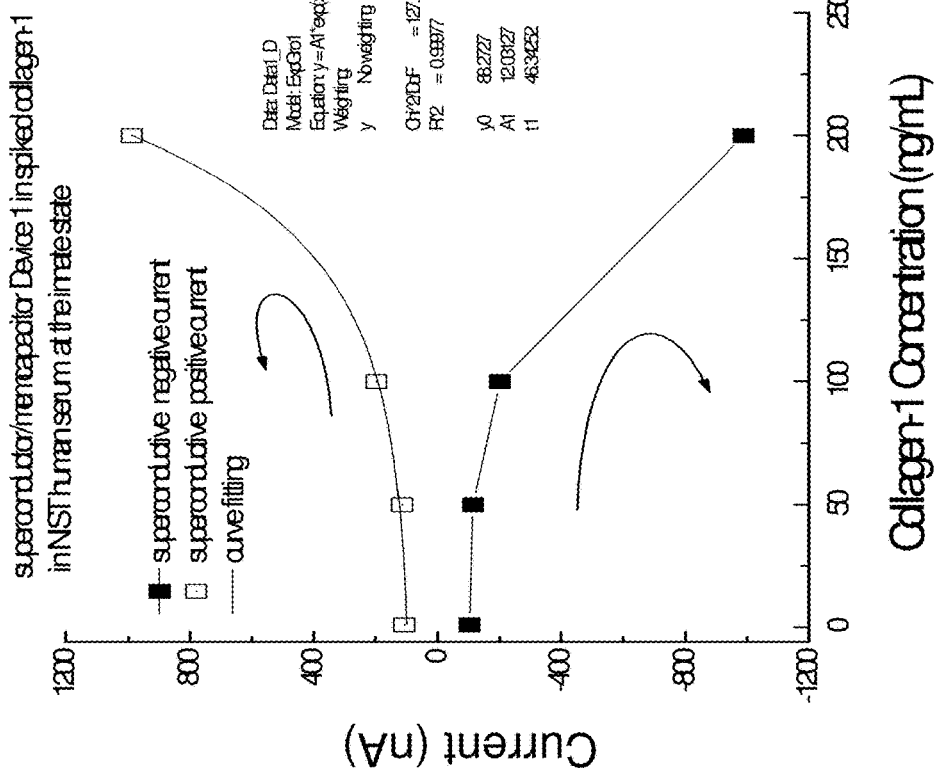

FIG. 29A depicts the exponential JJ super current vs. collagen-1 concentrations curves over 1 ng/mL to 200 ng/mL of $DET_{red}$ and $DET_{ox}$ peaks of Device 1 at the innate state at 300 Hz scan rate using NIST human serum samples. FIG. 29B depicts the trends of current vs. collagen-1 concentrations curves over 0.5 pg/mL to 25 ng/mL of the innate Device 3 in PBS solution at 300 Hz. The transform points from memristive to superconductive peaks are shown according to the original CV curves in FIG. 28C. FIG. 29C depicts the trend of the potential of $DET_{red}$ and $DET_{ox}$ peaks moves as a function of concentrations of collagen-1 over 0.5 pg/mL to 25 ng/mL of the innate Device 3 according to the FIG. 28C.

FIG. 30A depicts the innate Device 1 transforms superconductivity to memristive behavior in the spiked 0.5 pg/mL collagen-1 in NIST human serum at 300 Hz at the first scan cycle with both, superconducting current and hysteresis point located at zero-potential. The insert figure shows the hysteresis point at zero-potential, while located in the superconducting band. FIG. 30B depicts the second scan cycle; FIG. 30C depicts the third scan cycle; FIG. 30D depicts the fourth scan cycle; FIG. 30E depicts the fifth scan cycle and FIG. 30F depicts the control of NIST serum sample with pure memristive characteristics.

Figure 31B:
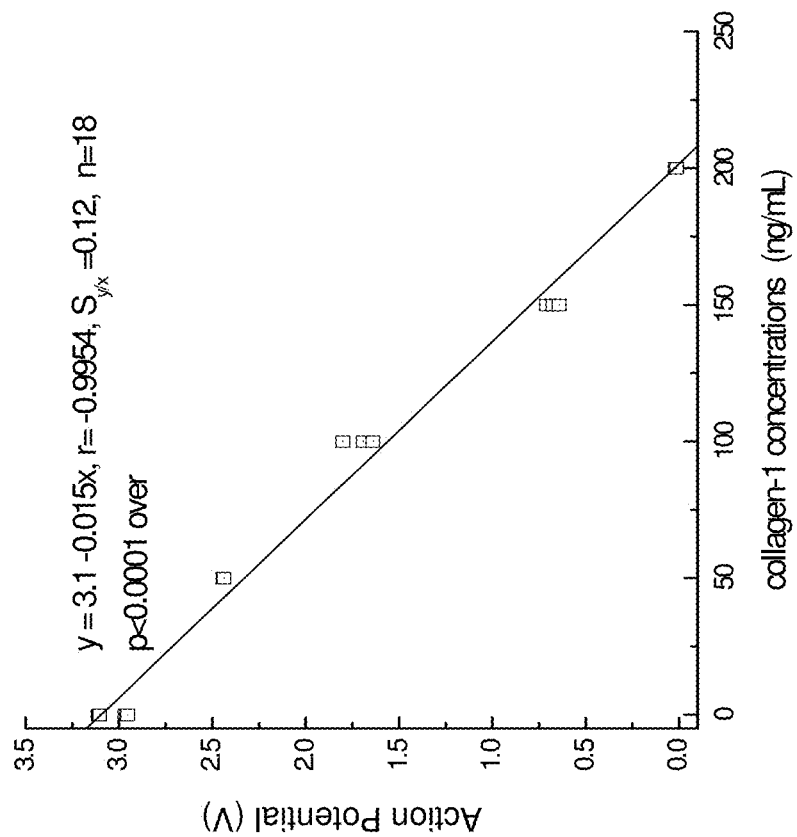
Figure 31A:
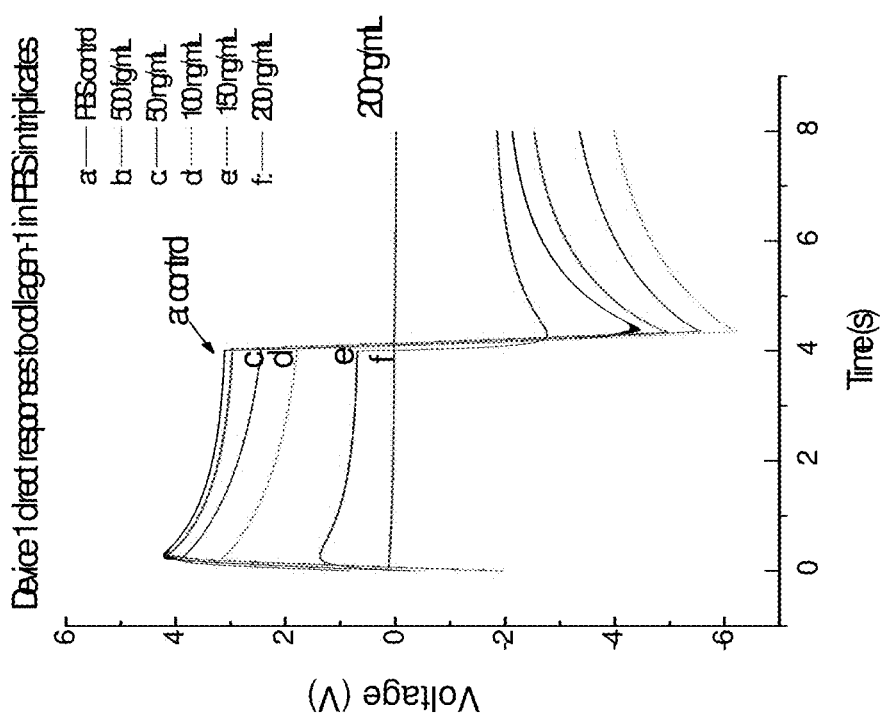

FIG. 31A depicts Device 1's voltage profiles over collagen level 0.5 pg/mL to 200 ng/mL at 0.25 Hz. FIG. 31B depicts the calibration curve. Samples run triplicates.

Figure 32B:
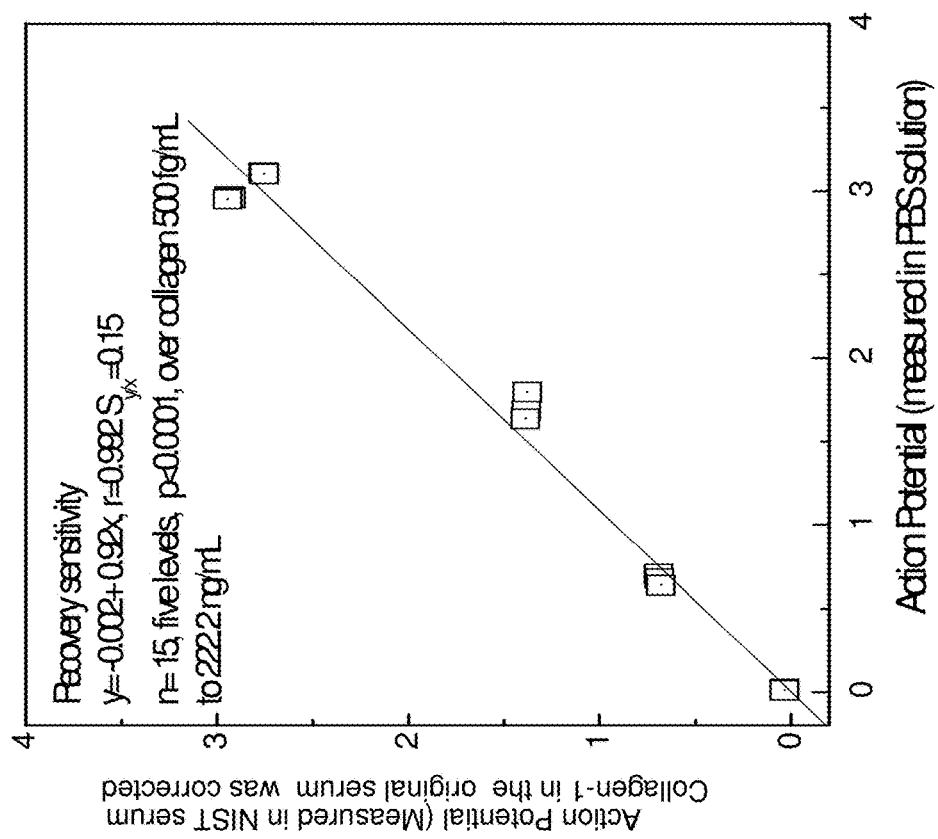
Figure 32A:
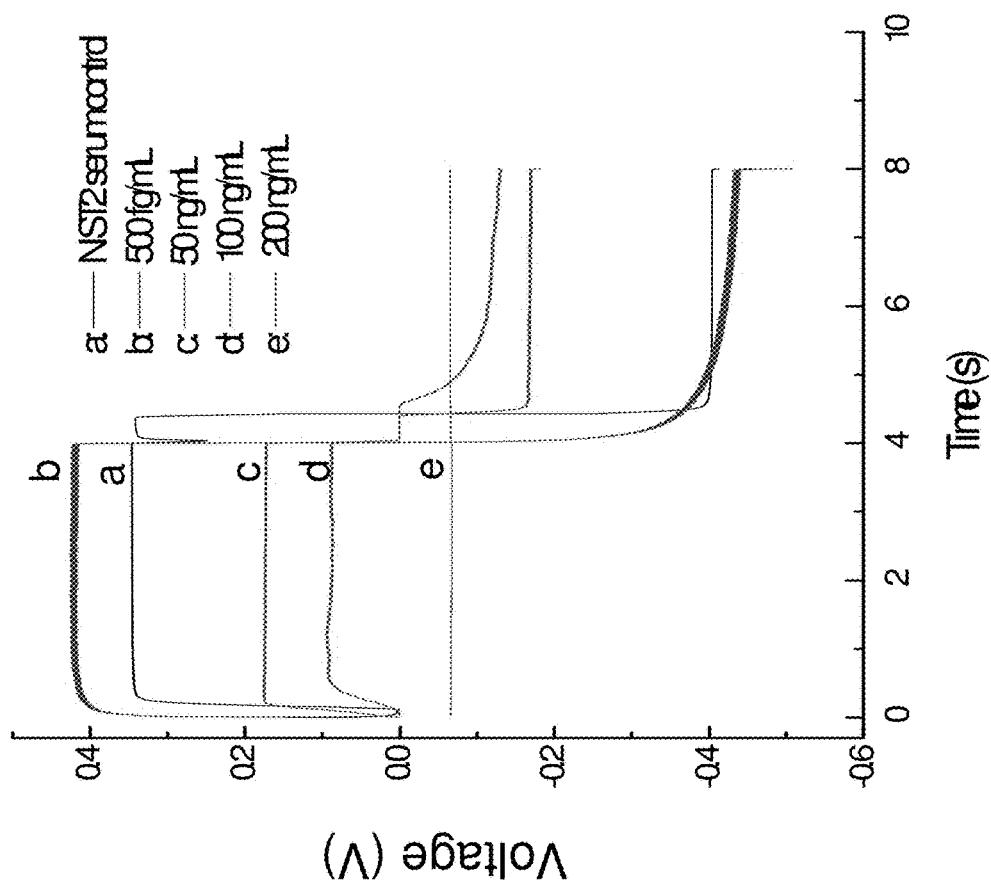

FIG. 32A depicts the voltage profiles in human serum with or w/o spiking collagen with innate Device 1. FIG. 32B depicts the linear regression curve of the measured collagen in PBS vs. that in serum after corrected the control effect before spiking.

FIG. 33A depicts the trend of the Resting potential curve vs. spiked collagen-1 concentrations in PBS solutions for innate Device 1. FIG. 33B depicts the trend of the Action potential curve vs. spiked collagen-1 concentrations and FIG. 33C depicts the energy density curve vs. collagen-1 concentrations. All samples run triplicates.

FIG. 34 depicts the AC current oscillating with a time span in 0.4 s for 4000 data points per step measurement compared among activated Device 1, Device 2 and innate Device 3 with 13 ms, 18 ms and 12 ms per peak spent for oscillation at zero potential in every step in PBS solution using the CA method.

FIG. 35A depicts DC curves vs. time under zero potential compared with Device 2 and the innate Device 3 using the DC potential amperometric method. FIG. 35B depicts DC curves vs. time under zero potential compared with Device 1 and the innate Device 3 using the DC potential amperometric method.

Figure 36:
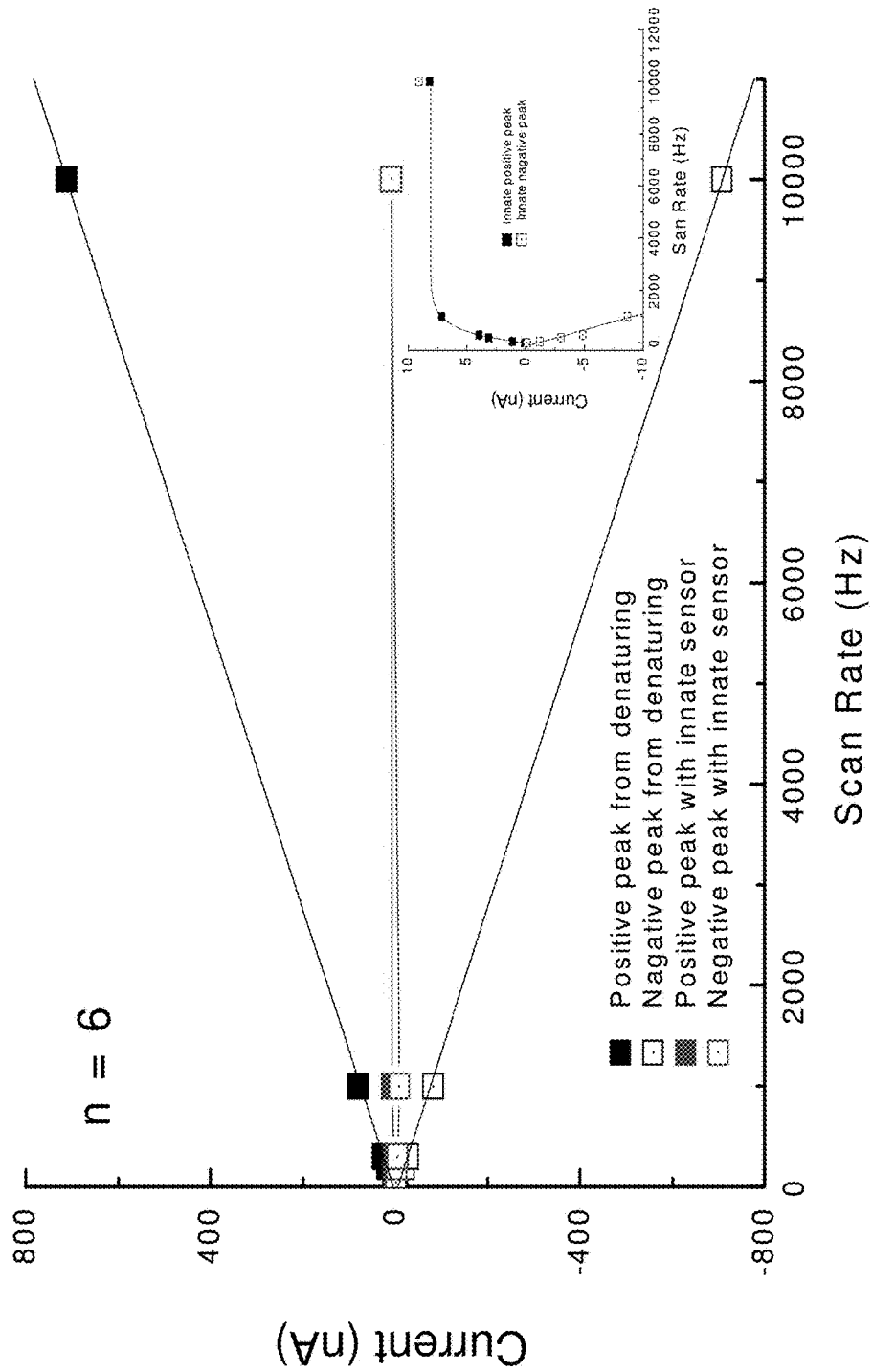

FIG. 36 depicts the curve current intensity comparison between innate and activated states for Device 3 in PBS solution vs. scan rate over 1 Hz, 40 Hz, 200 Hz, 300 Hz, 1 kHz, and 10 kHz by the CV method. The insert is the enlarged view of the innate state Device 3.

Figure 37A:
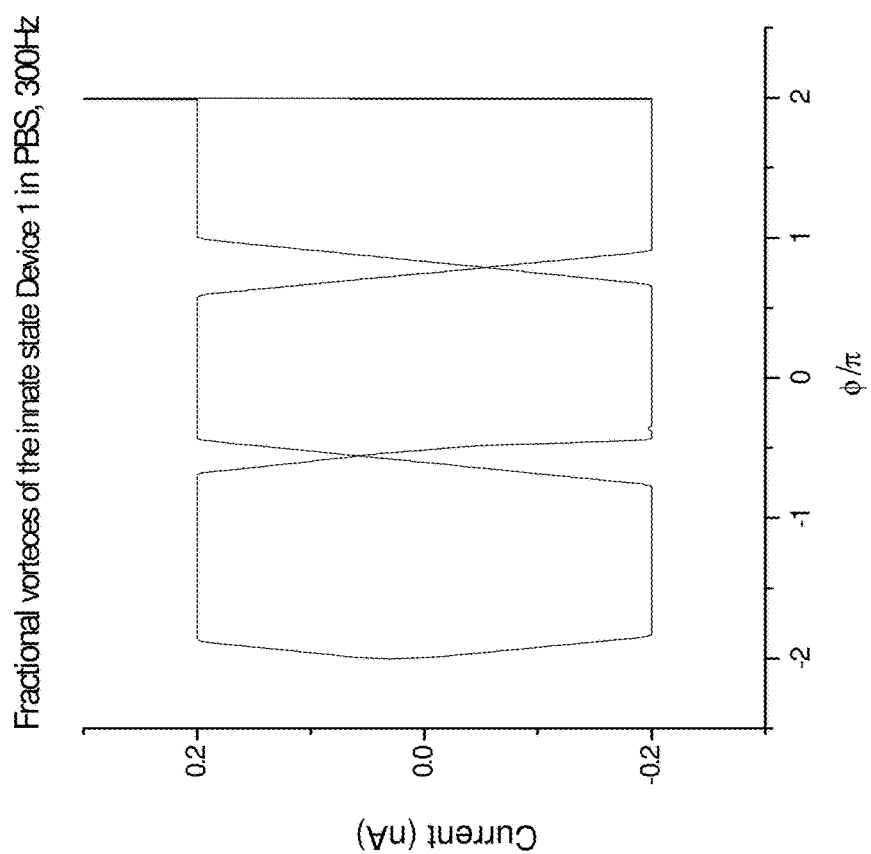
Figure 37B:
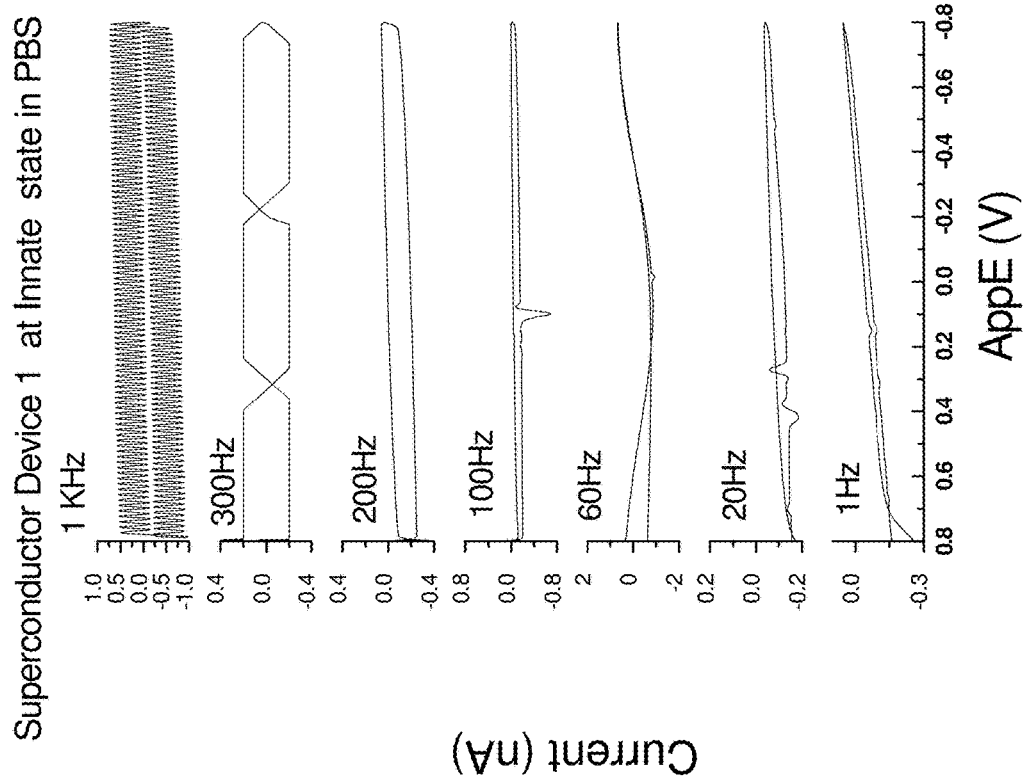

FIG. 37A depicts the phase changes of the i-V cures vs. scan rate of the innate state Device 1 in PBS solutions. FIG. 37B depicts the fractional phase changes of the innate state Device 1 in PBS solution at 300 Hz.

Figure 38C:
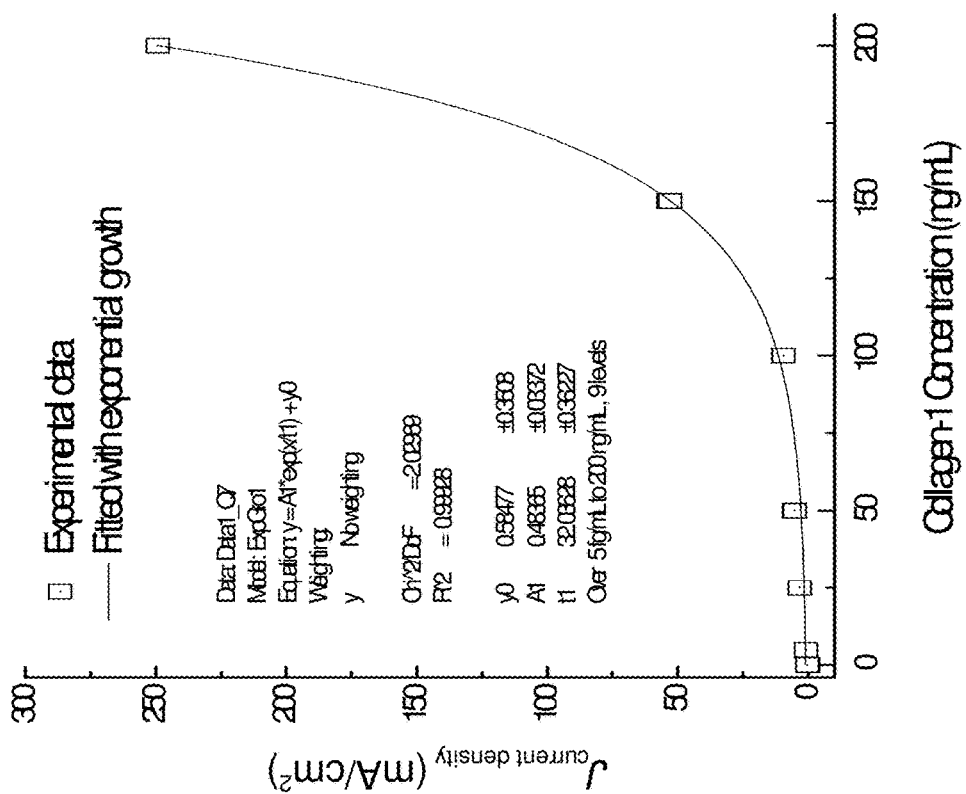
Figure 38B:
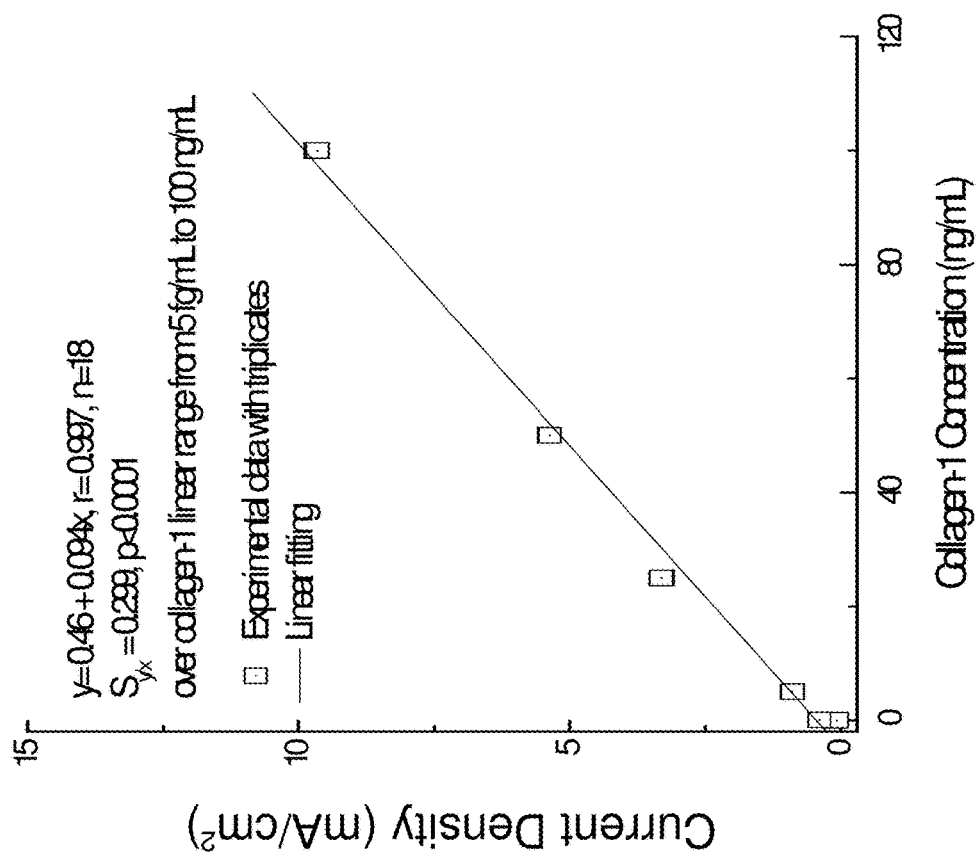

FIG. 38A depicts Device 2's current profiles over collagen levels 5.0 fg/mL to 200 ng/mL (9 levels from "a" to "j") vs. controls in PBS solution. Samples run triplicates. Inserts are for the enlarged view for the results at high and low-end concentration levels compared with controls. FIG. 38B depicts the calibration curve of current density vs. collagen-1 concentrations over the linear range of 5 fg/mL to 100 ng/mL (6 levels). FIG. 38C depicts the calibration curve of current density vs. collagen-1 concentration in an exponentially increase manner over 5.0 fg/mL to 200 ng/mL (9 levels). Samples run triplicates.

Figure 39B:
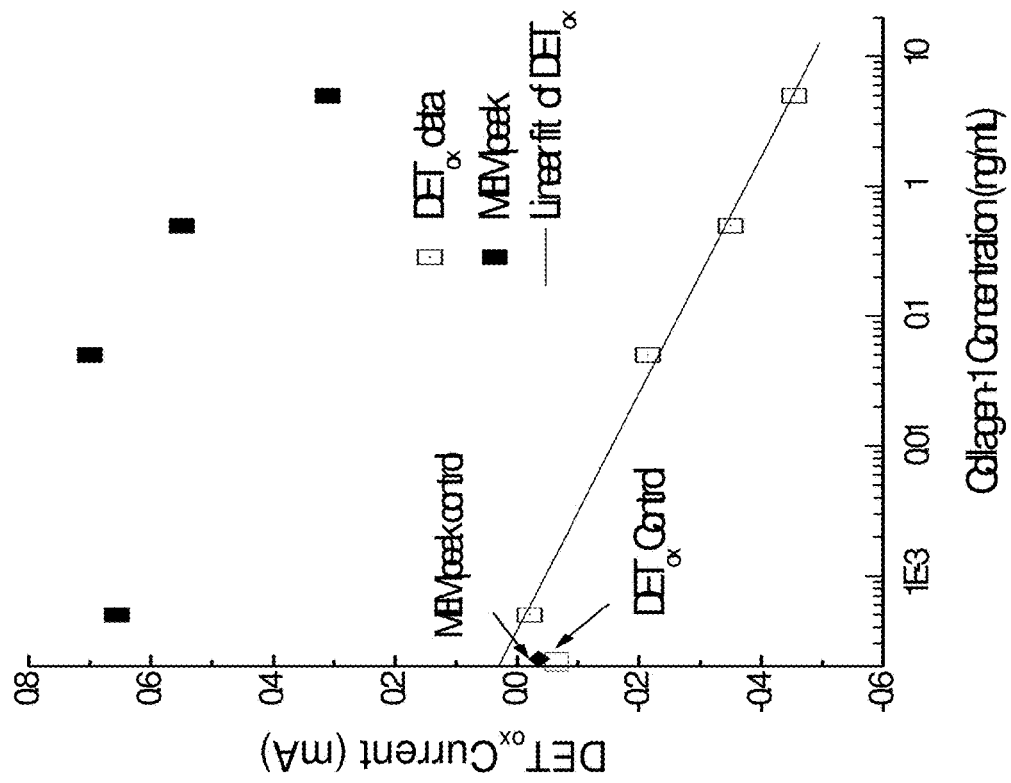
Figure 39A:
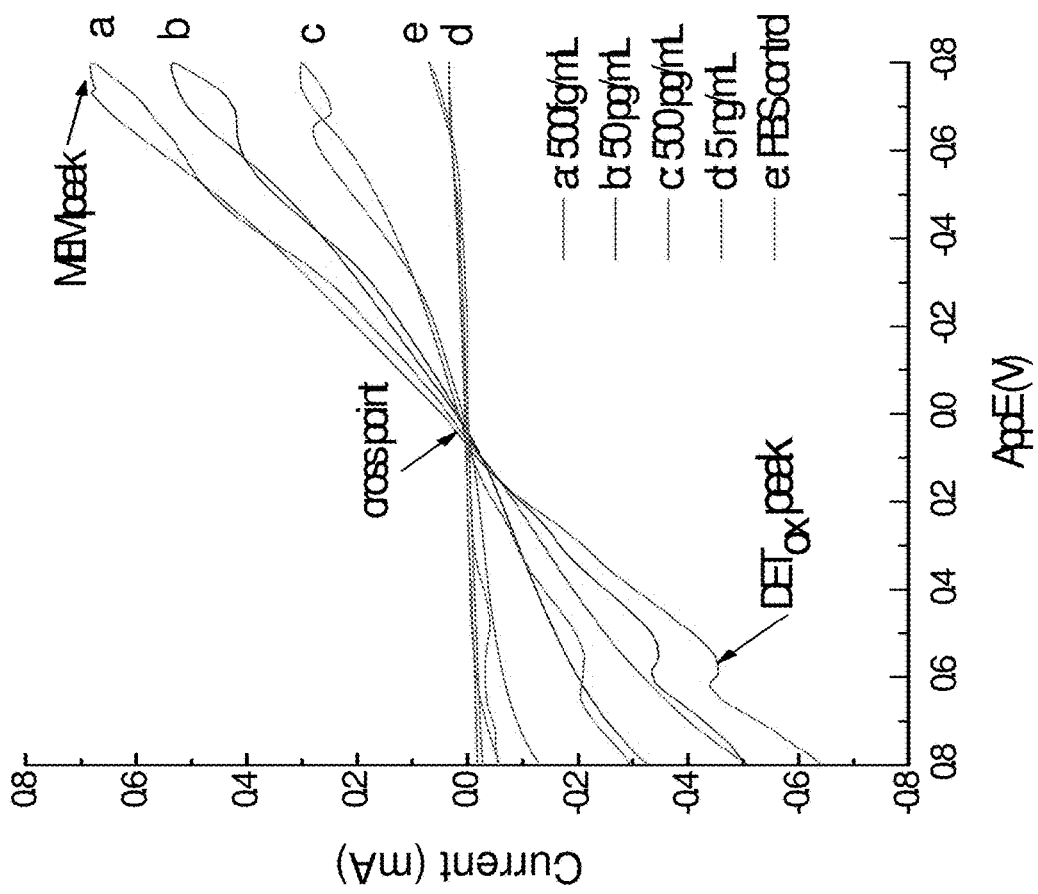

FIG. 39A depicts the i-V curves of the memristive characteristics of Device 2 in PBS in the presence of collagen-1 over 0.5 pg/mL to 5 ng/mL vs. control at 200 Hz scan rate. FIG. 39B depicts Device 2's $DET_{ox}$ peak current vs. collagen-1 concentrations in a log scale. The solid squire represents MEM peaks.

FIG. 40A depicts i-V plots of Device 3 (innate) with or w/o collagen-1 in PBS at 300 Hz. FIG. 40B depicts the linear plots of current vs. collagen-1 concentrations for $DET_{red}$ and $DET_{ox}$ peaks over 0.5 pg/mL to 500 pg/mL, respectively.

Figure 41C:
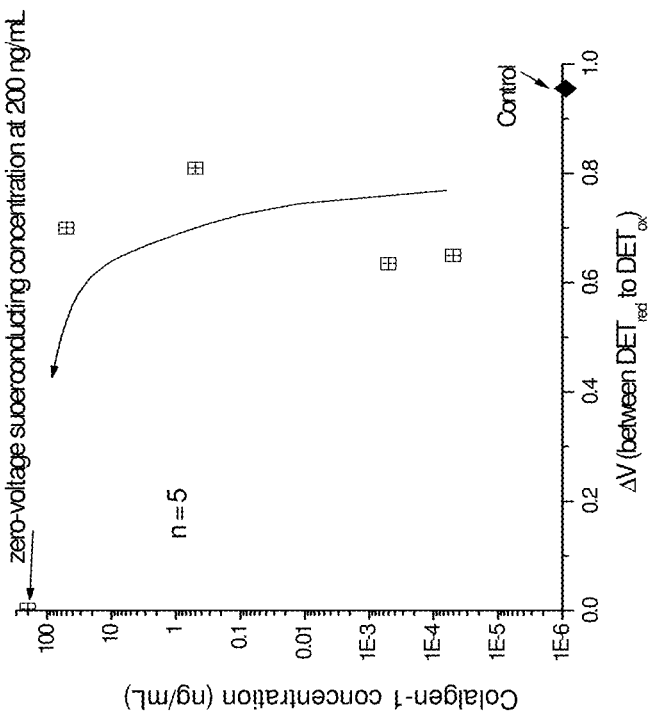
Figure 41D:
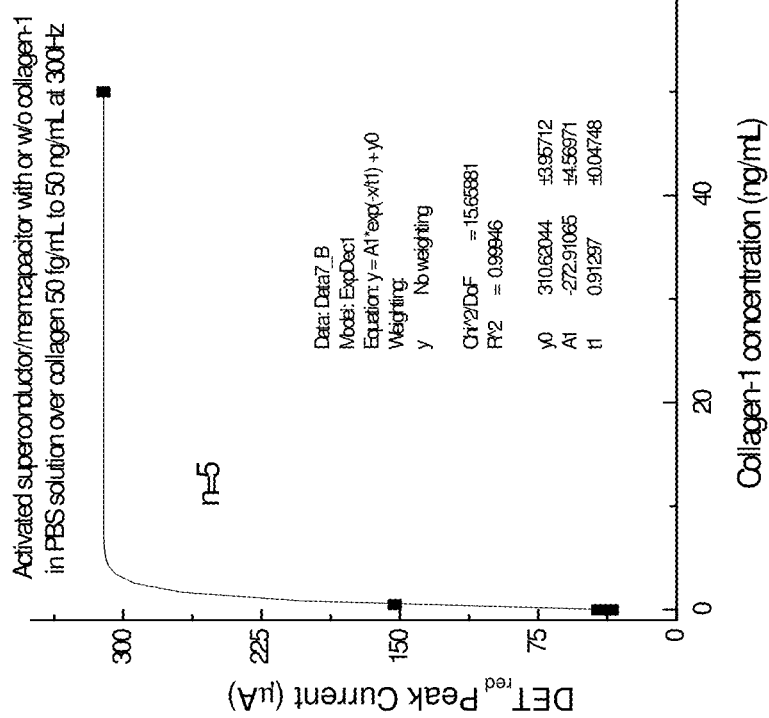

FIG. 41A depicts activated superconductor/memcapacitor Device 1 with or without collagen-1 concentrations over 50 fg/mL to 200 ng/mL in 5 levels in PBS solution compared with the control under 300 Hz scan rate. FIG. 41B depicts the 200 ng/mL collagen-1 transformed a memristive device to a superconductive device with zero-bias supercurrent and the $\pm\Delta$ is within the range 3 mV. FIG. 41C depicts the exponential increase relationship between the activated Device 1's $DET_{red}$ current and the collagen-1 concentrations between 50 fg/mL to 50 ng/mL. FIG. 41D depicts the trend of collagen-1 reduces the quantum energy gap of the potential difference between $DET_{red}$ and $DET_{ox}$ vs. collagen-1 concentration.

DETAILED DESCRIPTION OF THE INVENTION

Example 1—Fabrication of the Nanostructured Biomimetic Self-Assembling Membranes (SAM)

The nanostructured biomimetic ACHE SAM with the vertical bridged conformational "Mutated ACHE Gorge" was freshly prepared. Polyethylene glycol diglycidyl ether (PEG), triacetyl-β-cyclodextrin (T-CD), poly(4-vinylpyridine) (PVP) were purchased from Sigma. PVP was purified before use. The mono derivative dimethyl β-cyclodextrin named as (mM-β-DMCD) was generally synthesized according to the published procedures [19]. The appropriate amount of solutions of individual polymer and reagents were prepared [20]. The mixture solution was made up by mM-β-DMCD (2 g/L to 2.5 g/L, T-CD 2-3 mM, PEG 2 g/L-3 g/L and PVP (40 mg/dL-80 mg/dL), the mixture was incubated in 37 C for 2-3 hrs, then added 0.02M o-NPA with the molar ratio to TCD in the range of (500-1000):1 to the mixture for the device having a flat membrane with nanopores. The Au electrode has 50 nm thicknesses and 3 mm in diameter. The mixture solution was injected onto the surface of the electrode and was incubated for 48 hrs at incubation [20]. After that, the further clean and incubating procedures were followed by literature 20-22.

The nanostructured biomimetic "Normal ACHE Gorge" neuronal network SAM with the flat bridged conformation, nanopores and lattices was freshly prepared by adding appropriate amount of o-nitrophenyl acetate (o-NPA) into the above described mixture solution for construction of the cross bar toroidal matrix ACHE SAM. All other procedures were followed by literature 20-22. Adjusting the concentration of o-NPA leads to the air gaps thinner or thicker between the flat bridge bars and the vertical cross bars was suggested.

Example 2—AFM Measurements

The morphology of the cyclodextrin (CD) derivatives SAMs were characterized by using an instrument (model Multimode 8 ScanAsyst, Bruker, PA). Data collected in PeakForce Tapping Mode. Probes used were ScanAsyst-air probes (Bruker, PA). The silicon tips on silicon nitride cantilevers have 2-5 nm radius. The nominal spring constant 0.4 N/m was used. NanoScope Analysis v1.40r2 software was used. FIG. 23 illustrates the 3D memcapacitor blocks serve as the dual sensor, where sits on a 50 nm pure gold substrate plate attached onto a flexible plastic plate. The model consists of green balls and sticks in the top and bottom layer covered with conductive cross-linked polymers; the oranges represent the inner "ACHE Gorge" neuronal axons in narrow cylinders connected through the neuronal terminals and dendrites as truncated donuts in a compact flat metrics by forming toroidal matrix. The SAM fabricated by added o-NPA in the mixture of mM-1-DMCD, T-CD, PEG and PVP, that formed a flat bridge with nanopores. FIG. 24A shows the flat bridge with width 330 nm and length in 1.4 µm by cross section analysis with RMS 0.6 nm in the image. Nanopores can be seen on each side of the bridge; the pores on the left side of the bridge have a depth 0.3-0.8 nm and diameter 20-30 nm. FIG. 24B is the AFM image with the body of the horizontal flat bridge densely covered with thousands uniformly and orderly orientated donuts shaped "fish scales", density of $10^7$ pores/cm$^2$, with the average donuts size of 22 nm in diameter and the pores in the center are 9-10 nm in diameter. The AFM image in FIG. 24B shows the membrane thickness is about 35.5 nm and the membrane roughness is 12.5 nm.

Example 3—Mimicking the Active ACHE Gorge and its Linen

A "Normal Active Site ACHE Gorge" was defined as a linen-cylinder consists of a bipolar dome with two poles. (1): the positive isopotential pole: esteratic site of five residues containing the catalytic triad (Ser-200, Glu-327, His-440), acyl pocket Phe 288 and Phe-290 [23-26], that was mimicked by polyethylene glycol diglycidyl ether (PEG) (for Ser 200) . . . imidazolyl-dimethyl-β-cyclodextrin (M-CD) (for His 440) . . . triacetyl-β-cyclodextrin (T-CD) (for Glu327). Phe288 and 290 were mimicked by o-NPA. (2) The 14 aromatic residues for gorge lining were mimicked by excess amount of o-NPA (1:500-1000 of T-CD/o-nithophenyl acetate (o-NPA)) and W84 were mimicked by poly(4-vinylpyridine) (PVP); (3) the negative isopotential pole: the Asp-72, Tyr-121, Tyr-70, Tyr-354, and Trp-279 are the residues of the peripheral and were mimicked by TCD . . . PEG polymer and TCD . . . PVP polymers as anionic site (PAS), F330, Y121 were mimicked by o-NPA, and Trp279 was mimicked by PVP. FIG. 25 depicts the biomimetic ACHE gorge of a "normal neuronal cell" prosthesis on the left. On the right hand side is an illustration of the cross bar layout and it led to form the toroidal matrix.

Example 4—Engineering the Organic Memristor/Memcapacitor Device as the "Normal ACHE Gorge" Neuronal Network Device The "Normal ACHE Gorge" Neuronal Network Device (NND) was built by arrays of 3D cross bars by self-assembling technology with the above section mentioned membrane in FIG. 25. The FIG. 25 on the right-hand side is the illustration of the 3D cross bar, the vertical green bar presented here was made by the architecture of a vertical double-layer cylinder with an inner core cylinder consists of a chain of cyclodextrin chunked "donuts" shape, hollow in the center, as pendants and the nanometer air gap serves as the dielectric substance was located between the two electron-relay circuits and the PEG as the necklace chain passes through; the basement bar was made of the gold; The horizontal bar was made by the o-NPA formed hydrogen bounding or hydrophobic interaction with the TCD . . . PEG//TCD . . . PVP wrapped around the flat bridge structure. This is a partial illustration of the cross bar essential block, as shown the coil wrapped in a toroid. On the surface of the pure gold plate, the toroidal matrix conductive membrane was self-assembled through the imidazolyl derived mono-substitute β-dimethylcyclodextrin (m-β-DMCD, in short, MCD) cross-linked with PEG, PVP and TCD with positive and negative electron-relay circular current flow inside the cavity; the nano air gap between two chucked CD "donuts-like" cavity; and the o-NPA formed ACHE gorge linen with other residue groups through hydrogen bonding wrapped around the cross bars with the TCD . . . PEG//TCD . . . PVP polymers; the vertical nano air gap exists between the NPA linen and the polymer TCD . . . MCD . . . PEG . . . PVP; and the horizontal cross bars are of NPA linen with polymer TCD . . . PEG//TCD . . . PVP. The air gap between the CD cavity is much smaller than the air gap between the flat NPA mash bridge and the rim of the CD cavity. Herein, this device compromises the variations air gaps reflected the essence of the flexibility and neuronal plasticity necessary.

Sample 5—Characterization of the Organic Memristor/Memcapacitor

Memristors are devices made of nanolayers that have the capability to mimic neuronal synapse with a characteristic of hysteresis loop in the i-V curve [27-32]. A memristor is a semiconductor whose resistance varies as a function of flux and charge. This allows it to "remember" what has passed through the circuit [33, 27-29]. G({x},t) which is state dependent $$I(t)=G(\{x\},V,t)V(t) \quad (1)$$

The memristor's hysteresis i-V profiles measured by the cyclic voltammetry (CV) method and the i-V hysteresis curve with 0.4 mM Aβ in aqueous solution was demonstrated in FIG. 26 with a switch point at the origin (0, 0) against the control at 20 Hz scan rate indicating Aβ has the power to alternating a normal neuronal circuitry to pathologically dysfunction and alternating the brain cell's reversible membrane potential. FIG. 27A in NIST SRM965A human serum without Aβ. Data Acquisitions were conducted by connecting the memristor chips with an electrochemical station (Epsilon, BASi, IN) with the BASi software package in the computer. The gold chip consists of three gold leads, the center circle gold chip with the Biomimetic membrane is connected to the anode, and the pure gold electrode without a membrane is connected to the cathode electrode, and the gold electrode is connected to the reference electrode at a fixed scan rate under an applied electrochemical potential, the current was recorded due to the change of a direct electron-relay (DET) either in oxidation or reduction direction. DET phenomenon is a key event in sensing and energy storage that led to our several inventions [34-38]. Literature reported electric synapse is one tenth of that of chemical synapse [39]. The frequency change affecting on the memristor/memcapacitor was depicted in FIG. 27A using NIST serum without Aβ. At low frequencies, the sensor has the highest Direct Electron-relay Transfer (DET) [10-12, 40] peak intensity than at high frequencies and all curves have hysteresis characters.

The intensity of the DET peak was reduced by a hundred times, and the cross-point locations were moved nonlinearly toward to negative field as frequency increased in the presence of 3.8 nM and 76 nM Aβ as shown in FIGS. 27B and 27C, respectively compared to FIG. 27A without Aβ. Various concentrations of Aβ reduced the DET peak intensity by 94-99% in SWS frequency more than at any other frequencies as shown in FIGS. 27B and 27C. This memdevice showed significant bipolar nonlinear hysteresis through the CV curves at low frequency, and linear hysteresis at high frequency.

A total charge of a memcapacitor is a function of a state dependent of capacitance and the potential across it, where q(t) is the total charge on the capacitor, and V (t) is the potential across it. A capacitance C({x}, t) which is state dependent [28].

$$q(t)=C(\{x\},V,t)V(t) \quad (1)$$

The synapse energy profiles data Acquisitions were conducted by connecting the memcapacitor chips, the gold lead with nano-biomimetic membrane was connected to the anode, the bare gold lead was connected to the cathode, so was the reference connected to the pure gold lead, then the cable was connected with an electrochemical station (Epsilon, BASi, IN) with the BASi software package in the computer. The double step chronopotentiometry (DSCPO) method was used to measure the voltage change upon applied an alternative small current under ±10 nA with data rate 0.001 s at 0.25 Hz and $2\times10^{-5}$ s data rate over the frequency range of 40 Hz-1 kHz were chosen under the room temperature. The time for action potential and resting potential (discharge vs. charge steps) have to be settled in a desired time frame. The real time data was acquainted under this program. In this invention, the OriginPro 9.0 software was used for data analysis and plotting figures.

Sample 6—Overcome the Sample Instability of Aβ

Instability of Aβ in various media has been reported in the literature [4-6], and our own experiments confirmed the instability in aqueous solution. The CV curves shown in FIG. 28 illustrate the peaks were instable in water evidenced by the curve's cross-point moving more than 0.55V from negative potential toward positive potential direction between 500 ng/mL Aβ and 2 μg/mL Aβ. After 0.1 mg/mL TCD presences in the media, the CV curves are stabilized over the Aβ concentration ranges from 3.8 nM, 15 nM to 380 nM and the signal intensity was inversely proportional to the concentration against the control as shown in FIG. 29. It is noticed that the cross-point disappearing over the Aβ concentration ranges in the newly presented TCD indicates TCD may play a positive role in blocking Aβ forming a twisted neuronal circuitry.

Sample 7—Quantitation of Aβ

The CA Method. The CA method was used for quantitation of Aβ. Aβ$_{25\text{-}35}$ was purchased from Sigma. The data were acquired at room temperature under two-step fixed potentials in 8 concentration levels covering Aβ final concentrations ranging from $10^{-11}$ M to $10^{-7}$M, with triplicates in DDH$_2$O with 0.1 mg/mL TCD and using an electrochemical work station (Epsilon, BASi, IN) with the companied software package. Origin 9.0 was used for all statistic data analysis and figure plotting.

FIG. 30 illustrates CA curve profiles in the presence of Aβ in aqueous solutions over the range of 0.037 to 151 nM Aβ. FIG. 31 illustrates the calibration curve with a linear regression equation Y=0.59+0.63X, r=0.998 (n=23), P<0.0001, Sy/x=1.96. The value of Detection of Limit (DOL) is $5.0\times10^{-11}$M per cm$^2$ with a pooled relative standard deviation of 0.2% related to that at the mean concentration. Because this sensor is only 0.031 cm$^2$, hence its DOL is 1.6 pM Aβ.

The Voltage Method. The characterization of the memcapacitor serving as a voltage sensor was conducted by the DSCPO method in ±10 nA and 0.25 Hz in DDH$_2$O with 0.1 mg/mL TCD, with spiked Aβ final concentrations from 0.038 nM to 60.8 nM, and with triplicates for a calibration curve. The NIST SRM 965A human reference serum, with controlled blood glucose 70 mg/dL, spiked with Aβ having 4 levels from 3.8 to 417 nM with a single run at the same experimental conditions as in water media, and measurements without spiking Aβ were also taken for comparison.

The magnitude of voltage change was in the highest when Aβ was not presence as shown in FIG. 32A$_1$ having the curves averaged from triplicate runs. The Aβ affects on synapse discharge voltage curves were depicted in FIG. 32A$_2$ with signal intensity inversely proportional to Aβ concentration. The volumetric energy density in the calibration curves as shown in FIG. 32B$_2$ was inversely proportional to Aβ concentrations with a linear regression curve in water (in black) equation Y=1.48−0.018X, r=−0.992, S$_{y/x}$=0.058, n=12, p<0.0001 over volumetric energy density from 0.41 to 1.50 μWHr/cm$^3$. The Detection of Limit (DOL) is $2.63\times10^{-9}$M per cm$^3$ with a pooled relative standard deviation of 5% related to that at the mean concentration. Because this sensor is only $3.11\times10^{-7}$ cm$^3$, hence, its DOL is $8.2\times10^{-16}$M Aβ. FIG. 32B$_1$ illustrates the experimental data points of volumetric energy density vs. Aβ concentration from zero to 471 nM in NIST serum (Red) without a stabilizer TCD, and in water with 0.1 mg/mL stabilizer TCD (black), respectively. The Aβ calibration curve using NIST's reference human serum is shown in FIG. 32B$_2$ in red. The experimental DSCPO curve's control profile is shown in FIG. 32C$_1$ in NIST SRM965A serum samples for without spiking Aβ at ±10 nA at 0.25 Hz. FIG. 32C$_2$ depicts synapse voltage profiles covering clinically useful range between 3.8 to 471 nM Aβ. The linear regression equation of Y=7.51−0.014X, r=−0.995, Sy/x=0.36, N=4, p<0.005. The DOL value is $7.0\times10^{-13}$M/cm$^3$.

Sample 8—Media Affects on the Sensitivity of Detection of Aβ

The difference between −0.018±$7.5\times10^{-4}$ and −0.014±0.001 μWHr/cm$^3$/nM is statistically negligible in comparing of the device sensitivity to Aβ in water and in human serum based on a two-tailed Student t test at $t_{0.025}$. It is simply states that there is no protein interference on the sensitivity to detect Aβ in different media using this device, wherein the proportional systematic error is statistically negligible.

Our results demonstrated Aβ is a strong inhibitor agent in blocking memory consolidating at Slow-Wave-Sleeping (SWS) at 0.25 Hz with the initial energy intensity decrease by 94% in 3.8 nM Aβ in serum. It was observed in the insert of FIG. 32B that the synapse energy density signal at Aβ=0 is 8.5-fold higher in the serum than in the aqueous solution at 0.25 Hz indicating the serum is more suitable to the neuronal memcapacitor sensor without instability observed. The synapse energy DSCPO profiles in the presence of Aβ using NIST serum samples were depicted in FIG. 32C. The insert shows the curve without Aβ.

Sample 9—Factors Affect Sensors' Performance

Peak duration time and Aβ concentrations were factors that affect on sensor's performance using the CA method. A healthy subject's fresh finger stick capillary whole blood (CPWB) specimens were collected, then immediately spiked Aβ in various concentrations in less than 4% water content to the blood volume without anticoagulant and without stabilizer. All measurements were in triplicates against controls at room temperature and finished in a half hour. Peak duration time had three levels: 4 ms, 25 ms and 4 s. The same factors were used for the voltage sensor under conditions of ±10 nA and 0.25 Hz with data rate 1 kHz, 40, 250 Hz (both had data rate 50 kHz) for action potential peak or resting potential peak, respectively. The subject has gone through consent and was approved with the IRB.

FIG. 33 revealed the high energy density values were associated with specific capacitance values between 1.2-2.2 F/cm$^3$ around zero Aβ compared with the negligible energy density at high Aβ level based on the calculations on the literature [41-42] using n=27 fresh human CPWB specimens with the voltage method. FIG. 34 depicts a map revealed the results obtained by another CA method using the same fresh human CPWB specimens with the larger current density correlated with the highest Aβ concentration that located in the higher frequency at 250 Hz.

Sample 10—Assessing Precision and Accuracy

Precision was evaluated by the two methods using fresh human CPWB specimens with triplicates at two levels of Aβ at 2.3 and 92 nM and three levels of frequencies at 0.25, 40 and 250 Hz in triplicates. Accuracy results were assessed by the "Point Accuracy" using signal means of the CPWB specimens against the calibration curves with the reference results that are traceable to NIST reference serum with the standard addition of the Aβ concentrations.

The imprecision was measured by the CPWB samples for the two sensors with the Pooled RSD of 3.2% (n=18) vs. 6.0% (n=15) over the studied ranges for the CA and the DSCPO method, respectively. The inaccuracy error was 0.1% with a recovery of 100.15±1.2% for CA method after corrected metrics ratio. The average inaccuracy error obtained from the DSCPO method are 0.01% and 1.4% in water and in serum, respectively, that were traceable to the NIST's reference with 99.99±0.01% and 98.6±1.1% recovery.

Sample 11—Signal to Noise Ratio

The ratio of Signal to Noise (S/N) values accessed by the CA method and the DSCPO methods, respectively, were calculated based on the conventional teaching [43]. The results have S/N values of 11.63 vs. 12.5 for the CA and DSCPO method, respectively.

Conclusion

The dual sensors detected sub pM Aβ with near 100% recoveries and 3-6% imprecision under antibody-free and tracer-free conditions were demonstrated. The technology may find wide applications for early monitoring of Alzheimer's disease.

REFERENCES

[1]. Reitz C, Brayne C and Mayeux R, *Epidemiology of Alzheimer disease*, Nature Reviews Neurology 7, 137-152, 2011.

[2]. John E. Morleya J E and Farr S A, Biochemical Pharmacology, 88(4), 479-485, 2014.

[3]. Jia Q, Deng Y, and Qing H, BioMed Research International Article ID 837157, 22 pages, 2014.

[4]. Toledo J B, Shaw L M and Trojanowski J Q, Alzheimer's Research & Therapy 5, 8, 2013.

[5]. Lachno D R, Emerson J K, Vanderstichele H, et al, J Alzheimers Dis 32, 905-918, 2012.

[6]. Bibl M, Welge V, Esselmann H, Wiltfang J, Electrophoresis 33, 445-450, 2012.

[7]. Esparza T J, Zhao H, Cirrito J R, Cairns N J et al., Ann Neurol, 73(1), 104-119, 2013.

[8]. Fiandaca M S, Mapstone M E, Cheema A K, Federoff H J, Alzheimer's & Dementia, 10, S196-S212, 2014.

[9]. Zlokovic B V, Neuron, 57(2), 178-201, 2008.

[10]. Chen E T, Duh S H, Ngatchou C, Thornton J T, and Kissinger P T, Nanotech (3), 101-104, 2011.

[11]. Chen E T. U.S. Pat. No. 6,582,583, Jun. 24, 2003.

[12]. Chen E T, U.S. Pat. No. 8,083,926, Dec. 27, 2011.

[13]. Chen E T, Thornton J T, Ngatchou C, Duh S H and Kissinger P T, NSTi-Nanotech (3), 115-118, 2013.

[14]. Chen E T, Thornton J T, Ngatchou C, Duh S H and Kissinger P T, NSTI-Nanotech (2), 107-110, 2013.

[15]. Chen E T, Thornton J, Ngatchou C and Duh S-H., NSTi-Nanotech, 2, 169-172, 2014.

[16]. Chen E T, Thornton J and Mulchi Jr C. Sensors & Transducers, 183(12), 72-83, 2014.

[17]. Nordberg A, Rinne J O, Kadir A and Langstrim B, Nature Reviews, 6, 78-87, 2010,

[18]. Yan J J, Cho A-Y, Kim H-S, Kim K-L, Jung J-S, British J of Pharmacology 133(1). 89-96, 2001

[19]. Chen E T and Pardue H L, *Anal Chem,* 5, 2563-7, 1993.

[20]. Chen E T, Thornton J T, Ngatchou C, Duh S H and Kissinger P T, NSTi-NanoTech (2), 107-110, 2013.

[21]. Chen E T, Thornton J T, Ngatchou C, Duh S H, NSTi-Nanotech, 2, 200-203, 2014.

[22]. Szejtli J, *Cyclodextrin and Their Industrial Uses*, Editions de Santé, Paris. 1987.

[23]. Sussman J L, Harel M, Frolow F, Oefner C, Goldman A, Toker L, Silman I, *Atomic structure of acetylcholinesterase from Torpedo californica: a prototypic acetylcholine-binding protein.* Science 253, 872-879, 1991;

[24]. Gilson M K, Straatsma I T P, McCammon J A, Ripoll D R, Faerman C H, Silman I, Sussman J L, *Open "back door" in a molecular dynamics simulation of acetylcholinesterase,* Science 263, 1276-1278, 1994.

[25]. Silman I, Sussmana J L, *Acetylcholinesterase: How is structure related to function?* Chem Biol Interact. 175, 3-10, 2008.

[26]. Mira A, Yamashita S, Katakura Y, and Shimizu K. *In vitro neuroprotective activities of compounds from Angelica shikokiana makino*, Molecules 20, 4813-4832, 2015.

[27]. Biolek D, Di Ventra M, Pershin Y V, *Reliable SPICE Simulations of Memristors, Memcapacitors and Meminductors*, Radioengineering 22 (4), 945-968, 2013.

[28]. Martinez-Rincon J and Pershin Y V, *Electron Devices, IEEE Transactions* 58 (6), 1809-1812, 2011.

[29] Martinez-Rincon J, Ventra M D, Pershin Y V, *Solid-State Memcapacitive System with Negative and Diverging Capacitance Physical Review B,* 81(19), 195430-1-195430-7, 2010.

[30] Pickett M D, Medeiros-Ribeiro G and Williams R S, A Nature Materials, DOI: 10.1038/NMAT3510, 2012.

[31] Kozma R, Pino R E, Pazienza G E, *Advances in neuomorphic memristor science and applications,* Springer publisher, 2012.

[32] Ventra M D, Pershin Y V, Nanotechnology 24, 255201, 2013.

[33] Ventra M D and Pershin Y V, *On the physical properties of memristive and memcapacitive and meminductive systems,* J of Physics D, arXiv:1302.7063v2, 2013.

[34] Chen E T, Nanopore Array Structured Devices for Biosensing and Energy Storage, U.S. Pat. No. 8,641,876, Feb. 4, 2014.

[35] Chen E T, *Nanopore Structured Electrochemical Biosensor*, U.S. Pat. No. 8,083,926, Dec. 27, 2011.

[36] Chen E T, *Apparatus and Methods for Making High Performance Fuel Cell*, U.S. Pat. No. 8,632,925 issued by USPTO, Jan. 21, 2014.

[37] Chen E T, *Nanostructured Biomimetic Device with Contour Map of Multiple Variable Correlation Method to Visually Display the Cancer Progresses*, US 20,140,178, 925, Jun. 26, 2014.
[38] Chen E T, *Nanobiomimetic Supercapacitors with High Rate High Energy Storage*, US 20,140,104,751, Apr. 17, 2014.
[39]. Buzsaki G et al., Nature Reviews 13, 407-420, 2012.
[40] Chen E T, *Nanobiomimetic sensing and energy storage* in the first volume of the book series of *Dekker Encyclopedia of Nanoscience and Nanotechnology* edited by Lyshevski S E, CRC Press, 2013.
[41] Hu L, Choi J W, Yang Y, Jeong S, Mantia F L, Cui L-F and Cui Y, PNAS 106 (51), 21490-21494, 2009.
[42]. Thornton J, Christelle C and Chen E T, NSTi-Nanotech (2), 672-675, 2013.
[43]. Skoog D A and Leary J J, *Principles of Instrumental Analysis*, Fourth Edition, Saunders College Publishing, 1992.

FOLLOWING IS THE DETAILED DESCRIPTION OF THE CURRENT CIP INVENTION

Example 1—Fabrication of the Nanobiomimetic Organometallic Superconductive/Memristive and Superconductive/Memcapacitive/Meminductive Devices Having Superlattice Toroidal Structures Device 1's membrane was freshly prepared by self-assembling method with compositions of triacetyl-β-cyclodextrin (TCD), polyethylene glycol diglycidyl ether (PEG), poly(4-vinylpyridine) (PVP), bis-imidazole substituted dimethyl-β-cyclodextrin (bM-1-DMCD), cysteine and embedded zinc chloride on gold chips with appropriate proportions at 37° C. for 96 hours. Device 2 was made by two steps: first, deposits a polymer mixture of TCD/PEG/PVP/β-CD copolymer, that mimics choline acetyltransferase (CHAT) on the 50 nm gold chip with appropriate proportions forming nano-island layer 1 and the AFM image confirmed the nano-islands structure; the second step was to deposit another freshly prepared similar polymer mixture as Device 1 does, except without the L-cysteine, on the top of the nano-island membrane. The second layer of the polymer mixtures of bM-β-DMCD//PEG/PVP/TCD/$ZnCl_2$ has a volume ratio range from 6:1 to 10:1 for bM-β-DMCD to each of other component, except to $ZnCl_2$, 4:1 with the CD's concentration in 10-fold higher than that of PEG or PVP, respectively. At the first 2 hours, the temperature kept at 80° C., after that the temperature was reduced to 37° C. for 96 hours. For other procedures, reference was on the literature [9]. Procedures of synthesis and characterization of mM-β-DMCD and bM-β-DMCD were based on the published literature [21]. Denaturing procedure of Device 1's membrane was conducted at 80° C. for 5 minutes, then washing and the dry procedure was followed.

Example 2—Fabrication of the Native MMP-2 Protein Superconductive/Memristive Devices with Superlattice Toroidal Structures The reference device, Device 3, was fabricated by the polymer mixture of TCD/PVP/PEG and the native MMP-2 protein in appropriate proportions at 37° C. for 96 hours on a 50 nm gold chip. MMP-2 enzyme was purchased from Ana Spec (Freemont, Calif.).

Example 3—Models Used to Engineering the Superconductive/Memcapacitive or Superconductive/Memristive Devices FIG. 15 depicts the schematic components in the engineering design of the superconductive/memcapacitive/memristive device 1 in a front-face view. "20" is the gold electrode with 50 nm thickness adherences on a flexible plastic plate substrate with a switchable connection; "21" is the cooper pair electrons, "22" is the collagen-1 matrix, "23" refers to the zinc-imidazole of the mono imidazole modified-β-dimethylcyclodextrin (mM-β-DMCD), in short as MCD, that it coordinates in two schemes: (1) zinc ion chelated with four imidazole groups in cavities of four MCDs and also with one $COO^-$ group of TCD; another scheme is the zinc ions chelating with three imidazole groups in three MCDs and the fourth ligand is with either the $COO^-$ group from the TCD as "24" or with the $COO^-$ group from N-acetyl-L-cysteine referred to as "25", and the fifth ligand is with the imidazole group in bM-β-DMCD; "26" refers to the repeating processing of n units; "27" refers to the PEG . . . PVP forming biomimetic proteins' N-terminal vertical architecture of the toroidal memristive structure; "28" refers to the PEG . . . TCD chain forming biomimetic proteins' C-terminal vertical architecture of the toroidal; "29" refers to the repeated units. Notice there is an air gap space around zinc ions.

FIG. 16 depicts the schematic components in the engineering design of the superconductive/memristive/meminductive (SMRMI) device 2 in a side view. "40" is the gold electrode with 50 nm thickness adherences on a flexible plastic plate substrate with a switchable connection; "41" is the Cooper pair electrons, "42" is the collagen-1 matrix as an insulator, "43" refers to the zinc-imidazole of the MCD coordination complex: zinc ion chelated with four imidazole groups in cavities of four MCDs, and also chelates with the $COO^-$ group of TCD; another zinc ion chelates with three imidazole groups in three MCDs, and with one $COO^-$ group of TCD as "44", and one ligand with imidazole group in bM-β-DMCD as "48"; "45" refers to the repeating processing of "n" units; "46" refers to the PEG . . . PVP forming biomimetic proteins' N-terminal vertical architecture of the toroidal memristive structure; "47" refers to the PEG . . . TCD chain forming biomimetic proteins' C-terminal vertical architecture of the toroidal; "48" refers to the repeated units. Notice there is an air gap around zinc ions. "49" refers to the repeated units. "50" refers to the nanoislands structure membrane on 50 nm thickness gold electrode on a plastic substrate with a switchable gold electronic connect lead; the nano-island membrane comprises of TCD . . . PEG . . . PVP . . . β-CD copolymer, that mimics choline acetyltransferase (CHAT).

FIG. 17 depicts the art model for Device 2 in a side view of the Josephson Junction. "60" is the electrode; "61" is the amplified wave after the Cooper pair went through the multiple superconductor-Insulator-superconductor (SIS) layers at a higher frequency. "62" refers to the Cooper pair; "63" refers to the collagen-1 matrix; "64" refers to the circular current flow in a positive direction with the zinc atoms as the brown balls; "65" refers to the cyclodextrin array matrix alignment with each other produced the eternal superconducting current in the blue circle having induced a $\varphi_0$, single flux quantum, that a non-ferromagnetic field is produced; "66" is the nanoisland membrane on the gold electrode; "67" is the wave of cooper pair electrons after passing through the nanoisland membrane; Notice there is an air barrier between the membrane and the array of cyclodextrin matrix. "68" refers to the PEG . . . PVP's N-terminal chain.

FIG. 18 depicts schematic components of the superconductive/memristive (SMR) activated MMP-2 protein device 3 in a side-view. "100" refers to the electrode; "101" refers to the amplified wave after the cooper pairs passed through the layers of superconductive-insulator-superconductive membranes; "102" is the cooper pair; "103" refers to the collagen-1 matrix; "104" refers to the superconducting membrane in horizontal orientation that comprised of the native MMP-2, TCD, PEG, and PVP. The blue diamonds on the rings refer to the migrated zinc atoms from the MMP-2. Inside have two small rings referring to multiple toroidal matrix arrays and it repeated for multiple times. Notice there is an air gap between the toroidal rings. Hence it comprised an SIS-SIS-SIN chain for amplification. "105" refers to the PEG . . . TCD vertical chain mimicking of C-terminal of a protein, and the right-hand side of the similar chain referrers to the PEG . . . PVP chain of mimicking N-terminal chain. "106" refers to the supercurrent wave from the Cooper pair after they passed through the superconducting layer. The two blue circles refer to the circler superconducting current that produced single flux quantum with the blue arrow is the induced electromagnetic field.

FIG. 19 refers to an enlarged top view of the superconducting membrane of activated Device 3.

Example 4—Characterization of the Membranes

The morphology of the AU/SAM was characterized using an Atomic Force Microscope (AFM) (model Dimension Edge AFM, Bruker, MA). Data collected in Tapping Mode using silicon probes with 5-10 nm tip radius and ~300 kHz resonance frequency (Probe mode TESPA-V2, Bruker, MA). FIG. 20 refers to the 2D AFM image of the Device 1's superconducting membrane with the zinc atoms in white color; the Cooper pair electron cloud moves toward the same direction. FIG. 21 depicts the 3D AFM image of the protein MMP-2 membrane with superlattice matrix of the Device 3. Zinc atoms are either along with the toroidal rings or on the top of the ring.

FIG. 22A depicts the 2D superlattice layered structure with zinc atoms in sensor mode with cross-section analysis in 5×5 μm² with a diameter 200 nm and average length 2-3 μm forming array lattice with an average area of the lattice occupying 21-25 μm², while zinc atoms on the edge or at the center of the lattice in that the device covered with 1.5×10⁵ uniform oriented superlattice on top of the nanoisland layer. FIG. 22B depicts the Device 2's whole screenshot image before taken AFM. FIG. 22C depicts a 3D image of the curvature single-wall nanotube with zinc atoms on top; FIG. 22D depicts the 2D image of the multiple waves formed in the carnal in the membrane of Device 2 with the carnal location near the cross in FIG. 22B. FIG. 22E depicts the deep carnal with superlattice on the top surface. FIG. 22F depicts the 3D view of the superlattice of Device 2. FIG. 22G depicts the first nanoisland membrane on the gold chip, before depositing other mixture solution. FIG. 23A depicts the nature MMP-2 sensor's circular structures with zinc atoms. FIG. 23B depicts the tapping mode for detail shown the zinc atoms in nature MMP-2 protein membrane.

Example 5—Evaluation of the Friedel-Oscillation in the Superlattice Toroidal Membranes Evaluations of the Friedel-oscillation in the superlattice membrane was conducted based on the AFM images. Friedel-oscillation is a phenomenon for long-range indirect interactions between electrons on the surface [20]. The AFM images revealed the Friedel-oscillation are presented in FIG. 20 for Device 1. FIG. 21 is the 3D AFM image for the native protein Device 3 having superlattice structure and the zinc ions acted as the Josephson junction that have the Friedel-oscillation. FIG. 22A depicts the 2D image in a bird-eye-view of the superlattice superconducting membrane with curvature nanotubes and the zinc atoms are served as the junction of Device 2 in a sensor mode with cross-section analysis in 5 μm×5 μm; FIG. 22B is the photo image structure of the whole SAM superconductive multiple layers membrane on the screen during setting the probe before taken an AFM image. FIG. 22C is a 3D image of the curvature single-wall nanotube with zinc atom on top; FIG. 22D depicts the 2D image of the multiple waves formed in the carnal in the membrane of Device 2 with the carnal location near the cross in FIG. 22B. FIG. 22E depicts the deep carnal with superlattice on the top surface. FIG. 22F depicts the 3D bird-view of the superlattice of Device 2. FIG. 22G depicts the first layer nanoisland membrane on the gold chip, before the depositing other mixture solution.

FIGS. 23A and 23B depict the AFMs of the native MMP-2 Device 3's single-wall nanotubule toroidal structures with zinc atoms that are like diamonds on a ring or oscillation in the center in an amplitude mode or in a sensor mode, respectively. All rings have the same thickness in 90 nm in the circular nanotubes, and the diameters of the toroidal are in the range of 2.3-5.5 μm, and the height of the toroidal is from 0.5 to 0.9 μm. Zinc atom migration from the original cluster to other rings was observed.

Example 6—Evaluation of Topological Superconductor/Quantum Memcapacitor (TSC/QMC) Device in Superconductivity/Memcapacity The TSC/QMC Device 1.

Figure 2A:
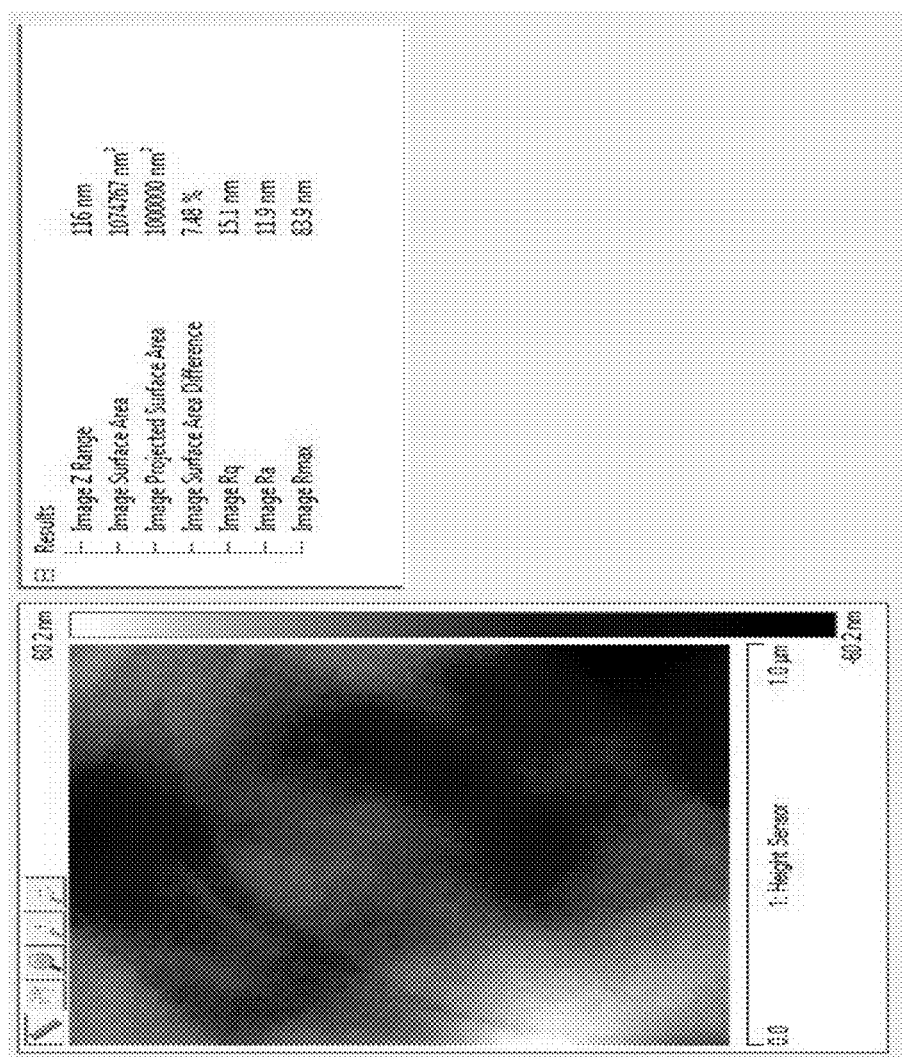
FIG. 2A shows the AFM image of the nanostructured flat horizontal bridge and large nanopores as "breathing-hole" nearby the bridge.
Figure 1:
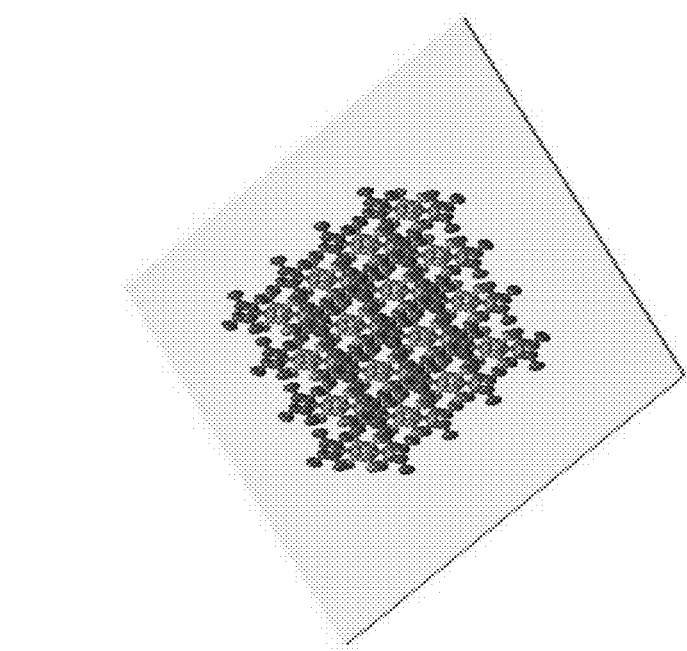
FIG. 1 illustrates the 3D memcapacitor blocks serve as the dual sensor. The light green color substrate is a 50 nm thickness pure gold plate attached onto a flexible plastic plate. The model consists of green balls and sticks in the top and bottom layer covered with conductive cross-linked polymers; the oranges represent the inner "ACHE Gorge" neuronal axons in narrow cylinders connected through the neuronal terminals and dendrites as truncated donuts in a compact flat metrics by forming toroidal matrix.
Figure 2B:
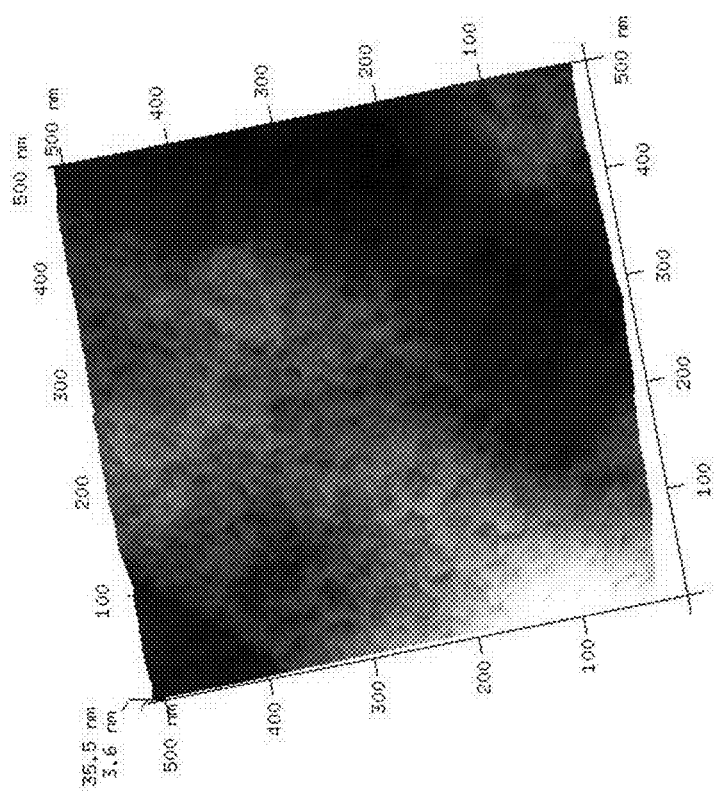
FIG. 2B shows the enlarged AFM of the flat bridge/nanopore AFM structure.
Figure 3:
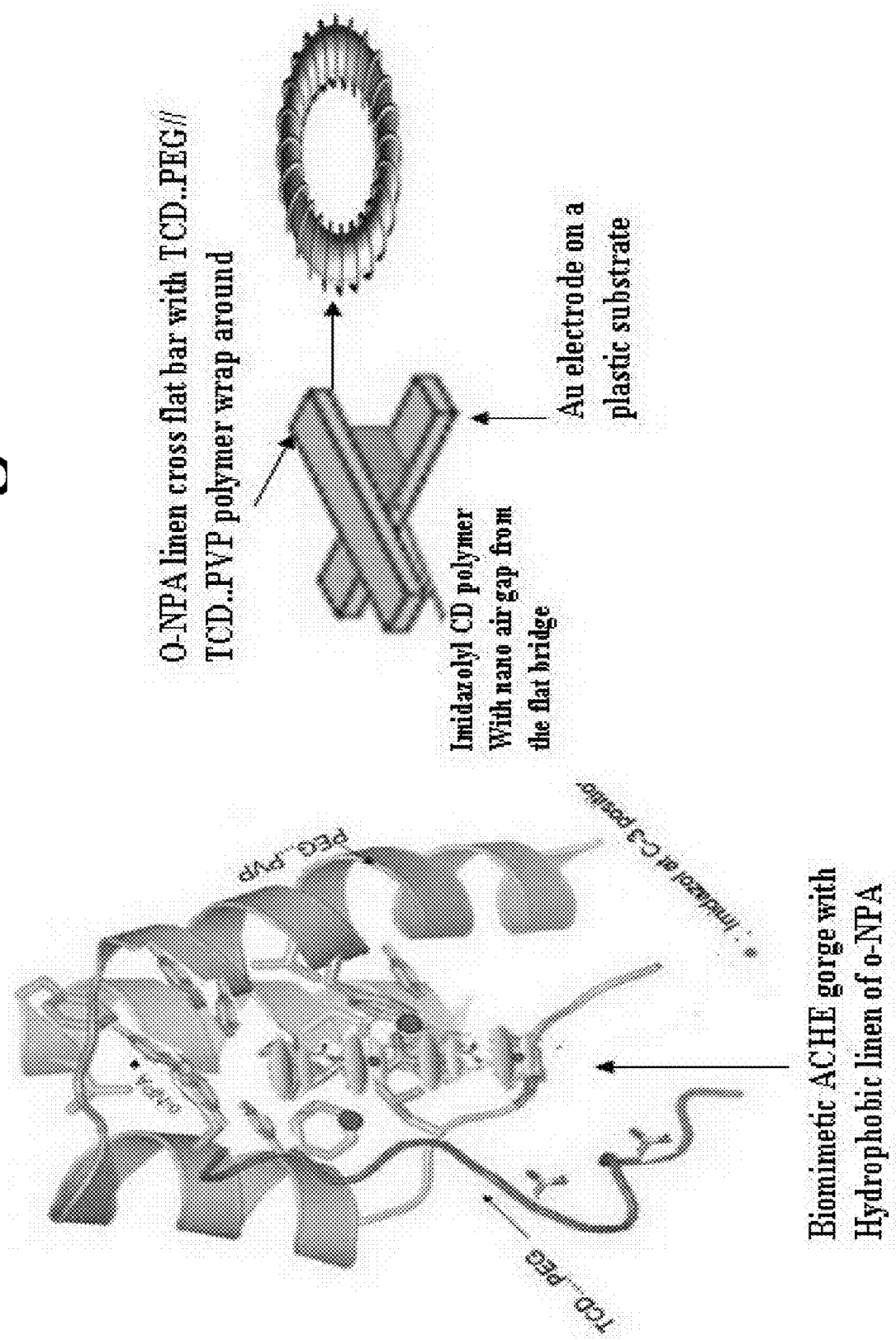
FIG. 3 depicts the art illustration of the SAM molecular polymer architecture for the Biomimetic normal ACHE gorge neuron in the left, and on the right hand side is an illustration of the cross bar layout and led to form the toroidal matrix.
Figure 4:
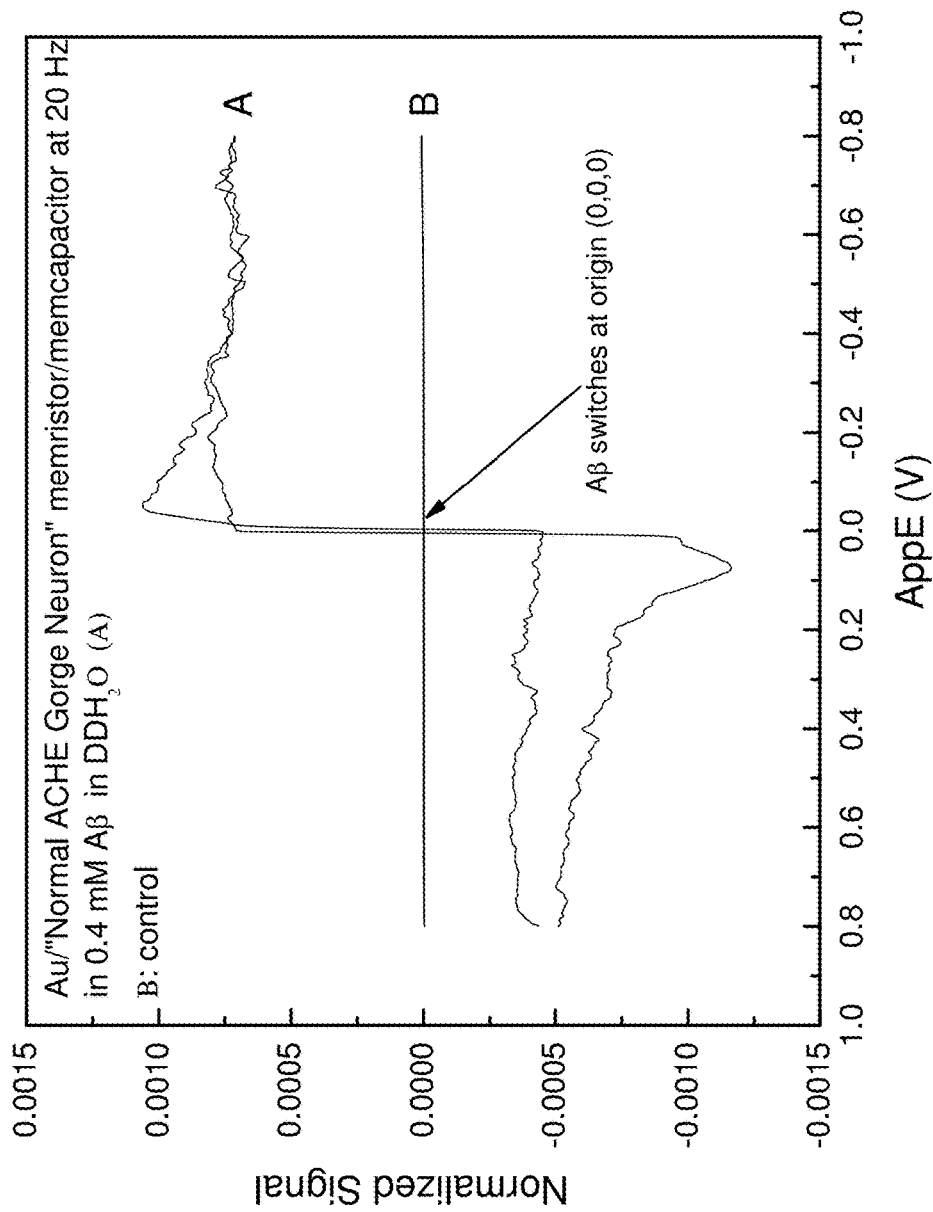
FIG. 4 illustrates the hysteresis of the i-V curve of "A" in 400 μM Aβ in $DDH_2O$ with a switch point at origin (0, 0, 0) against the control curve "B".
Figure 5B:
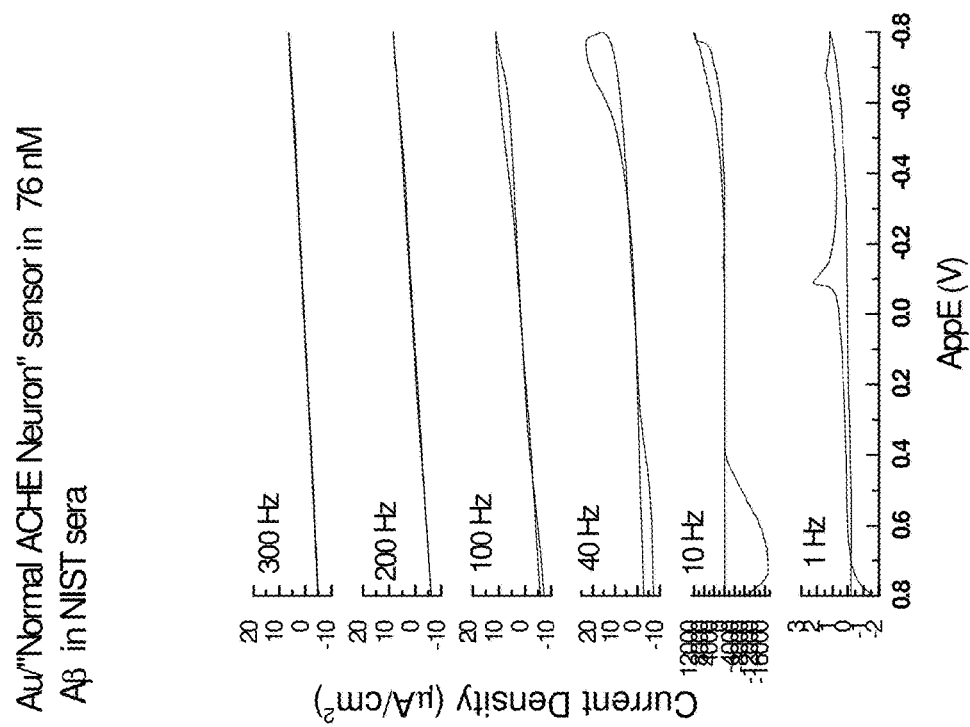
FIG. 5B depicts frequency affects on CV curves from 1 to 300 Hz in NIST SRM965A human serum with certified blood glucose in level 2 (70 mg/dL) with 3.8 nM Aβ.
Figure 5A:
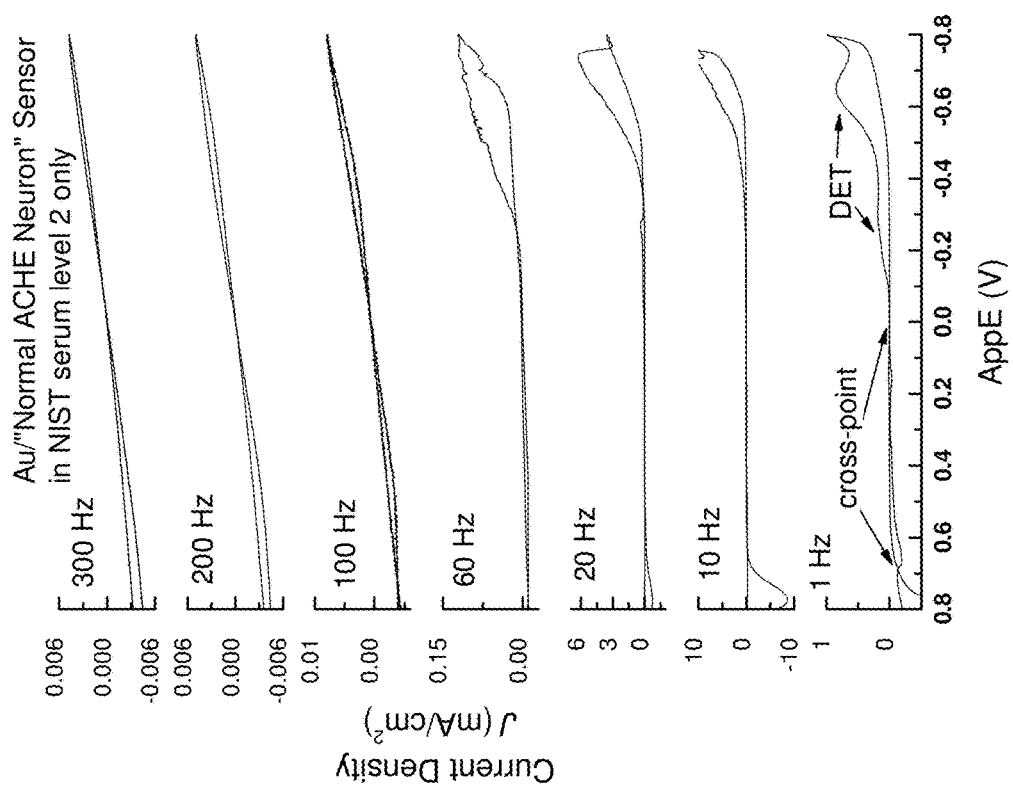
FIG. 5A depicts frequency affects on CV curves from 1 to 300 Hz in NIST SRM965A human serum with certified blood glucose in level 2 (70 mg/dL) without Aβ.
Figure 7:
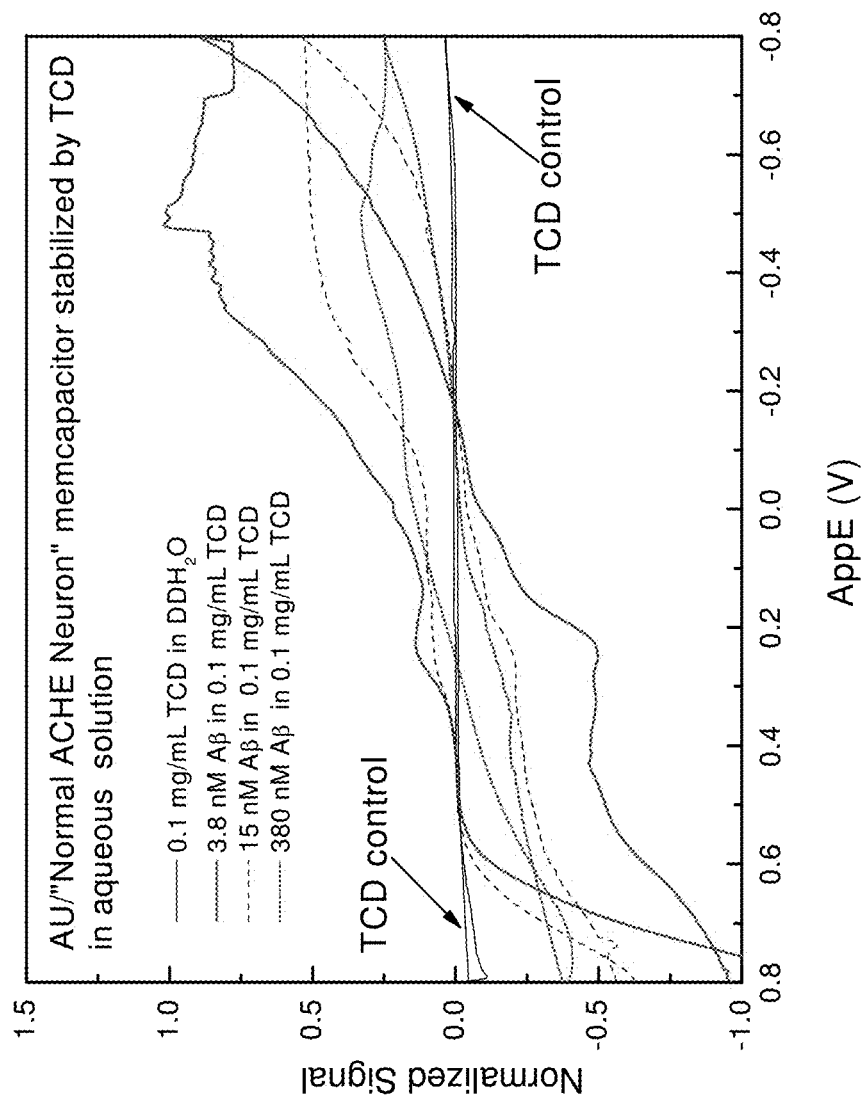
FIG. 7 depicts the i-V behaviors of the sensor in the 0.1 mg/mL stabilizer TCD in $DDH_2O$ with Aβ at 0, 3.8, 15, 380 nM, respectively.
Figure 8:
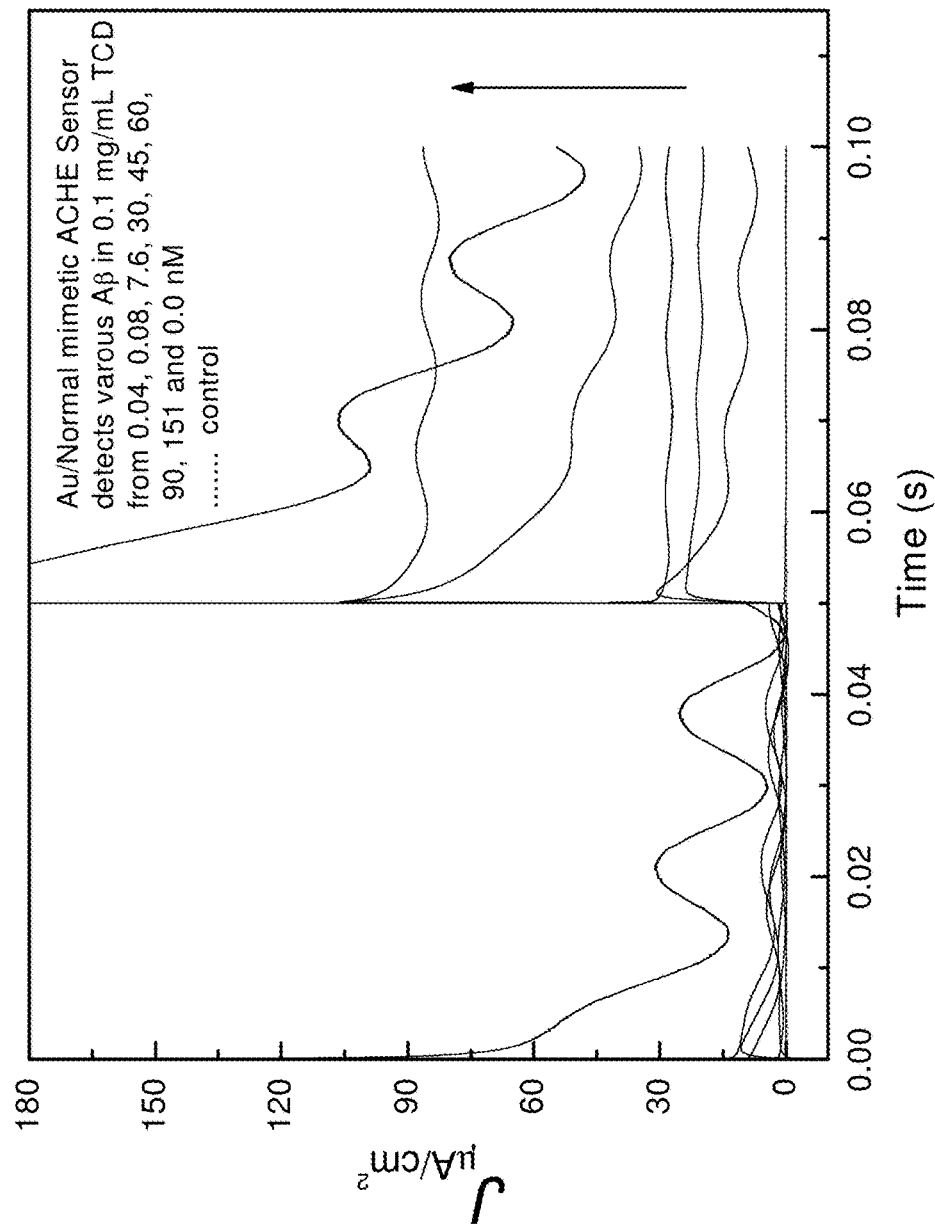
FIG. 8 illustrates CA curve profiles of Aβ affecting of the current intensity over concentration levels from 0.0 to 151 nM at 9 levels in the presence of 0.1 mg/mL TCD stabilizer in $DDH_2O$.
Figure 9:
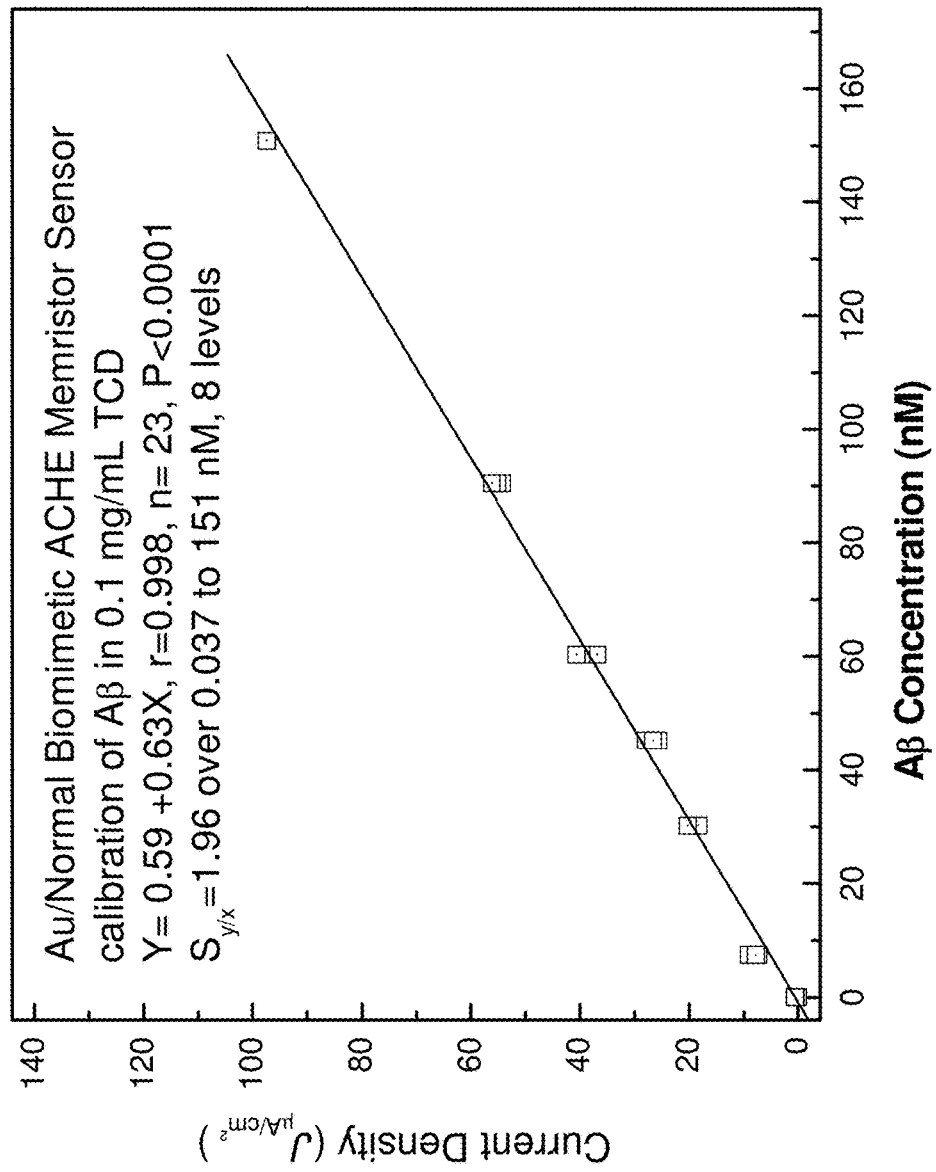
FIG. 9 depicts the calibration plot of current density vs. Aβ concentrations using the CA method.
Figure 10A:
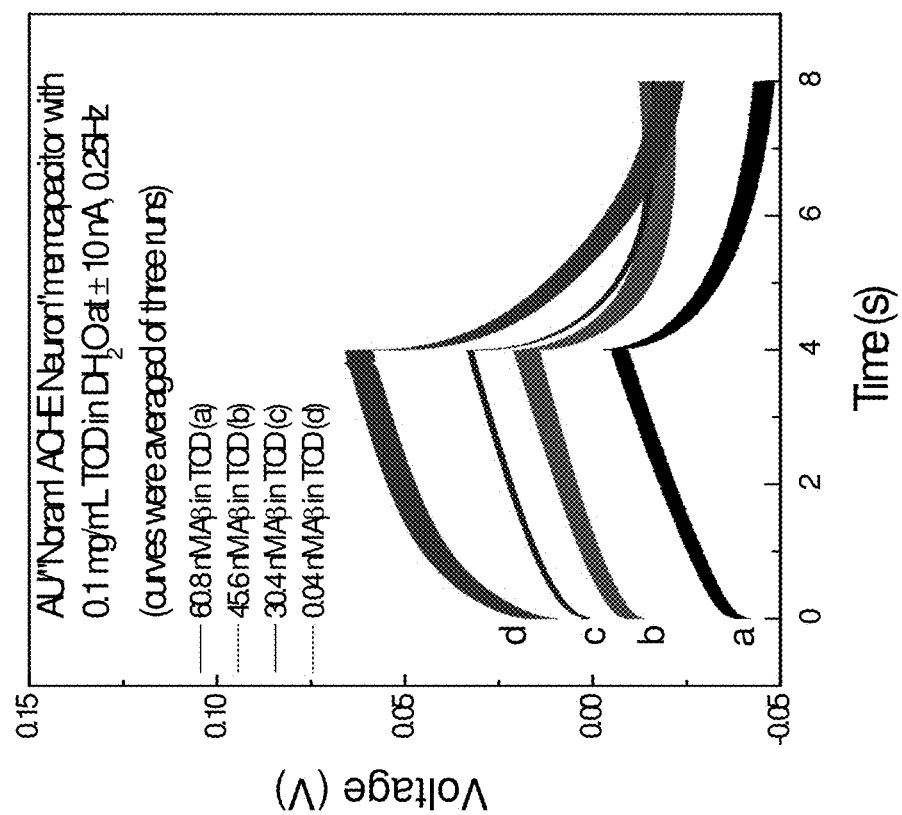
FIG. 10A depicts synapse voltage profile vs. time as shown for without Aβ in aqueous solution.
Figure 10B:
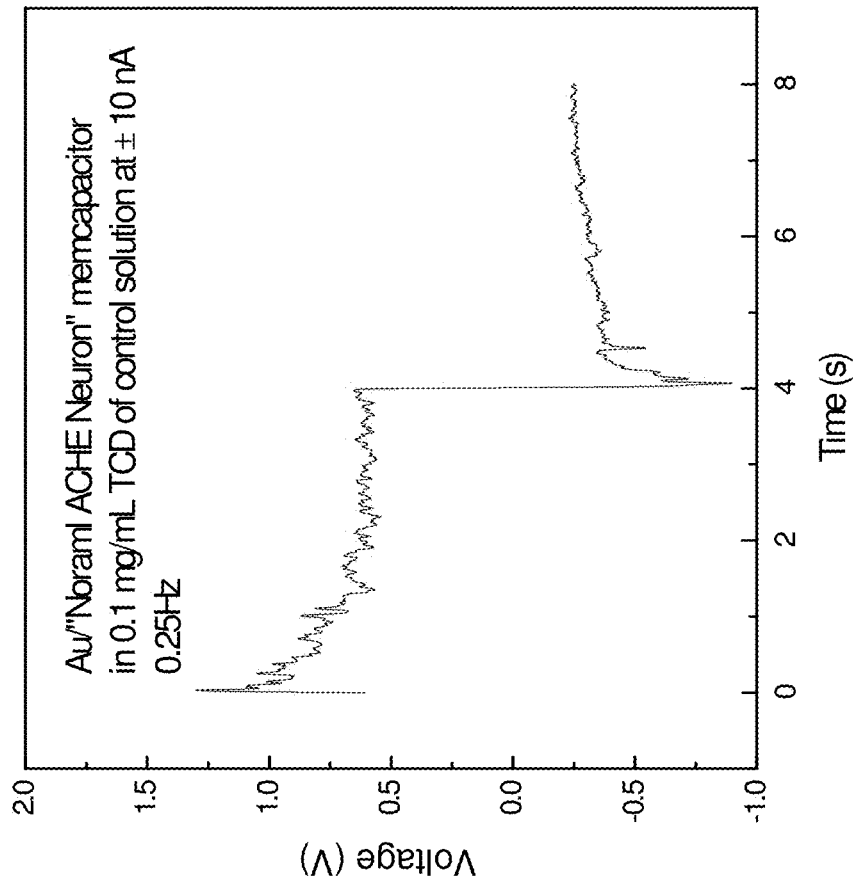
FIG. 10B depicts voltage profiles with Aβ in aqueous solution in the presence of 0.1 mg/mL stabilizer TCD with Aβ concentrations change from zero to 0.04 nM, 30.4 nM, 45.6 nM, 60.8 nM at ±10 nA and 0.25 Hz, respectively, and each sample run triplicates at room temperature.
Figure 11B:
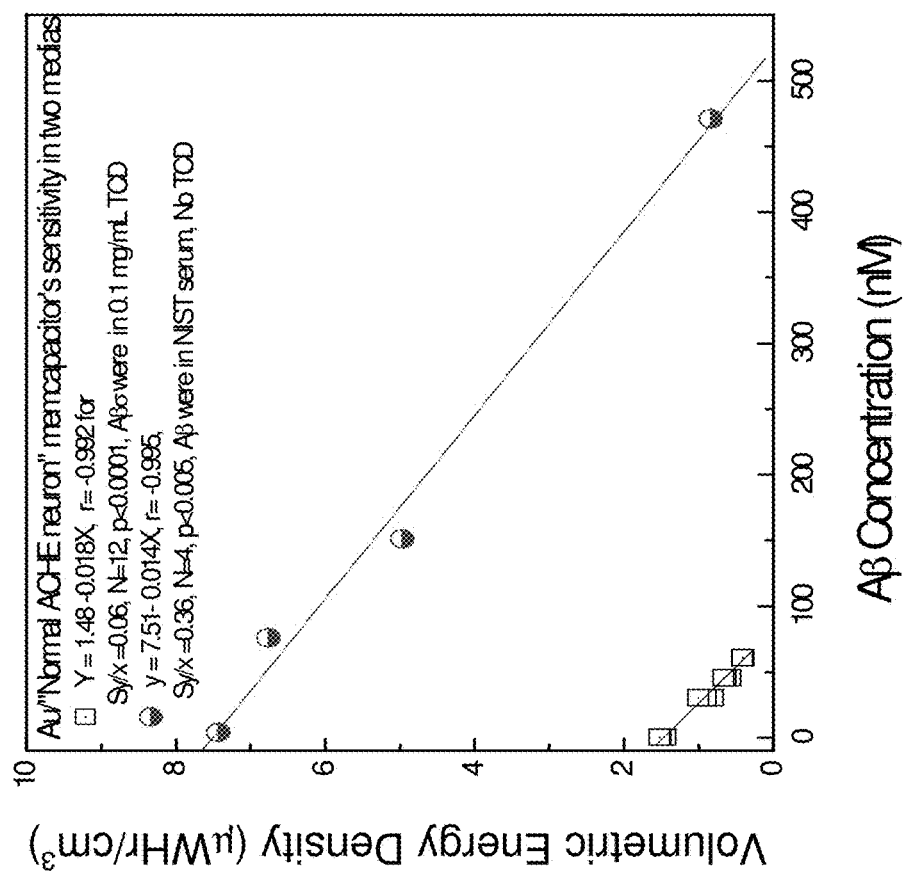
FIG. 11B depicts the calibration curves of volumetric energy density vs. Aβ concentration over 3.8 nM to 471 nM for using NIST serum media and over 0.04 nM to 60.8 nM for using water as media, respectively.
Figure 11A:
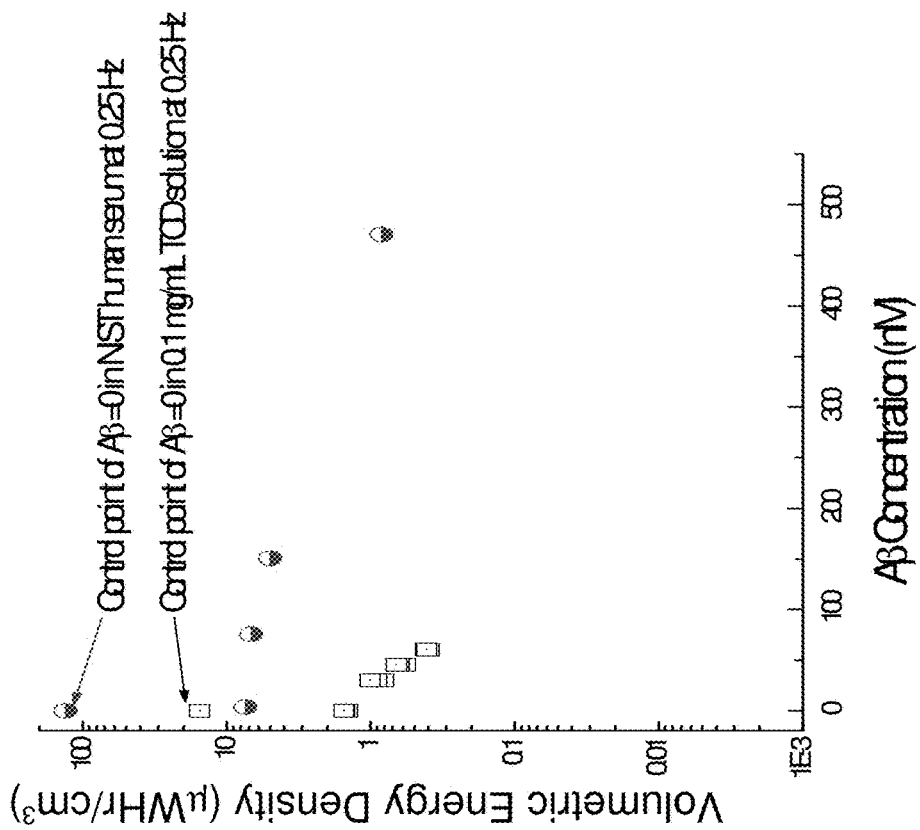
FIG. 11A illustrates the experimental data points of volumetric energy density vs. Aβ concentration from zero to 471 nM in NIST serum (Red) without a stabilizer TCD, and in water with 0.1 mg/mL stabilizer TCD (black).
Figure 12B:
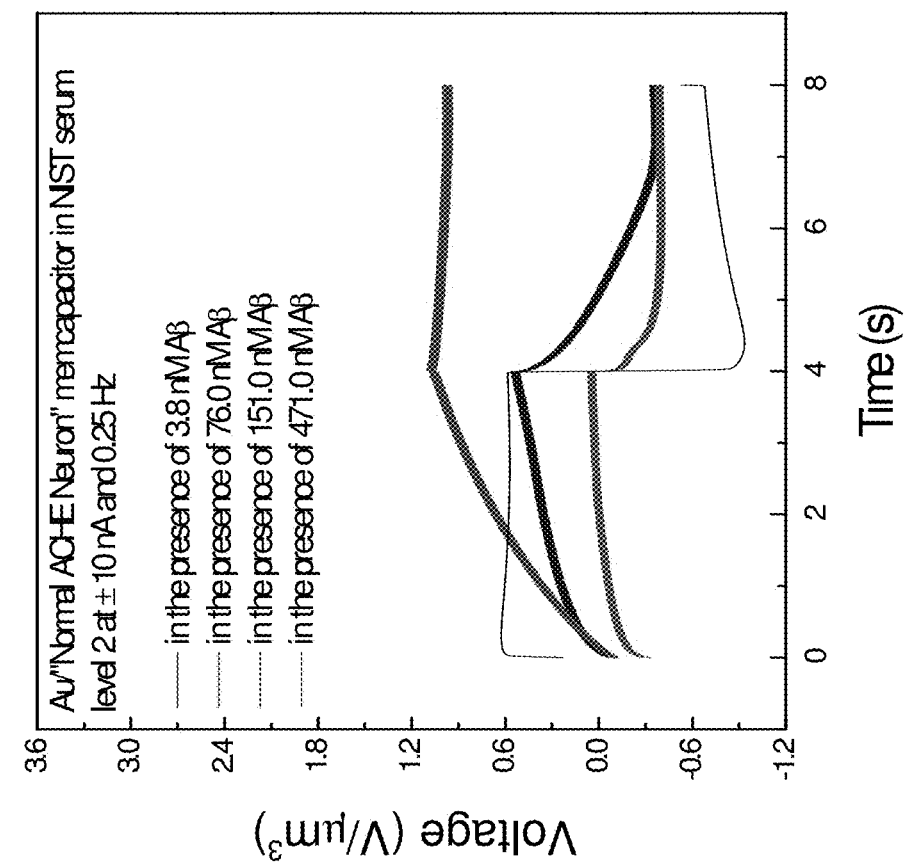
FIG. 12B depicts synapse voltage profiles using DSCPO method using NIST SRM965A serum samples in the presence of Aβ concentrations from 3.8, 76, 151, to 471 nM, respectively at ±10 nA at 0.25 Hz.
Figure 12A:
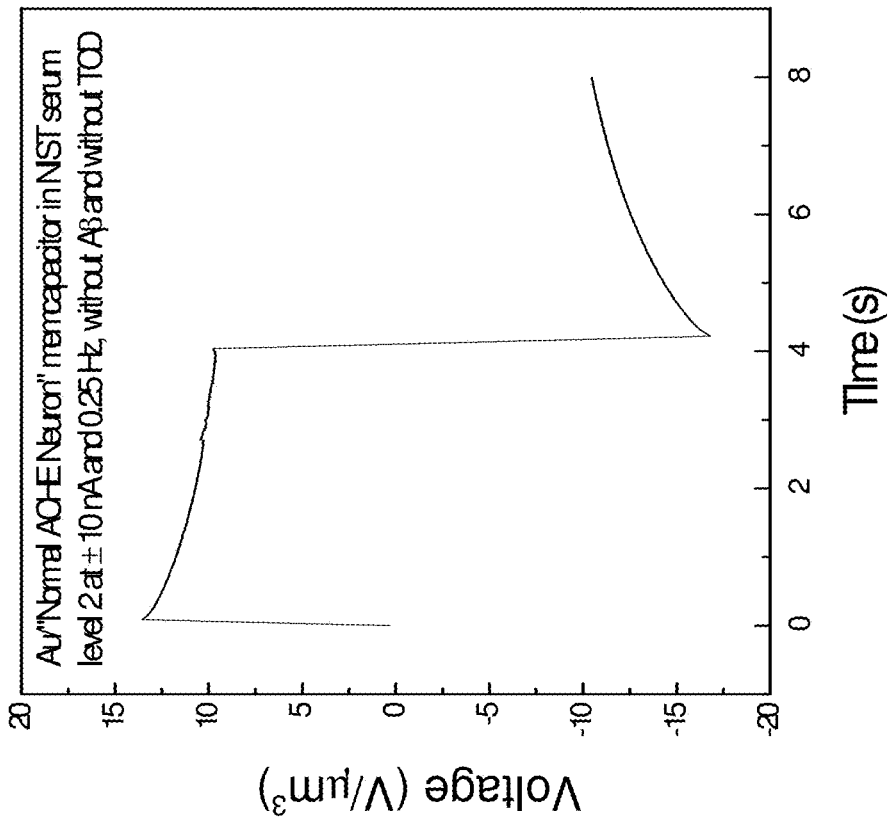
FIG. 12A depicts synapse voltage profile using DSCPO method using NIST SRM965A serum samples for without spiking Aβ and without TCD, at ±10 nA at 0.25 Hz.
Figure 13:
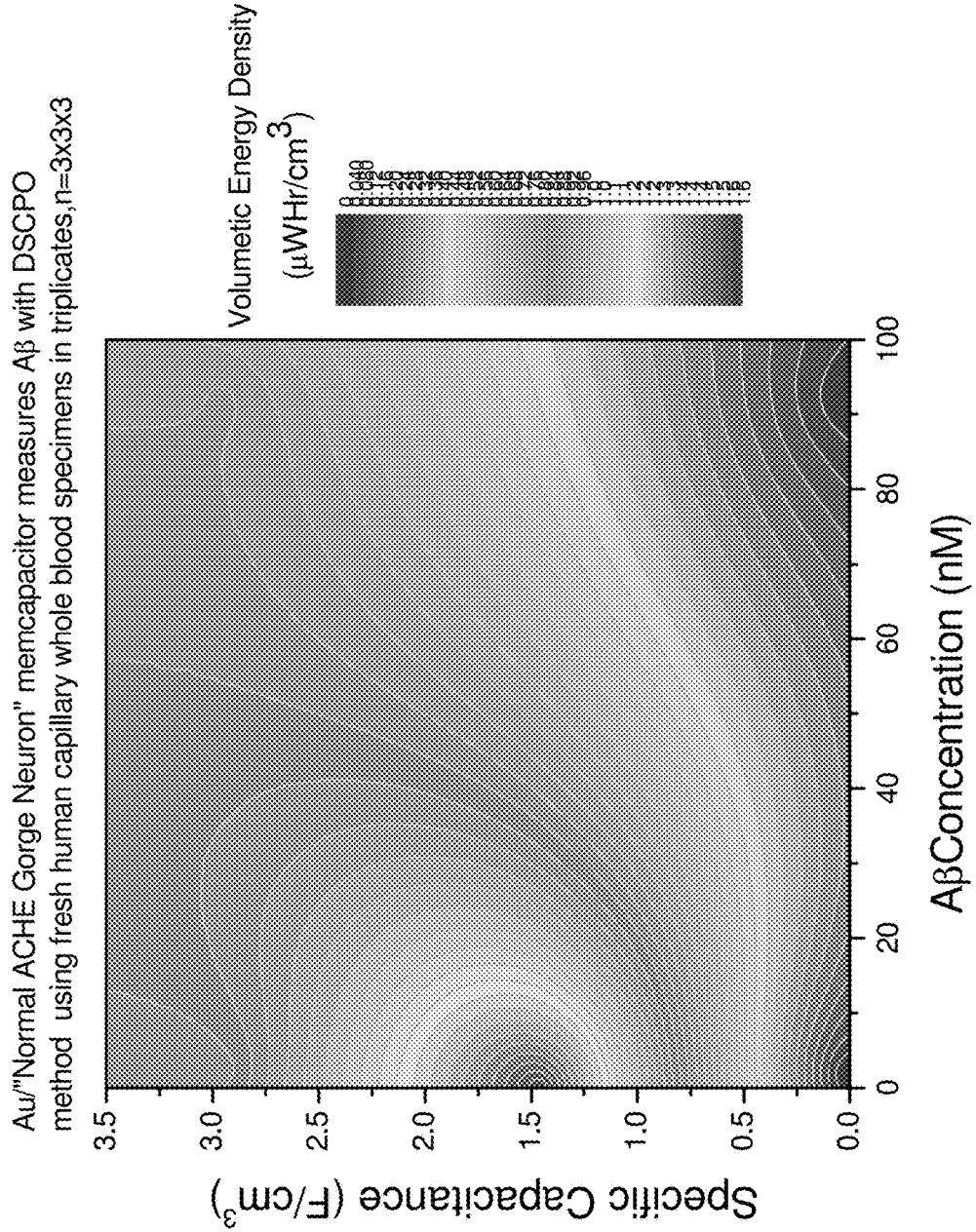
FIG. 13 depicts the voltage sensor's contour factor map between the specific capacitance as y-axis, the Aβ concentration as x-axis and the volumetric energy density as z-axis using human finger capillary whole blood specimen samples. Each sample was measured in triplicates.
Figure 14:
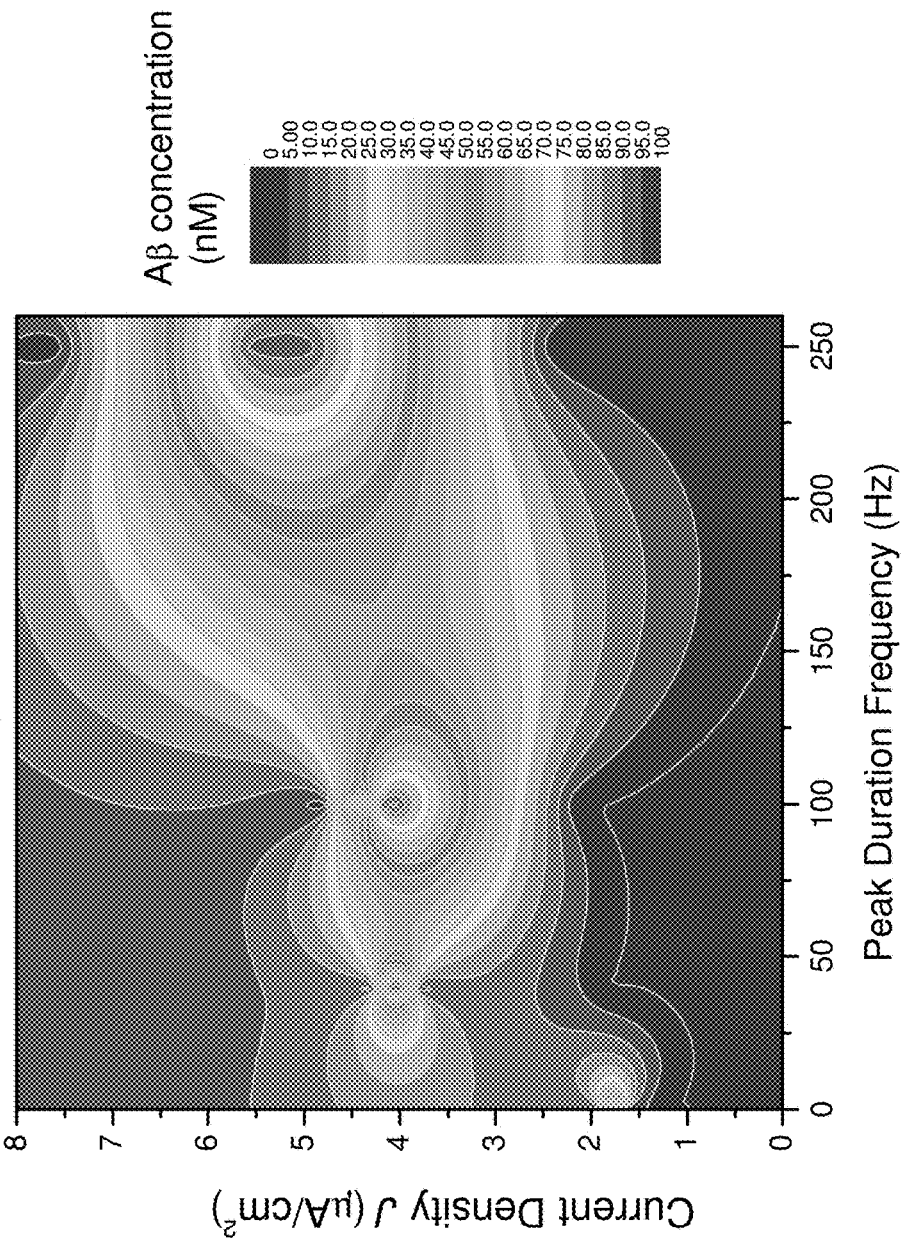
FIG. 14 depicts the CA sensor's contour factor map between the current density as y-axis, the peak duration frequency as the x-axis, and the Aβ concentration as the z-axis using human finger capillary whole blood specimen samples. Each sample was measured in triplicates.

Device 1's characteristic is a TSC/QMC device. The JJ supercurrent at zero-voltage was observed using NIST human blood serum samples for with or without spiked collagen over concentration from 1 ng/mL to 200 ng/ml at the innate state as shown in the i-V curves in FIG. 24A (1.0 to 200 ng/mL) and FIG. 10B (1.0-100 ng/mL) by the CV method compared with the control shown in the insert figure. FIG. 24A and FIG. 24B show the current intensity increased as collagen-1 concentration increase at zero-voltage in room temperature at B=0, and the quantized dI/dV conductance increased as the collagen concentration increase shown in FIG. 24C. The JJ current intensity of the biomimetic activated state of MMP-2 in Device 1 was observed in PBS shown in FIG. 25A compared with PBS control having hysteresis characteristics shown in the insert; with the quantized conductance curve shown in FIG. 25B compared with that of control was in the insert. The observed different results of the quantized conductance in the presence of collagen at the circular JJ in FIG. 24C and FIG. 25B in two different states between an innate and an activated MMP-2 state in difference media, may indicate the activated state promoted a strong super conductance than the innate state; collagen played an important role in both media at both states, as a superconducting promoter and as a sensing analyte. It has been shown in our prior works that the well-aligned cyclodextrin donut-like cavities formed large nanopore toroidal wells with dipole polarized circular current flow in opposite directions induced a non-ferromagnetic field [22-24].

Example 7—Evaluation of the Topological Superconductor/Quantum Memristor (TSC/QMR) Device 2 in Superconductivity/Memristivity The TSC/QMR Device 2. Device 2 utilized the first bottom layer of biomimetic CHAT as the pseudo-TSC layer under the assumption that injection of collagen-1 will promote direct super JJ circular current flow, plus the top second layer of bM-β-DMCD/TCD/PEG/PVP/$ZnCl_2$ without cysteine formed an activated biomimetic MMP-2 . . . CHAT relay tunnel with collagen-1 as the insulator layer and formed an S-I-S device, because the cross-linked polymer units repeated, wherein the device 2 has $SIS_n$ structures. Because the CHAT regulates the MMP-2 function and activity [22], FIG. 26A revealed the JJ super current was greatly increased at zero-voltage in the presence of 50 ng/mL collagen-1 and 50 ng/mL MCD in PBS solution compared with the PBS control and the MCD control as "a" and "b", while "c" is the one with collagen-1. The insert is the enlarged view of PBS control for 10 consecutive scans. The insert figure depicts the hysteric i-V curve of the control at 300 Hz scan rate. FIG. 26B depicts the quantum conductance density per superlattice in the presence of collagen which is 34-fold higher compared with the control. It is evident that the relay-enhanced the JJ supercurrent in the presence of 50 ng/mL collagen-1 and 50 ng/mL MCD when the large and small "donuts"-toroidal rings—alignment was in a place that promoted cooper pairs hopping at the junction tunnel.

Device 2 utilized the first bottom layer of biomimetic CHAT as the pseudo TSC layer under the assumption that direct super JJ circular current flow will be promoted by the presence of collagen-1, and with the top layer of -bM-β-DMCD/TCD/PEG/PVP/$ZnCl_2$,—an activated biomimetic 3D collagen-1 . . . MMP-2 . . . CHAT relay tunnel may form an SIS/SIN device with the TSC/QMR function peak at zero-potential. Because the CHAT regulates the MMP-2 function and activity [21], FIG. 26A revealed that the JJ super current greatly increased at zero-potential compared with the controls, and the enlarged view of the PBS control shown in the insert with the hysteric i-V curve indicated the memristivity of the nature of Device 2. FIG. 26B depicts the quantum conductance density per superlattice in the presence of collagen-1 which is 34-fold higher compared with the control. Device 2's quantum conductance density per superlattice is $3.1 \times 10^{10}$, 13 and 1.33-fold higher than that of activated Device 3 at 1 Hz, 1 kHz, and 10 kHz, respectively as shown in FIG. 28H based on curves displayed in FIG. 28B.

Example 8—the Super Current of the Activated TSC/QMC Device 1 have Wide Superconducting Bands in the Presence of Collagen-1

FIG. 27A depicts the zero-voltage superconducting peak of the activated Device 1 in the presence of 50 ng/mL collagen-1 and 50 ng/mL MCD in PBS 7.4 solution at scan rate 300 Hz over 15 mV to −50 mV, that was based on the i-V curves came from FIG. 25A. FIG. 27B depicts the special trajectory of the superconductive band of ±70 S vs. supercurrent in the range of ±100 mA and in the potential range over 20 mV to −25 mV. FIG. 27C depicts the 3D special location of the zero-voltage peak vs. supercurrent and vs. potential between 20 mV and −60 mV. FIG. 27D depicts the image of the brightest wide superconducting energy bands at the zero-bias of the activated Device 1 showing the coherent Cooper-pair crossover the barrier and also shows the single-electron tunneling bands in deemed light in the negative potential field under an external magnetic field=0 condition, that indicates the characteristics of the Josephson ring vortex effect.

Example 9—Evaluation of the Innate Protein Superconductive/Memristive Device 3

The Native Protein Device.
The native MMP-2 protein has two states: an innate state with the cysteine "on" and an activated state with the cysteine "off". FIG. 28A depicts i-V profiles of the innate Device 3 in PBS solution with scan rate from 1 Hz to 10 kHz. FIG. 28B depicts i-V profiles of the activated protein Device 3 in PBS solution over 1 Hz to 10 kHz. FIG. 28C depicts the i-V profiles of the innate Device 3 in the presence of various collagen-1 concentrations from 500 fg/mL to 25 ng/mL compared with the PBS control solution at 300 Hz scan rate. The innate MMP-2 Device 3 shows no superconductivity when spiked with 500 pg/mL collagen-1 concentration at 300 Hz depicted in FIG. 28C compared with the i-V profiles shown in FIG. 28A and FIG. 28B, respectively. However, hysteresis curves occurred in lower collagen concentration. The transformation from hysteresis to "pseudo superconducting" peaks was observed when concentration increased from 0.5 pg/mL to 0.5 ng/mL as shown in FIG. 28C for the innate Device 3 and with an enlarged view shown in FIG. 28G. FIG. 28B depicts the activated Device 3 having the JJ tunneling current at very low 1 Hz and high 1 kHz and 10 kHz in PBS with phase exchange and oscillation occurred. FIG. 28D depicts the i-V curves of the activated Device 3 in the presence of various collagen-1 concentrations compared with controls at 300 Hz.

FIG. 28E depicts the activated Device 3 communicates with collagen-1 in a superconducting way upon increased spiked concentration in human capillary blood specimen samples over 50 pg/mL to 100 ng/mL at 300 Hz compared with the human capillary serum control. FIG. 28F shows there is an inverted relationship between the collagen concentration and the JJ current; while the location of the peak observed is closer at the zero-voltage trajectory using human capillary blood serum when concentration increased from 50 pg/mL to 100 ng/mL at 300 Hz. FIG. 28G depicts the detail i-V profiles of FIG. 28E showing the zero-voltage peaks. The memristivity was observed over the scan rate change from 1 Hz to 1 kHz in 7 levels for Device 3 at the innate state. The electrochemical potential distance between the direct electron-transfer $(DET)_{red}$ peak to $DET_{ox}$ peak observed is in an exponentially accelerating apart manner as the scan rate increases having a first-order rate constant of 3.94 $(Hz)^{-1}$ far away from each other, this indicates in the absence of collagen, the memristive device is highly bidirectional polarized and the increased circular current intensity is exponentially proportional to the scan rate increase herein the net power is exponentially increased from 1 Hz up to 300 Hz. The charge of the peaks carried also followed the exponential increase pattern except at 1 kHz, the charge was drastically reduced shown in FIG. 28A. This phenomenon observed was the typical memristive device behavior and agreed with the literature [24]. At 10 kHz, the sine wave oscillating was observed. Superconductivity at 1 Hz might offer a benefit to infants' declarative memory consolidation in neuronal bidirectional circuitry development; because infants spend 16 hours per day asleep with half of that time at the slow wave sleep (SWS) stage from 0.5-2 Hz frequency [33-34]. FIG. 28H depicts the oscillation zero-voltage peaks of the activated Device 3 in PBS control solution at 1 Hz, 1 kHz, 10 kHz, respectively. FIG. 28I depicts the plots of the current intensity change between $DET_{red}$ and $DET_{ox}$ peaks vs. scan frequency (1 to 10 kHz) between the innate and the activated state, respectively. The activated state of Device 3 has both a 50 and 10-fold increase in current intensity compared to the innate state for $DET_{red}$ and $DET_{ox}$, respectively. Activated Device 3 has no zero-potential conductance at 300 Hz. It verified the fact that the large and small "donuts" or toroidal rings' alignment in the superlattice promotes the cooper pairs' hopping with the holes at the junction tunnel.

Example 10—Quantitation of Collagen-1 by the CV Method

FIG. 29A depicts the $DET_{red}$ and $DET_{ox}$ peak intensity exponentially increase/decrease vs. collagen-1 concentration, respectively over 1-200 ng/mL that was based on the CV profiles obtained in FIG. 24A and FIG. 24B on the innate Device 1 compared with the control using NIST human serum samples. Activated protein Device 3 has the CV profiles shown in FIG. 28E and FIG. 28G using human capillary serum specimens having 13% signal intensity over 50 pg/mL to 100 ng/mL compared with Device 1. FIG. 28F depicts the current has an exponential decay relationship as the collagen-1 concentration increase. FIG. 29B depicts a plot of the innate Device 3 having a linear range from 0.5 pg/mL to 0.5 ng/mL in PBS based on i-V curves in FIG. 28C. FIG. 29C depicts the trend of the electrochemical potential of $DET_{red}$ and $DET_{ox}$ peaks moves as a function of concentrations of collagen-1 over 0.5 pg/mL to 25 ng/mL of the innate Device 3 according to the FIG. 28C described.

Example 11—The Superconductive-Memristive Switches Under Extremely Low Collagen-1 Concentration for the Innate Device 1

It was our first observation that the superconductive-memristive switches coexist in a JJ toroidal vortex without an external magnetic field applied at room temperature under an extreme low collagen-1 concentration 0.5 pg/mL in a fixed scan rate 300 Hz in NIST serum upon consecutive multiple cycles of scans. FIG. 30A depicts the innate Device 1 in 0.5 pg/mL collagen-1 at the first scan cycle with both, superconducting current and hysteresis point located at zero-potential. The insert shows the hysteresis point at zero-potential, while located in the superconducting band. FIG. 30B depicts the second scan cycle; FIG. 30C depicts the third scan cycle; FIG. 30D depicts the fourth scan cycle; FIG. 30E depicts the fifth scan cycle and FIG. 30F depicts the control of NIST serum sample with pure memristive characteristics. This device will be found wide utilities in supercomputing with memory and no energy dissipation.

Example 12—Embedded Fractional Phase Change Promotes the Transformation from Memristive Sensing to JJ Toroidal Vortex Superconducting Reducing of the quantum energy gap between two superconducting peaks at the edge of ±2Δ value is very important, because superconducting peaks are occurring in the quantum gap range ≤±3 mV. Research groups reported some approaches for reducing the gaps [37]. FIG. 29C depicts the potential trajectory trends of the DET peaks as the collagen-1 concentration increase from 0.5 pg/mL to 25 ng/mL of the innate Device 3 in PBS solution at 300 Hz that were based on the i-V profiles in FIG. 28C. The results indicate the fact that the distance between $DET_{red}$ and $DET_{ox}$ peaks was shortened as the collagen-1 concentration increases, that implies collagen-1 promotes for reducing of the quantum energy gap between superconducting peaks ±2Δ value in order to make the transition from memristive to superconductive possible near the superconducting peaks working range at ≤±3 mV. FIG. 29C also implies collagen-1 drags bidirectional polarized sensor to the zero-bias and to be non-polarizable for superconducting purpose.

FIG. 30A depicts the innate Device 1 in 0.5 pg/mL collagen-1 using NIST human serum at 300 Hz at the first scan cycle with both, superconducting current and hysteresis point located at zero-potential. The insert shows the hysteresis point at zero-potential, while located in the superconducting band. FIG. 30B depicts the second scan cycle; FIG. 30C depicts the third scan cycle; FIG. 30D depicts the fourth scan cycle; FIG. 30E depicts the fifth scan cycle and FIG. 30F depicts the control of NIST serum sample with pure memristive characteristics. Its hysteretic cross point at v=0 with 10-fold higher JJ current than that of at 200 ng/mL, that indicates in extreme low collagen concentration, the quantum superconductor/memcapacitor device also can serve as a memristive device; hence not surprisingly we observed the quick phase change of the JJ wave during a 5 consecutive scan at 300 Hz compared with the NIST serum control at 300 Hz. The phenomenon may imply a blastocyst cell develops in a surprising way of topological quantum superconductive/memcapacitive/memristive properties in place when extra low collagen-1 communicates MMP-2 in the blood membrane.

Example 13—Quantitation of Collagen-1 by the Voltage Method

Quantitation of collagen-1 was conducted in three methods: a voltage method, a CA method and a CV method in two media: PBS solution and human serum samples. The voltage method and the CA method each sample run triplicates against the controls in the range over 0.5 pg/mL to 200 ng/mL. FIG. 31A depicts the curves of voltage vs. time at 0.25 Hz at ±10 nA over 0.5 pg/mL to 200 ng/mL collagen-1 concentrations against the control samples using Device 1 at the innate state in PBS solution. FIG. 31B depicts the calibration curve of action potential vs. collagen concentration, and it produced a linear regression equation Y=3.1−0.015x, r=0.995 (n=18), P<0.0001, Sy/x=0.12 over collagen-1 concentration 0.5 pg/mL to 200 ng/mL with a pooled relative sum of squares pure error (PRSSPE) of 2.0%.

The method accuracy and imprecision was studied through the recovery experiments on Device 1 compared with Device 3 by using pure NIST human serum specimens spiked with 4 levels of collagen-1 concentrations over 500 fg/mL to 200 ng/mL. Results obtained shown in FIG. 32A are the voltage profiles and FIG. 32B depicts the linear regression plot of measured collagen in PBS vs. that of in NIST2 serum over the studied range after included the serum control's collagen-1 concentration according to the standard curve. FIG. 33A presented is for the trend of the voltage in resting potential peaks over the same concentration range tested. FIG. 33B is the same as FIG. 31B. FIG. 33C depicts the cell energy density curve vs. collagen-1 concentrations. The recovery results have an agreement of 92±0.03% over the studied range. The imprecision of the PRSSPE error was 0.3% (n=15). Device 2 and Device 3 have failed using the voltage method.

Example 14—The JJ Toroidal Vortex Characteristics

The hallmarks of the JJ characteristics are (1) at a DC voltage=0, $$I_s = I_c \sin(\Delta\varphi) \quad (1)$$

$I_s$ is the supercurrent, $I_c$ is critical current, $\Delta\varphi$ is the phase difference between the waves of two superconductors appears at the DC Josephson junction; (2) at a finite DC voltage, the phase change of the superconducting wave vs. time caused oscillating at the AC Josephson Junction, and is proportional to 2 $eV_{DC}$, i.e., $$\partial\varphi/\partial t \propto 2\ eV_{DC} \quad (2) \ [10\text{-}12].$$

FIG. 34 shows the trend of the comparison of the amplitude of the JJ super AC current among the three devices: the magnitude of the activated Device 1 in the PBS control solution is 29-fold and 260-fold higher than Device 2 and the innate Device 3, respectively by the Chronoamperometric method (CA) under zero-potential for each of the two steps with fixed 10 kHz data rate for each step. Device 2's super current magnitude is 9.5-fold higher than that of Device 3. A method has developed to quantify the Friedel-oscillation observed in the Example 5 and linked it with the results from the CA method under the double step zero-potential approach, herein the order of the Friedel-oscillation frequency among the three devices was Device 3>activated Device 1>Device 2, i.e., 83.33 Hz/peak>76.9 Hz/peak>55.56 Hz/peak, respectively. Under the same data rate, within the 0.8 s period, Device 3 has 66.7 peaks, the activated Device 1 has 61.5 peaks and Device 2 has 44 peaks. It was verified that our CHAT . . . biomimetic MMP-2 . . . collagen-1 approach has paved a road to reduce the JJ tunnel strong oscillation in order to enable detecting extremely low concentration of collagen-1 by the CA method, Device 1 and Device 3 were failed the CA method to detect collagen-1 due to the very strong oscillation in both, control solution and in the presence of collagen.

Another method used to characterize the JJ toroidal vortex is to use the DC potential amperometry (DCPA) method. FIG. 35A depicts DC curves vs. time under zero potential compared between Device 2 and the innate Device 3. The results indicate Device 2 has a higher eternal power for spontaneous producing an initial current ($-0.8\ \mu A$) at t=0, and an applied potential=0, vs. Device 3 which has a small and negligible eternal power with an initial rate of 0.28 nA/s went to an exponential drop to the s-s state, which is 148.6-fold weaker than Device 2. It is another example verifying Device 2's superconductivity is superior to Device 3. In general, under a non-zero applied DC voltage in a buffer solution, the current will exponentially drop to the steady-state (s-s) state at a definite time interval from the sensor in order to reach the equilibrium state from the non-Faraday current, but in contrast, Device 2's current goes up with an initial rate of 41.6 nA/s towards the cathode, which is a known electron pop-hop transport phenomena between the transition metal zinc and the $d_\pi$ from polymer receptors [30-31], i.e., cooper pairs quantum transport their electrons which are exchanged with holes of the receptors in the superlattice membrane. As Liao mentioned in his report, zinc metal coordinates well with the tetraphenylporphine nitrogen atoms better than Fe, Co, Ni, and Cu, because zinc's $d_{x2-y2}$ orbital energy significantly dropped, in favor of coordination with the $d_\pi$, i.e., π-cation radical, hence our experiment supports his finding that the $d_\pi$ orbital may dominate the electron relay [32]. FIG. 35B depicts DC current curves vs. time under zero potential compared between Device 1 and the innate Device 3, which indicates the innate Device 1 has an initial rate of 13.08 nA/s increase up to an exponential increase towards the cathode, which is 3.2-fold slower than that of Device 2.

The third method used to validate the activated Device 3's i-V profiles compared with the innate Device 3 is the CV method. FIG. 36 depicts the current intensity vs. scan rate compared between the $DET_{red}$, $DET_{ox}$ at the innate and the activated states of Device 3 in the PBS solution, respectively. The scan rate was over 1 Hz, 40 Hz, 200 Hz, 300 Hz, 1 kHz, and 10 kHz (n=6). The insert is the enlarged view of the innate state Device 3. The results indicate the intensity of the peak current at the activated state of $DET_{red}$ vs. scan rate has a linear sensitivity of 0.07 nA/Hz, which is 31.8-fold higher than that of the innate state, that has a non-linear first-order constant of 0.0022/Hz. That indicates Device 3 used extremely short time reached the s-s than Device 2. A similar trend was observed for $DET_{ox}$ between the activated vs. the innate Device 3.

Example 15—the Fractional Phase Change of JJ Toroidal Vortex Initiated Superconductivity Fractional Josephson vertices depends on the supercurrent loops created a magnetic flux in which the superconducting phase discontinuities [35]. The fractional Josephson effect predicted theoretically can be existed in the absence of an applied magnetic flux, which enables the efficient topological qubit readout [36], however, it was not observed. FIG. 37A depicts the phase changes of the i-V cures vs. scan rate of the innate state Device 1 in PBS solutions. FIG. 37B depicts the fractional phase changes of the innate Device 1 in PBS solution at 300 Hz. Not like Device 2 and innate Device 3, they are memristive in nature in the PBS solution at 300 Hz, the innate Device 1 has no observable DET peaks in the scan range from 1 Hz to 10 kHz in PBS solution, notably is the i-V curve at 300 Hz possessed the fractional phase change as shown in FIG. 37B. Oscillation was observed in 10 kHz in FIG. 37A. Therefore, the evidence of the innate Device 1 direct detects collagen-1 using the voltage method, presented in the following section and was initiated by the fractional phase change that leads to the memcapacitive characteristic and function. Nevertheless, the innate Device 1 in human blood media, its i-V curve has hysteresis function. Because the collagen-1 does present in human serum, it may change the nature of the i-V curve.

Example 16—Quantitation of Collagen-1 by the CA Method

Using the biomimetic "CHAT . . . MMP-2" direct electron relay approach, i.e., "Predator catfish . . . Brachyhypopomus electric fish" approach, we were able to reduce the strong Friedel-oscillation at the long-range JJ toroidal vortex compared with that of Device 1 and Device 3. We were able to directly detect collagen-1 in sub fg/mL under labeling-free and antibody protein-free and reagent-free conditions. FIG. 38A depicts the plots of current vs. time under $-0.3V$ applied potential over collagen-1 concentrations 5.0 fg/mL to 200 ng/mL compared with the control in PBS solution using Device 2. Inserts are the enlarged view of the profiles at low and high levels, respectively. All curves oscillating at the AC JJ were observed. FIG. 38B depicts the linear regression calibration curve of current density vs. collagen-1 concentrations over the linear range of 5.0 fg/mL to 100 ng/mL (6 levels) with the regression equation y=0.46+0.094x, r=0.997, Sy/x=0.299, p<0.0001. FIG. 38C depicts Device 2's exponential current increase pattern as the collagen-1 concentration increases, the curve is over 5.0 fg/mL to 200 ng/mL (9 levels) with a Detection of Limits (DOL) of 0.43 pg/mL/cm$^2$ (14 fg/mL for this sensor) with a relative percent of sum of squares pure error (RSSPE) of 0.05% at the high end and 0.5% at the low end, respectively.

Point Accuracy and Imprecision.

Point accuracy and imprecision was studied through the recovery experiments using spiked human fresh finger capillary blood (CPWB) serum specimens as controls spiked with 2 levels of collagen concentrations over 2.5 pg/mL to 166 ng/mL, and we compared the measured results with the calibration curve after subtraction of the currents from control serum samples. The recovery results were 96.4±3.4% and 97.9±0.73% with the imprecision of 4.9% and 0.8% at 2.5 pg/mL and 166 ng/mL level, respectively by the CA method. Due to the strong wave oscillation occur in both the PBS solution and the finger serum samples, Device 1 and 3 at both the innate and activated states were unable to respond to concentration changes of collagen-1 from 500 fg/mL to 100 ng/mL both in PBS and in human finger serum using the CA method under the fixed potential, respectively.

Example 17—Direct Label-Free and Antibody-Free Detection of Protein by the Innate Native Protein MMP-2 Device FIG. 39A depicts the i-V curves of Device 2's direct measurements of protein collagen-1 over 0.5 pg/mL to 5 ng/mL compared with the control in PBS solution at 200 Hz. FIG. 39B depicts an exponential decay relationship between the $DET_{OX}$ peak current and the collagen concentrations in PBS solution in a log scale. Device 2 has 1.2×10$^7$-fold increase in detection sensitivity and testing range compared with Device 3 at an innate state as shown in FIG. 40A in the i-V profiles and FIG. 40B in the calibration curve. However, it was shown in the first time that the native MMP-2 innate Device 3 was able to directly sense the presence of collagen-1 in 0.5 pg/mL to 0.5 ng/mL linearly without denaturing and without labeling, and that is due to the toroidal superlattice structure of the membrane, which stimulates the localized biological zinc atoms to become mobile and causes the Friedel-oscillation with functional groups in collagen-1 and in the polymers.

Example 18—Protein Concentration Change Impacts on Super-Positioning of Quantum States Protein concentration change impacting on super-positioning of quantum states was studied by comparing of the i-V curves for with or without collagen concentrations at a fixed scan rate. FIG. 41A shows the Activated Device 1 transformed its memristive state to a superconducting state at a higher protein concentration of 200 ng/mL in the PBS buffer solution under 300 Hz scan rate by closing the quantum energy gap between $DET_{red}$ and $DET_{ox}$. FIG. 41A depicts when collagen-1 concentrations lower than 200 ng/mL, covered 4 levels from 5 fg/mL to 50 ng/mL, were no superconductivity, and the memristive curves were shown in several collagen concentrations. FIG. 41B depicts the super-positioning of quantum states happened in the i-V curve among the states (0 V, −1), (0 V, 0) and (0V, +1) at zero-bias potential with 200 ng/mL collagen. Here "+1" means the supercurrent >0, "−1" means the supercurrent <0. It was observed the origin point was inside of the narrow barrier of ±Δ≤3 mV. FIG. 41C depicts the exponential increase relationship between the activated Device 1's $DET_{red}$ current and the collagen-1 concentrations from 50 fg/mL to 50 ng/mL. FIG. 41D depicts the trend of collagen-1 reduces the quantum energy gap of the potential difference between $DET_{red}$ and $DET_{ox}$ vs. collagen-1 concentration.

Example 19—Conclusions

We demonstrated the quantum superconductive//memristive and the quantum superconductive/memcapacitive devices promoted superconductivity, quantum memristivity, and quantum memcapacity. Device 2's quantum conductance density per superlattice is 3.1×$^{10}$10, 13 and 1.33-fold higher than that of activated Device 3 at 1 Hz, 1 kHz, and 10 kHz, respectively, and it can directly detection of sub fg/mL collagen-1 with higher sensitivity and wider range compared with Device 3 at innate and activated states. We also reported the innate Device 3 can directly sense 0.5 pg/mL to 500 pg/mL collagen-1 without denaturing procedures. The quantum superconductive/memristive technology having external magnetic field-free conditions and performed well at room temperature may find broad applications in supercomputing, artificial intelligence, energy, medical sensing, artificial antibody, and military, various areas in the future.

We demonstrated the innate Device 1 solely depends on the fractional quantum phase change to induce quantum superconductivity/memcapacity in PBS solution, that works superior over Device 2 and 3 for sensing of voltage change in the presence of sub pg/mL collagen-1 to 200 ng/mL with good results of recovery using human serum samples. We also demonstrate the toroidal vortex topological nonconventional superconductive devices with various superlattice structures having the Friedel-oscillation are workable at room temperature without an applied external magnetic field. The devices worked in different media by using collagen-1 as an insulator and as an analyte. Without denaturing of a protein, the biomimetic MMP-2 superconductors offered significant benefits in both, superconducting and sensing, compared with the reference device.

REFERENCES

[1]. J. K. Kular, S. Basu and R. I. Sharma, The extracellular matrix: structure, composition, age-related differences, tools for analysis and applications for tissue engineering, J. Tissue Engineering 5, 1-17, 2014.

[2]. T. Watanabe-Nakayama, M. Itami, N. Kodera et al., High-speed atomic force microscopy reveals strongly polarized movement of clostridial collagenase along collagen fibrils, Scientific Reports, 6:28975, 2016.

[3]. M. F. Najafi, S. Zahri, F. Vahedi et al., Which form of collagen is suitable for nerve cell culture? Naural Regeneration Research, 8(23), 2165-2170, 2013.

[4]. W. Mckleroy, T-H Lee and K. Atahai, Always cleave up mess: targeting collagen degradation to treat tissue fibrosis, Am J Physiol Lung Cell Mol Physiol 304, L709-L721, 2013.

[5]. E. Takai, K. D. Costa, A. Shaheen et al., Osteoblast elastic modulus measured by atomic force microscopy is substrate dependent, Annals of Biomedical Engineering, 33 (7), 963-971, 2005.

[6]. B. H. San, Y. Li, E. B. Tarbet, S. M. Yu, Nanoparticle assembly and gelatin binding mediated by triple helical collagen mimetic peptide, ACS Applied Materials and Interfaces, 8, 19907-19915, 2016.

[7]. E. Seo, K. W. Seo, J-E Gil, Y-R Ha, et. Alo., Biophysiochemical properties of endothelial cells cultured on bio-inspired collagen films, MioMed Central Biotechnology, 14:61, 2014.

[8]. E. T. Chen, J. T. Thornton, S-H. Duh and P. T. Kissinger, Organic Nanobiomimetic Memristive/Memcapacitive Devices Ultrasensitive Direct Detect Matrix Matelloproteinase-2 in Human Serum, Biotech, Biomaterials and Biomedical, TechConnect Briefs, 271-274, 2017.

[9]. E. T. Chen, J. T. Thornton, S-H. Duh And P. T. Kissinger, Observation of Fermi Arc Surface States Induced by Organic Memristive/Memcapacitive Devices with a Double-Helical Polarized Single-Wall Nanotube Membrane for Direct Chelating with Matrix Matelloproteinase-2, Sensors and Transducers Journal, 214(7), 69-84, 2017.

[10]. Editors E. Wolf, G. Arnold, M. Gurvitch and J. Zasadzinski, Preface, Josephson Junctions, History, Devices, and Applications, Pan Stanford Publishing Pte, Ltd, 2017.

[11]. S. Frolov, Quantum Transport, www.sergeyfrolov.wordpress.com/teaching

[12]. S. Kivelson, Superconductivity and Quantum Mechanics at Micro-Scale, Stanford University. www.youtube.com/watch?v=yx666k2xH8E

[13]. E. Grosfeld And A. Stern, Observing Majorana bound states of Josephson vortices in topological superconductors, PNAS, 108(29), 11810-11814, 2011.

[14]. X. Liu, X. Li, D-L Deng, X-J Liu, and S. Das Sarma, Majorana Spintronics, arXiv, 1602.08093v2, 2016.

[15]. J. Li, T. Neupert, B. A. Bernevig, A. Yazdani, Manipulating Majorana zero modes on atomic rings with an external magnetic field, Nature Communications, 7:10395, 2016.

[16]. www.en.wikipedia.org/Josephson vortex

[17]. J. Salmileto, F. Deppe, M. DiVentra, Quantum memristors with superconducting circuits, Scientific Reposrts, 7:42044, 2017.

[18]. C. Guarcello, P. Solinas, M. DiVentra and F. Giazotto, Solitonic Josephson-based meminductive systems, arXiv: 1610.06807v1, 2016.

[19]. M. Ternes, M. Pivetta, F. Patthey, and W-D Schneider, Creation, electronic properties, disorder, and melting of two-dimensional surface-state-mediated adatom, Progress in Surface Science 85, 1-27, 2010.

[20]. E. T. Chen and H. L. Pardue, Analytical applications of catalytic properties of modified cyclodextrins, Anal. Chem, 65(19), 2583-2587, 1993.

[21]. S. Davari, S. A. Talaei, H. Alaei, M. Salami, Probiotics treatment improves diabetes induced impairment of synaptic activity and cognitive function: behavioral and electrophysiological proofs for microbiom-gut-brain axis, Neuroscience, 240, 287-296, 2013.

[22]. M. D Pickett, G. Medeiros-Ribeiro and R. S Williams, A scalable neuristor built with Mott memristors, Nature Materials, 2013, 12, 114-117.

[23]. M. Suri and B. Desolvo, Advances in neuomorphic memristor science and applications, Editors R. Kozma, RE Pino, GE Pazienza, Springer publisher, 4, 2012.

[24]. M. D Ventra, Y. V Pershin, On the physical properties of memristive, memcapacitive, and meminductive systems, Nanotechnology 24, 255201, 2013.

[25] E. T. Chen, J. T. Thornton and Jr C. Mulchi, Mapping Circular Current for a Single Brain Cancer Cell's Spatial-Temporal Orientations Based on a Memristor/Memcapacitor, Sensors & Transducers, 183(12), 72-83, 2014,

[26]. S-H. Duh, J. Thornton, P. T. Kissinger and E. T. Chen, Nanobiomimetic memristor/memcapacitor devices used for direct and reagent-less detection of sub pM acetyl coenzyme A in milks, Sensors, Diagnostics & Imaging, TechConnect Briefs, 4, 136-139, 2016.

[27]. S-H. Duh, J. Thornton, P. T. Kissinger and E. T. Chen, Human Milk Shows Immunological Advantages Over Organic Milk Samples For Infants In the Presence of Lipopolysaccharide (LPS) in 3D Energy Maps Using an Organic Nanobiomimetic Memristor/Memcapacitor, Sensors and Transducers Journal, 203(8), 57-68, 2016.

[28]. E. T. Chen, J. Thornton, P. T. Kissinger and S-H. Duh, The Advantages of Human Milk Recognize the Spatiotemporal Locations of Toxins and Intelligently Bypass Them by Forming a Hummingbird-Like Hovering Neural Network Circuitry Based on an Organic Biomimetic Choline Acetyltransferase Memristor/Memcapacitor Prosthesis, Sensors and Transducers Journal, 203(8), 69-83, 2016.

[29]. E. T. Chen, Nanostructured Biomimetic Sensing And Energy Storage: Organic Memristor/Memcapacitors was published in the book of *Dekker Encyclopedia of Nanoscience and Nanotechnology, Third Edition*, DOI: 10.1081/E-ENN3-120054061, Jan. 18, 2017. www.crcnetbase.com

[30] J. E. Redman, Solution, surface and solid state assembly of porphyrins, University of Cambridge, 2000.

[31]. R. V. Slone and J, T. Hupp, Synthesis, characterization, and preliminary host-guest binding studies of porphyrinic molecular squares featuring fac-tricarbonylrhenium(1) chloro corners, Inorg Chem 36(24), 5422-5672, 1997.

[32]. M. S. Liao, Electronic structure and bonding in metal porphyrins, metal=Fe, Co, Ni, Cu, Zn, Utah State University publication, 2002.

[33]. A. E. Power, Slow-wave sleep, acetylcholine, and memory consolidation, *PNAS,* 101, 7, 1795-1796, 2004.

[34]. Slow-wave sleep, www.wikipedia.org

[35]. Fractional Josephson vertice.wikipedia.com

[36]. X. Liu, X. Li, D-L Deng et al., Majorana spintronics, arXiv: 1602.08093v2, 2016.

[37]. J. Chen, P. Yu, J. Stenger et al., Experimental phase diagram of zero-bias conductance peaks in superconductor/semiconductor nanowire devices, Science Advances, 3, e1701476, 2017.

What is claimed is:

1. A Josephson toroidal vertex quantum superconductive/memristive device comprising
    (a) a first electrode has a first layer of an organic superconductive membrane on top, which made of arrays of the nano-islands structured organic conductive membrane by self-assembling cross-linked polymers;
    (b) a second layer membrane comprising of an organometallic superlattice membrane, which made of cross-linked triacetyl-β-cyclodextrin (TCD), polyethylene glycol diglycidyl ether (PEG), poly(4-vinylpyridine) (PVP), bis-imidazole substituted dimethyl-β-cyclodextrin (bM-β-DMCD) and embedded with zinc chloride horizontally laid on the top of the first layer;
    (c) materials of PEG, TCD, PVP, and PEG cross-linked vertically oriented on the surface of the first electrode;
    (d) a channel in the second membrane comprises of nanostructured parallel waves;
    (e) a direct electron-relay between a biomimetic choline acetyltransferase (CHAT) . . . biomimetic matrix metalloproteinase-2 (MMP-2) . . . collagen-1 . . . Zn formed chelating coordinating bounds in order to facilitate an "On" and "Off" switch at zero-bias;

(f) at least one or two of the superconductor's membranes having Friedel-oscillation in the superlattice toroidal membranes.

2. The use of a device according to claim 1, applied a finite DC voltage onto a long-range Josephson junction of toroidal vertices, i.e., the Au/(SIS)n/Au assembly: Au/nano-island superconductor-insulator-arrayed toroidal superlattice/Au S-I-S superconductor boundaries, the fermions of cooper pairs hop through the junctions caused an oscillating due to phase change of the superconducting waves.

3. According to claim 2, wherein the oscillating superconducting waves are as functions of time and the past state of memory.

4. According to claim 3, wherein the oscillating superconducting waves have a circular fashion that the quantum conductance is quantized and proportional to 2 $eV_{dc}$.

5. According to claim 2, wherein when applied a DC voltage=0, the supercurrent observed is exponentially proportional to the increase of the collagen-1 concentrations observed at the zero-potential superconducting peaks in sinusoidal waveforms.

6. According to claim 2, wherein at DC voltage=0, the super conductance values increase as the collagen-1 concentration increased.

7. According to claim 1, wherein an organic material collagen-1 spiked in a biological fluid or an aqueous solution forming a matrix as a dielectric insulating layer.

8. According to claim 1, wherein the second superlattice layer has arrays single-wall curvature nanotubes with a diameter 200 nm and average length 2-3 μm forming array lattice with an average area of the lattice occupying 21-25 μm$^2$, while zinc atoms on the edge or at the center of the lattice in that the device covered with 1.5×10$^5$ uniform oriented superlattice on top of the nano-island layer.

9. According to claim 1, wherein the quantum superconductive/memristive device works relying on the spontaneous produced open circle potential energy to overcome the drawbacks of the toroidal vertex energy for suppressing the JJ super current, herein the device works at the external magnetic field-free, i.e., external H=0 condition.

10. According to claim 1, wherein the organometallic polymer materials used for fabricating the second superlattice layer membrane can also be directly fabricated on a bare gold electrode with an extra component of L-cysteine cross-linked with the organometallic polymer materials in order to bear superconductive/memcapacitive characteristics.

11. According to claim 10, wherein the quantum superconductive/memcapacitive device in its innate state and activated state (with or without L-cysteine) demonstrated its quantum conductance at zero-bias, is at least of an order of magnitude higher than that of the quantum superconductive/memristive device in an aqueous or a biological media in the presence of a wide range collagen-1 concentration over 1-200 ng/mL compared under a fixed scan rate.

12. According to claim 11, wherein the supercurrent at the JJ toroidal vertex of the quantum superconductive/memcapacitive device is exponentially increase and proportional to collagen concentration over 1-200 ng/mL at 300 Hz using NIST human serum samples compared with the controls.

13. According to claim 1, wherein the first layer of nanoisland comprises of cross-linked conductive polymer of TCD/PEG/PVP/β-CD copolymer in the toroidal vertex quantum superconductive/memristive device.

14. According to claim 1, wherein the second layer of the polymer mixtures of bM-β-DMCD//PEG/PVP/TCD/ZnCl$_2$ has a volume ratio range from 6:1 to 10:1 for bM-β-DMCD to each of other component, except to ZnCl$_2$, 4:1 with the CD's concentration in 10-fold higher than that of PEG or PVP, respectively.

15. According to claim 1, wherein the polymer components of PEG, PVP and TCD can add one more biological protein MMP-2 and cross-linked on a gold surface in the absence of bM-β-DMCD and zinc chloride, to form a Josephson toroidal vertex quantum superconductive/memristive device without the needs for the procedures described in claim 1(a).

16. According to claim 15, wherein the Josephson toroidal vertex quantum superconductive/memristive MMP-2 protein device has nanostructure toroidal ring structures with thickness in 90 nm in the circular nanotubes, and the diameters of the toroidal are in the range of 2.3-5.5 μm, and the height of the toroidal is from 0.5 to 0.9 μm, Zinc atoms are located in the center or along the top of the edge of the toroidal ring.

17. According to claim 16, wherein the memristive MMP-2 protein device is a sensor having the capability to direct linearly sense 0.5 pg/mL to 500 pg/mL collagen-1 without denaturing procedures at the innate state by a CV method at 300 Hz.

18. According to claim 17, wherein the memristive MMP-2 protein device is a superconductor when at its active state, having the JJ tunneling current at zero-bias at very low 1 Hz and high 1 kHz and 10 kHz in PBS solution; and in human serum samples the measured JJ super current decreases in an exponential first order decay manner as the presence of spiked collagen-1 concentrations increases in 50 pg/mL, 1 ng/mL and 25 ng/mL at 300 Hz at zero-bias vs. the control.

19. The use of a device according to claim 1, further including the use for direct measuring the biomimetic CHAT . . . biomimetic MMP-2 . . . collagen-1 electron-relay communication voltage change comprising:

a) obtaining a sample immersed in a media which can be detected;

b) contacting the sample with a device, the device comprises an electrode having a first layer of an arrays of nanoislands organic superconductive membrane with acetyl modified cyclodextrin cross-linked with polymers of PEG, PVP and β-CD copolymer by self-assembling; a second layer comprising of an organometallic superlattice membrane that made of cross-linked TCD, PEG, PVP, bM-β-DMCD and embedded with zinc chloride fabricated by self-assembling lay on top of the first layer, and all layers of membranes affixed to said electrode;

c) setting up an appropriate fixed pulse current and apply the current onto the device;

d) setting up an appropriate pulse stepping time in order to measure voltage;

e) and measuring the cell voltage outcome in the media.

20. A method according to claim 19, wherein the sample is a protein, in specific is collagen-1.

21. According to claim 1, wherein the biomimetic Josephson toroidal vertex quantum superconductive/memristive device enabled direct detection of sub fg/mL collagen-1 with a wider analytical range of 5 fg/mL to 200 ng/mL having a Detection of Limits (DOL) of 0.43 pg/mL/cm$^2$, i.e., 14 fg/mL for this device with a relative percent of sum of squares pure error (RSSPE) of 0.05% at the high end and 0.5% at the low end, respectively.

* * * * *